US012714742B2

(12) United States Patent
Shone et al.

(10) Patent No.: US 12,714,742 B2
(45) Date of Patent: Aug. 25, 2026

(54) ***Clostridium difficile* ANTIGENS**

(71) Applicants: Secretary of State for Health and Social Care, London (GB); MicroPharm Limited, Newcastle Emlyn (GB)

(72) Inventors: Clifford Shone, Salisbury (GB); April Roberts, Salisbury (GB); Helen Ahern, Salisbury (GB); Michael Maynard-Smith, Salisbury (GB); John Landon, Newcastle Emlyn (GB)

(73) Assignees: Secretary of State for Health and Social Care, London (GB); MicroPharm Limited, Newcastle Emlyn (GB)

( * ) Notice: Subject to any disclaimer, the term of this patent is extended or adjusted under 35 U.S.C. 154(b) by 408 days.

(21) Appl. No.: 17/224,404

(22) Filed: Apr. 7, 2021

(65) Prior Publication Data

US 2021/0369830 A1 Dec. 2, 2021

Related U.S. Application Data

(62) Division of application No. 16/511,503, filed on Jul. 15, 2019, now abandoned, which is a division of application No. 13/878,150, filed as application No. PCT/GB2011/051910 on Oct. 5, 2011, now Pat. No. 10,369,206.

(30) Foreign Application Priority Data

Oct. 5, 2010 (GB) ..................................... 1016742

(51) Int. Cl.

| | |
|---|---|
| ***A61K 39/08*** | (2006.01) |
| ***A61K 38/16*** | (2006.01) |
| ***A61K 39/00*** | (2006.01) |
| ***A61K 39/40*** | (2006.01) |
| ***C07K 14/33*** | (2006.01) |
| ***C07K 16/1282*** | (2026.01) |

(52) U.S. Cl.

CPC ............ *A61K 39/08* (2013.01); *A61K 38/164* (2013.01); *A61K 39/40* (2013.01); *C07K 14/33* (2013.01); *C07K 16/1282* (2013.01); *A61K 2039/505* (2013.01); *C07K 2317/76* (2013.01); *C07K 2319/00* (2013.01)

(58) Field of Classification Search

CPC ...... A61K 39/08; A61K 38/164; A61K 39/40; A61K 2039/505; C07K 14/33; C07K 16/1282; C07K 2317/76; C07K 2319/00

See application file for complete search history.

(56) References Cited

U.S. PATENT DOCUMENTS

| | | | |
|---|---|---|---|
| 5,601,823 | A | 2/1997 | Williams et al. |
| 5,919,463 | A | 7/1999 | Thomas, Jr. et al. |
| 8,481,692 | B2 | 7/2013 | Sidhu et al. |
| 9,745,354 | B2 | 8/2017 | Ruppen et al. |
| 2005/0287150 | A1 | 12/2005 | Ambrosino et al. |
| 2007/0065466 | A1 | 3/2007 | Windle et al. |

FOREIGN PATENT DOCUMENTS

| | | | |
|---|---|---|---|
| WO | 96/12802 | A1 | 5/1996 |
| WO | 98/59053 | A1 | 12/1998 |
| WO | 00/61762 | A1 | 10/2000 |
| WO | 2006121422 | A2 | 11/2006 |
| WO | 2007/146139 | A2 | 12/2007 |
| WO | 2010/017383 | A1 | 2/2010 |
| WO | 2011/067616 | A1 | 6/2011 |
| WO | 2012/046061 | A3 | 4/2012 |

OTHER PUBLICATIONS

Belyi, I.F., and N.A. Varfolomeeva, "Construction of a Fusion Protein Carrying Antigenic Determinants of Enteric Clostridial Toxins," FEMS Microbiology Letters 225(2):325-329, Aug. 2003.

(Continued)

*Primary Examiner* — Robert A Zeman

(74) *Attorney, Agent, or Firm* — Christensen O'Connor Johnson Kindness PLLC

(57) ABSTRACT

The present application relates to recombinant *Clostridium difficile* antigens based on a fusion protein that consists of or comprises a first amino acid sequence and a second amino acid sequence, wherein: a) the first amino acid sequence is provided by an amino acid sequence that has at least 80% sequence identity with an amino acid sequence consisting of residues 1500-1850 of a *C. difficile* Toxin A sequence or residues 1500-1851 of a *C. difficile* Toxin B sequence; and b) the second amino acid sequence is provided by an amino acid sequence that has at least 80% sequence identity with an amino acid sequence consisting of a long repeat unit located within amino acid residues 1851-2710 of a *C. difficile* Toxin A sequence or within amino acid residues 1852-2366 of a *C. difficile* Toxin B sequence; though with the proviso that the fusion protein is not a polypeptide comprising amino acid residues 543-2710 of a *C. difficile* Toxin A and with the proviso that the fusion protein is not a polypeptide comprising amino acid residues 543-2366 of a *C. difficile* Toxin B. Also provided is the use of said antigens for the prevention/treatment/suppression of *Clostridium difficile* infection (CDI), together with methods for generating said antigens, methods for generating antibodies that bind to said antigens, and the use of said antibodies for the prevention/treatment/suppression of CDI.

14 Claims, 5 Drawing Sheets

Specification includes a Sequence Listing.

(56) References Cited

OTHER PUBLICATIONS

Boslego, J.W., and C.D. Deal, "Gonorrhea Vaccines: Etiologic Agent and Pathogenesis," Vaccines and Immunotherapy, Chapter 17, 1 page, 1991.
Castagliuolo, I., et al., "Clostridium difficile Toxin A Carboxyl-Terminus Peptide Lacking ADP-Ribosyltransferase Activity Acts as a Mucosal Adjuvant," Infections and Immunity 72(5):2827-2836, May 2004.
Colman, P.M., "Effects of Amino Acid Sequence Changes on Antibody-Antigen Interactions," Research in Immunology 145(1):33-36, 1994.
Ellis, R.W., "New Technologies for Making Vaccines," in Stanley J. Cryz, Jr. (ed.), Vaccines, W.B. Saunders Company, Philadelphia, 1988, Chapter 29, pp. 568-574.
Greenspan, N.S., and E.Di Cera, "Defining Epitopes: It's Not As Easy As It Seems," Nature Biotechnology 17(10):936-937, Oct. 1999.
Harlow, E., and D. Lane, "Antibodies A Laboratory Manual," Cold Spring Harbor Press Inc., Cold Spring Harbor, New York, 1988, pp. 23-35.
Ho, J.G.S., et al., "Crystal Structure of Receptor-Binding C-Terminal Repeats From *Clostridium difficile* Toxin A," Proceedings of the National Academy of Sciences of the USA (PNAS) 102(51):18373-18378, Dec. 2005.
Houghten, R.A., et al., "Relative Importance of Position and Individual Amino Acid Residues in Peptide Antigen-Antibody Interactions: Implications in the Mechanism of Antigenic Drift and Antigenic Shift," in Cold Spring Harbor Laboratory, "Vaccines 86 New Approaches to Immunization: Developing Vaccines Against Parasitic, Bacterial, and Viral Diseases," Cold Spring Harbor, New York, 1986, pp. 21-26.
Pruitt, R.N., et al., "Structural Determinants of *Clostridium difficile* Toxin A Glucosyltransferase Activity," Journal of Biological Chemistry 287(11):8013-8020, Mar. 2012.
Pruitt, R.N., et al., "Structural Organization of the Functional Domains of *Clostridium difficile* Toxins A and B," Proceedings of the National Academy of Sciences of the USA (PNAS) 107(30):13467-13472, Jul. 2010.
Reinert, D.J., et al., "Structural Basis for the Function of *Clostridium difficile* Toxin B," Journal of Molecular Biology 351(5):973-981, Sep. 2005.
Skolnick, J., and J.S. Fetrow, "From Genes to Protein Structure and Function: Novel Applications of Computational Approaches in the Genomic Era," Trends in Biotechnology 18(1):34-39, Jan. 2000.
Von Eichel-Streiber, C., et al., "Comparative Sequence Analysis of the *Clostridium difficile* Toxins A and B," Molecular and General Genetics 233(1-2):260-268, May 1992.
United Kingdom Intellectual Property Office, Patents Act 1977: Search Report Under Section 17, mailed Feb. 4, 2011, issued in corresponding Great Britain Application No. GB 101672.7, filed Oct. 5, 2010, 5 pages.
European Patent Office Written Opinion mailed Feb. 15, 2013, issued in corresponding International Patent Application No. PCT/GB2011/051910, 7 pages.
Written Opinion of the International Searching Authority mailed Apr. 5, 2013, issued in corresponding International Patent Application No. PCT/GB2011/051910, 6 pages.
Response to the Written Opinion of the International Searching Authority issued in corresponding International Patent Application No. PCT/GB2011/051910, mailed Apr. 15, 2013, 9 pages.
International Preliminary Report on Patentabilily mailed May 14, 2013, issued in corresponding International Patent Application No. PCT/GB2011/051910, 8 pages.
Redwan, EL.-R.M., et al., " Production and Purification of Ovine Anti-Tetanus Antibody," Comparative Immunology, Microbiology and Infectious Diseases 28(3):167-176, May 2005.
Van Dissel, J.T., et al., "Bovine antibody-enriched whey to aid in the prevention of a relapse of *Clostridium difficile* associated diarrhoea: preclinical and preliminary clinical data," Journal of Medical Microbiology, 54:197-205 (2005).
Torres, J.F., et al., "Evaluation of Formalin-Inactivated *Clostridium difficile* Vaccines Administered by Parenteral and Mucosal Routes of Immunization in Hamsters," Infection and Immunity, vol. 63(12):4619-4627, Dec. 1995.
Lyerly, D.M., et al., "Passive Immunization of Hamsters against Disease Caused by *Clostridium difficile* by Use of Bovine Immunoglobulin G Concentrate," Infection and Immunity, vol. 59(6):2215-2218, Jun. 1991.
Libby, J.M., et al., "Production of Antitoxins to Two Toxins of *Clostridium difficile* and Immunological Comparison of the Toxins by Cross-Neutralization Studies," Infection and Immunity, vol. 35(1):374-376, Jan. 1982.
Giannasca, P.J., et al., "Serum Antitoxin Antibodies Mediate Systemic and Mucosal Protection from *Clostridium difficile* Disease in Hamsters," Infection and Immunity, vol. 67(2):527-538, Feb. 1999.
Alpar, H.O., et al., "Strategies for DNA Vaccine Delivery," Expert Opinion on Drug Delivery 2(5):829-842, Sep. 2005.

*Clostridium difficile* ANTIGENS

CROSS-REFERENCES TO RELATED APPLICATIONS

This application is a division of U.S. application Ser. No. 16/511,503, filed Jul. 15, 2019, which is a division of U.S. application Ser. No. 13/878,150, filed Jun. 25, 2013, now U.S. Pat. No. 10,369,206, issued Aug. 6, 2019, which is the National Stage of International Application No. PCT/GB2011/051910, filed Oct. 5, 2011, which claims the benefit of GB Application No. 1016742.7, filed Oct. 5, 2010.

STATEMENT REGARDING SEQUENCE LISTING

The sequence listing associated with this application is provided in text format in lieu of a paper copy and is hereby incorporated by reference into the specification. The name of the text file containing the sequence listing is MASQ174232_SEQ_List_final_20210406_ST25.txt. The text file is 1000 KB; was created on Apr. 6, 2021; and is being submitted via EFS-Web with the filing of the specification.

BACKGROUND

The present invention relates to antigens for the prevention/treatment/suppression of *Clostridium difficile* infection (CDI). Also provided are methods for generating said antigens, methods for generating antibodies that bind to said antigens, and the use of said antibodies for the prevention/treatment/suppression of CDI.

*Clostridium difficile* infection (CDI) is now a major problem in hospitals worldwide. The bacterium causes nosocomial, antibiotic-associated disease which manifests itself in several forms ranging from mild self-limiting diarrhoea to potentially life-threatening, severe colitis. Elderly patients are most at risk from these potentially life-threatening diseases and incidents of CDI have increased dramatically over the last 10 years. In 2010 in the UK there were over 21,000 cases of CDI with over 2,700 associated deaths. CDI costs the UK National Health Service in excess of £500M per annum.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of different strains are also indicative of sequence variation within the *C. difficile* toxin family. For example, there is an approximate 13% sequence difference with the C-terminal 60 kDa region of toxinotype 0 Toxin B compared to the same region in toxinotype III Toxin B.

Strains of *C. difficile* produce a variety of virulence factors, notable among which are several protein toxins: Toxin A, Toxin B and, in some strains, a binary toxin which is similar to *Clostridium perfringens* iota toxin. Toxin A is a large protein cytotoxin/enterotoxin which plays a role in the pathology of infection and may influence the gut colonisation process. Outbreaks of CDI have been reported with Toxin A-negative/Toxin B-positive strains, which indicates that Toxin B is also capable of playing a key role in the disease pathology.

The genetic sequences encoding Toxin A and Toxin B (Mw 308 k and Mw 269 k, respectively) are known—see, for example, Moncrief et al. (1997) Infect. Immun 63:1105-1108. The two toxins have high sequence homology and are believed to have arisen from gene duplication. The toxins also share a common structure (see FIG. 1), namely an N-terminal glucosyl transferase domain, a central hydrophobic region, four conserved cysteines, and a long series of C-terminal repeating units (RUs).

Toxin A comprises 39 contiguous repeating units (RUs), which span amino acid residues 1851-2710 of the Toxin A polypeptide sequence. Toxin B comprises fewer RUs (between 19 and 24) which span amino acid residues 1852-2366 of the Toxin B polypeptide sequence. For both Toxins A and B, the repeating units are of two different types: short repeats (SRs) of approximately 15-25 residues and long repeats (LRs) of approximately 30 residues. The LRs are separated from each other by 3 or 4 SRs, and the LRs together with the flanking SRs provide the binding sites for the carbohydrate receptor of the toxins. Toxin A has 7 LRs within its C-terminal domain, which are believed to provide 7 receptor binding sites (Greco et al. (2005) Nature Structural Biol. 13:460-461). Toxin B has 4 LRs, which are believed to provide 4 carbohydrate binding units. Examples of the Toxin A and Toxin B SR/LR clusters (also known as receptor-binding "Modules") vary in size from 92-141 amino acid residues, and are exemplified by reference to Tables 1 and 2.

Both Toxins A and B exert their mechanisms of action via multi-step mechanisms, which include binding to receptors on the cell surface, internalisation followed by translocation and release of the effector domain into the cell cytosol, and finally intracellular action. Said mechanism of action involves the inactivation of small GTPases of the Rho family. In this regard, the toxins catalyse the transfer of a glucose moiety (from UDP-glucose) onto an amino residue of the Rho protein. Toxins A and B also contain a second enzyme activity in the form of a cysteine protease, which appears to play a role in the release of the effector domain into the cytosol after translocation. The *C. difficile* binary toxin modifies cell actin by a mechanism which involves the transfer of an ADP-ribose moiety from NAD onto its target protein.

Current therapies for the treatment of *C. difficile* infection rely on the use of antibiotics, notably metronidazole and vancomycin. However, these antibiotics are not effective in all cases and 20-30% of patients suffer relapse of the disease. Of major concern is the appearance in the UK of more virulent strains, which were first identified in Canada in 2002. These strains, which include those belonging to PCR ribotype 027 and toxinotype III, cause CDI with a directly attributable mortality more than 3-fold that observed previously.

New therapeutics are therefore required especially urgently since the efficacy of current antibiotics appears to be decreasing.

An attractive alternative is the use of antibodies which bind to and neutralise the activity of Toxin A and Toxin B. This is based on the knowledge that strains of *C. difficile* that do not release these toxins, so called non-toxigenic strains, do not cause CDI. In one approach patients with CDI or subjects at risk of developing such infections can be immunised with antigens which result in an increase in circulating and mucosal antibodies directed against Toxin A and Toxin B. This is defined as active immunisation. Alternatively, animals, such as horses or sheep, can be immunised, their sera collected and the antibodies purified for administration to patients—passive immunisation.

A critical requirement for both active and passive immunisation is the availability of suitable antigens with which to immunise the patient or animal respectively. These can comprise the natural toxins which can be purified from the media in which suitable toxigenic strains of *C. difficile* have been cultured. There are several disadvantages to this approach. Both Toxin A and Toxin B are present in culture medium in only small amounts and are difficult to purify without incurring significant losses. Thus, it will be both costly and difficult to obtain the amounts necessary to meet world-wide needs. In addition, the natural toxins are unstable and, because of their toxicity, must be converted to their toxoids (inactivated toxins) prior to their use as immunogens.

The above mentioned problems have resulted in there being few available *C. difficile* vaccine candidates. To-date, the only CDI vaccine in late-stage development is based on a mixture of native (i.e., naturally occurring) Toxins A and B, which have been inactivated by chemical modification (Salnikova et al. (2008), J. Pharm. Sci., 97:3735-3752).

One alternative to the use of natural toxins and their toxoids, involves the design, development and use of recombinant fragments derived from Toxins A and B. Among their advantages are that such fragments can be expressed and purified in large amounts and at lower cost than the native toxins. Examples of existing antigens intended for use in treating/preventing a *C. difficile* infection include peptides based on the C-terminal repeating units (RUs) of Toxin A or Toxin B—see, for example, WO00/61762. A problem with such antigens, however, is that they are either poorly immunogenic (i.e., the antigens produce poor antibody titres), or, where higher antibody titres are produced, the antibodies demonstrate poor neutralising efficacy against *C. difficile* cytotoxic activity (i.e., insufficient neutralising antibodies are produced).

There is therefore a need in the art for new vaccines/therapies/therapeutics capable of specifically addressing *C. difficile* infection (CDI). This need is addressed by the present invention, which solves one or more of the above-mentioned problems.

In one embodiment, the present invention provides antigens that are able to induce a potent toxin-neutralising response against *C. difficile* Toxin A and/or B. The invention also provides methods for preparing recombinant antigens. In another embodiment, said antigens are used as immunogens to enable the large-scale preparation of therapeutic antibodies. In a further embodiment, said antibodies are able to induce a potent toxin-neutralising response against *C. difficile* Toxin A and/or B and therefore have prophylactic and/or therapeutic applications.

As mentioned above (see WO00/61762), previous studies describe vaccine preparations based on the C-terminal, repeating units (RUs) of Toxin A and/or Toxin B. Said RU fragments have a poor toxin-neutralising effect, and/or are difficult to manufacture in large quantities.

In contrast, the present invention provides a *C. difficile* antigen based on a Toxin A and/or a Toxin B repeat unit, and further includes an additional *C. difficile* toxin domain, which the present inventors believe provides an important 'scaffold' function to the antigen. Said antigens of the invention demonstrate good toxin-neutralising immune responses and/or are readily manufactured in large quantities.

The present inventors have surprisingly identified that the presence of a "scaffold" first amino acid sequence (as above) provides a protective (toxin-neutralising) immune response that is between 10-100 fold increased as compared to corresponding fragments comprising just the repeat regions of Toxin A or Toxin B. Tables 3-10 clearly show the superior capacity of fusion proteins of the present invention to elicit a toxin-neutralising immune response compared to fragments containing just the repeat domains of a *C. difficile* Toxin. Comparison of the data in Tables 5 and 6 confirms that the Toxin B-based constructs of the present invention elicit a considerably more potent toxin-neutralising immune response than that of a corresponding construct based solely on the C-terminal repeating units of Toxin B (designated TxB2). In more detail, after an 18-week immunisation period, the toxin-neutralising immune response provided by constructs of the present invention was approximately 128-fold higher than that provided by the TxB2 construct. Tables 9 and 10 show similar data for Toxin A-based constructs of the present invention. Comparison of the data in said Tables confirms that the Toxin A-based constructs of the present invention elicit a considerably more potent toxin-neutralising immune response than that of a corresponding construct based solely on the C-terminal repeating units of Toxin A (designated TxA2). In more detail, after an 18-week immunisation period, the toxin-neutralising immune response provided by constructs of the present invention was 12-fold higher than that provided by the TxA2 construct.

These findings are surprising for a number of reasons. Previous studies have shown that toxin fragments consisting of the *C. difficile* Toxin RUs fold correctly, readily crystallise to yield an ordered structure (Ho et al. (2005) Proc. Natl. Acad. Sci. USA, 102:18373-18378), and bind carbohydrate moieties that mimic the natural *C. difficile* Toxin receptors (Greco et al. (2006) Nature Structure & Molecular Biology, 13: 460-461). Thus, the scientific evidence to-date supports and is consistent with the prior art use (e.g., WO 00/61762) of fragments consisting of the *C. difficile* Toxin RUs in antigenic formulations. More importantly, however, a further study has confirmed that antibodies raised against a whole *C. difficile*, while recognising a fragment consisting of the entire RU region alone, failed to recognise a fragment consisting of a "scaffold" region based on residues 901-1750 of the *C. difficile* same toxin (Genth et al., (2000) Infect. Immun., 68:1094-1101). These data therefore suggest that domains within "scaffold" residues 901-1750 contribute no significant antibody-binding structural determinants. In this regard, other than at the peptide bond, there is no contact in the tertiary structure between "scaffold" toxin domains and the C-terminal repeat region residues—see Pruitt et al., (2010) Proc. Natl. Acad. Sci. USA, 1002199107 online publication. Collectively, it is therefore extremely surprising that the inclusion of a *C. difficile* "scaffold" region within recombinant immunogens of Toxins A and/or Toxin B has the effect of significantly enhancing the toxin-neutralising immune response.

A first aspect of the present invention provides a fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1850 of a *C. difficile* Toxin A sequence; and 2) the second amino acid sequence is provided by an amino acid sequence that has at least 80% sequence identity with an amino acid sequence consisting of a long repeat unit located within amino acid residues 1851-2710 of a *C. difficile* Toxin A sequence;

with the proviso that the fusion protein is not a polypeptide comprising amino acid residues 543-2710 of a *C. difficile* Toxin A.

Reference to a *C. difficile* Toxin A sequence means the amino acid sequence of a naturally-occurring *C. difficile* Toxin A (also referred to as a *C. difficile* Toxin A reference sequence). Examples of such sequences are readily understood by a skilled person, and some of the more common naturally-occurring Toxin A sequences are identified in the present specification (see, for example, SEQ ID NOs: 1 and 3) as well as throughout the literature.

Reference to 'at least 80% sequence identity' throughout this specification is considered synonymous with the phrase 'based on' and may embrace one or more of at least 85%, at least 90%, at least 93%, at least 95%, at least 97%, at least 99%, and 100% sequence identity. When assessing sequence identity, a reference sequence having a defined number of contiguous amino acid residues is aligned with an amino acid sequence (having the same number of contiguous amino acid residues) from the corresponding portion of a fusion protein of the present invention.

In one embodiment, the first amino acid sequence is based on (i.e., has at least 80% sequence identity with) amino acid residues 544-1850 of a *C. difficile* Toxin A. In another embodiment, the first amino acid sequence is based on an N-terminal truncation of amino acid residues 544-1850 of a *C. difficile* Toxin A, such as amino acid residues 564-1850, amino acid residues 584-1850, amino acid residues 594-1850, amino acid residues 614-1850, amino acid residues 634-1850, amino acid residues 654-1850, amino acid residues 674-1850, amino acid residues 694-1850, amino acid residues 714-1850, amino acid residues 734-1850, amino acid residues 754-1850, amino acid residues 767-1850, amino acid residues 770-1850, amino acid residues 774-1850, amino acid residues 794-1850, amino acid residues 814-1850, amino acid residues 834-1850, amino acid residues 854-1850, amino acid residues 874-1850, amino acid residues 894-1850, amino acid residues 914-1850, amino acid residues 934-1850, amino acid residues 954-1850, amino acid residues 974-1850, amino acid residues 994-1850, amino acid residues 1014-1850, amino acid residues 1034-1850, amino acid residues 1054-1850, amino acid residues 1074-1850, amino acid residues 1094-1850, amino acid residues 1104-1850, amino acid residues 1124-1850, amino acid residues, amino acid residues 1131-1850, amino acid residues 1144-1850, amino acid residues 1164-1850, amino acid residues 1184-1850, amino acid residues 1204-1850, amino acid residues 1224-1850, amino acid residues 1244-1850, amino acid residues 1264-1850, amino acid residues 1284-1850, amino acid residues 1304-1850, amino acid residues 1324-1850, amino acid residues 1344-1850, amino acid residues 1364-1850, amino acid residues 1384-1850, amino acid residues 1404-1850, amino acid residues 1424-1850, amino acid residues 1444-1850, amino acid residues 1464-1850, or amino acid residues 1684-1850 of a *C. difficile* Toxin A; though always with the proviso that the fusion protein is not a polypeptide comprising amino acid residues 543-2710 of a *C. difficile* Toxin A. By way of example only, the above amino acid position numbering may refer to the *C. difficile* Toxin A sequences identified as SEQ ID NOs: 1 and/or 3.

In one embodiment, the second amino acid sequence is based on (i.e., has at least 80% sequence identity with) any one or more of the long repeat (LR) amino acid sequences from a *C. difficile* Toxin A sequence. By way of example only, said one or more LR sequences may be based on any of SEQ ID NOs: 60, 62, 64, 66, 68, 70 and/or 72. In another embodiment, the second amino acid sequence is based on an entire Module sequence of a *C. difficile* Toxin A sequence, which includes a LR amino acid sequence plus one or more of its (flanking) short repeat (SR) sequences. By way of example only, the second amino acid may be based on one or more of SEQ ID NOs: 61, 63, 65, 67, 69, 71 and/or 73. In another embodiment, the second amino acid sequence is based on a sequence consisting of or comprising the entire Module 1 amino acid sequence from a *C. difficile* Toxin A sequence (residues 1851-2007)—see, for example, the Module 1 as illustrated in Table 1. In another embodiment, the second amino acid sequence is based on a sequence consisting of or comprising the entire Module 1 plus Module 2 amino acid sequence from a *C. difficile* Toxin A sequence (e.g., residues 1851-2141 as illustrated in Table 1). In another embodiment, the second amino acid sequence is based on a sequence consisting of or comprising the entire Module 1 plus Module 2 plus Module 3 amino acid sequence from a *C. difficile* Toxin A sequence (e.g., residues 1851-2253 as illustrated in Table 1). In another embodiment, the second amino acid sequence is based on a sequence consisting of or comprising the entire Module 1 plus Module 2 plus Module 3 plus Module 4 amino acid sequence from a *C. difficile* Toxin A sequence (e.g., residues 1851-2389 as illustrated in Table 1). In another embodiment, the second amino acid sequence is based on a sequence consisting of or comprising the entire Module 1 plus Module 2 plus Module 3 plus Module 4 plus Module 5 amino acid sequence from a *C. difficile* Toxin A sequence (e.g., residues 1851-2502 as illustrated in Table 1). In another embodiment, the second amino acid sequence is based on a sequence consisting of or comprising the entire Module 1 plus Module 2 plus Module 3 plus Module 4 plus Module 5 plus Module 6 amino acid sequence from a *C. difficile* Toxin A sequence (e.g., residues 1851-2594 as illustrated in Table 1). In another embodiment, the second amino acid sequence is based on a sequence consisting of or comprising the entire Module 1 plus Module 2 plus Module 3 plus Module 4 plus Module 5 plus Module 6 plus Module 7 amino acid sequence from a *C. difficile* Toxin A sequence (e.g., residues 1851-2710 as illustrated in Table 1). By way of example only, the above amino acid position numbering may refer to the *C. difficile* Toxin A sequences identified as SEQ ID NOs: 1 and/or 3.

Any of the embodiments for the second amino acid sequence may be combined with any of the embodiments described for the first amino acid sequence.

In one embodiment a fusion protein is provided, which comprises or consists of a sequence based on amino acid residues 1851-2710 of a Toxin A sequence (or a portion thereof) and an N-terminal polypeptide based on amino acid residues 770-1850 of a Toxin A polypeptide (or a portion thereof).

In another embodiment a fusion protein is provided, which comprises or consists of a sequence based on amino acid residues 1851-2710 of a Toxin A sequence (or a portion thereof) and an N-terminal polypeptide based on amino acid residues 1131-1850 of a Toxin A polypeptide.

In another embodiment a fusion protein is provided, which comprises or consists of a sequence based on amino acid residues 770-2710 or 1131-2710 of a Toxin A polypeptide (e.g., SEQ ID NOs 5, 6, 7, 8, 18, 19, 20, 21, 22, 28, 29, 30, 31, 32, 33, 34, 35, 36, 37, 38, 39, 40, 41, 42, 43, or 58).

In another embodiment a fusion protein is provided, which comprises or consists of a sequence based on amino acid residues 770-2007, 770-2141, 770-2253, 770-2389 or 1131-2007, 1131-2141, 1131-2253 or 1131-2389 of a Toxin A polypeptide (e.g., SEQ ID NO 59).

A related first aspect of the present invention provides a fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1851 of a *C. difficile* Toxin B sequence; and 2) the second amino acid sequence is provided by an amino acid sequence that has at least 80% sequence identity with an amino acid sequence consisting of a long repeat unit located within amino acid residues 1852-2366 of a *C. difficile* Toxin B sequence;

with the proviso that the fusion protein is not a polypeptide comprising amino acid residues 543-2366 of a *C. difficile* Toxin B.

Reference to a *C. difficile* Toxin B sequence means the amino acid sequence of a naturally-occurring *C. difficile* Toxin B (also referred to as a *C. difficile* Toxin B reference sequence). Examples of such sequences are readily understood by a skilled person, and some of the more common naturally-occurring Toxin B sequences are identified in the present specification (see, for example, SEQ ID NOs: 2 and 4) as well as throughout the literature.

In one embodiment, the first amino acid sequence is based on (i.e., has at least 80% sequence identity with) amino acid residues 544-1851 of a *C. difficile* Toxin B. In another embodiment, the first amino acid sequence is based on an N-terminal truncation of amino acid residues 544-1851 of a *C. difficile* Toxin B, such as amino acid residues 564-1851, amino acid residues 584-1851, amino acid residues 594-1851, amino acid residues 614-1851, amino acid residues 634-1851, amino acid residues 654-1851, amino acid residues 674-1851, amino acid residues 694-1851, amino acid residues 714-1851, amino acid residues 734-1851, amino acid residues 754-1851, amino acid residues 767-1851, amino acid residues 770-1851, amino acid residues 774-1851, amino acid residues 794-1851, amino acid residues 814-1851, amino acid residues 834-1851, amino acid residues 854-1851, amino acid residues 874-1851, amino acid residues 894-1851, amino acid residues 914-1851, amino acid residues 934-1851, amino acid residues 954-1851, amino acid residues 974-1851, amino acid residues 994-1851, amino acid residues 1014-1851, amino acid residues 1034-1851, amino acid residues 1054-1851, amino acid residues 1074-1851, amino acid residues 1094-1851, amino acid residues 1104-1851, amino acid residues 1124-1851, amino acid residues 1131-1851, amino acid residues 1144-1851, amino acid residues 1164-1851, amino acid residues 1184-1851, amino acid residues 1204-1851, amino acid residues 1224-1851, amino acid residues 1244-1851, amino acid residues 1264-1851, amino acid residues 1284-1851, amino acid residues 1304-1851, amino acid residues 1324-1851, amino acid residues 1344-1851, amino acid residues 1364-1851, amino acid residues 1384-1851, amino acid residues 1404-1851, amino acid residues 1424-1851, amino acid residues 1444-1851, amino acid residues 1464-1851, or amino acid residues 1684-1851 of a *C. difficile* Toxin B; though always with the proviso that the fusion protein is not a polypeptide comprising amino acid residues 543-2366 of a *C. difficile* Toxin B. By way of example only, the above amino acid position numbering may refer to the *C. difficile* Toxin B sequences identified as SEQ ID NOs: 2 and/or 4.

In one embodiment, the second amino acid sequence is based on (i.e., has at least 80% sequence identity with) any one or more of the long repeat (LR) amino acid sequences from a *C. difficile* Toxin B sequence. By way of example only, said one or more LR sequences may be based on any of SEQ ID NOs: 74, 76, 78 and/or 80. In another embodiment, the second amino acid sequence is based on an entire Module sequence of a *C. difficile* Toxin B sequence, which includes a LR amino acid sequence plus one or more of its (flanking) short repeat (SR) sequences. By way of example only, the second amino acid sequence may be based on one or more of SEQ ID NOs: 75, 77, 79 and/or 81. In another embodiment the second amino acid is based on a sequence consisting of or comprising the entire Module 1 amino acid sequence from a *C. difficile* Toxin B sequence (residues 1852-2007)—see, for example, the Module 1 as illustrated in Table 2. In another embodiment, the second amino acid sequence is based on a sequence consisting of or comprising the entire Module 1 plus Module 2 amino acid sequence from a *C. difficile* Toxin B sequence (e.g., residues 1852-2139 as illustrated in Table 2). In another embodiment, the second amino acid sequence is based on a sequence consisting of or comprising the entire Module 1 plus Module 2 plus Module 3 amino acid sequence from a *C. difficile* Toxin B sequence (e.g., residues 1851-2273 as illustrated in Table 2). In another embodiment, the second amino acid sequence is based on a sequence consisting of or comprising the entire Module 1 plus Module 2 plus Module 3 plus Module 4 amino acid sequence from a *C. difficile* Toxin B sequence (e.g., residues 1851-2366 as illustrated in Table 2). By way of example only, the above amino acid position numbering may refer to the *C. difficile* Toxin B sequences identified as SEQ ID NOs: 2 and/or 4.

Any of the embodiments for the second amino acid sequence may be combined with any of the embodiments described for the first amino acid sequence.

In one embodiment, when the first and second amino acid sequences are both based on Toxin B sequences, the fusion protein may consist of or comprise an amino acid sequence that is based on at least 871 or at least 876 or at least 881 or at least 886 or at least 891 or at least 896 or at least 901 contiguous amino acid residues (e.g., starting from the C-terminal amino acid residue) of a *C. difficile* Toxin B sequence, such as SEQ ID NOs: 2 and/or 4).

In one embodiment a fusion protein is provided, which comprises or consists of a sequence based on amino acid residues 1852-2366 of a Toxin B polypeptide (or a portion thereof) and an N-terminal polypeptide based on amino acid residues 767-1851 of a Toxin B polypeptide (or a portion thereof).

In another embodiment a fusion protein is provided, which comprises or consists of a sequence based on amino acid residues 1852-2366 of a Toxin B polypeptide (or a portion thereof) and an N-terminal polypeptide based on amino acid residues 1145-1851 of a Toxin B polypeptide (or a portion thereof).

In another embodiment a fusion protein is provided, which comprises or consists of a sequence based on amino acid residues 767-2366 or 957-2366 or 1138-2366 of a Toxin B polypeptide (e.g., SEQ ID NOs 9, 10, 11, 12, 13, 14, 23, 24, 25, 26, 27, 44, 45, 46, 47, 48, 49, 50, 51, 52, 53, 54, 55, 56 or 57).

The present invention also provides fusion proteins that are chimeras of Toxin A and B domains. For example, one or more long repeat unit (optionally including one or more short repeat unit; or one, more or all Modules) based on a Toxin B polypeptide may be combined with a "scaffold" region of a Toxin A polypeptide. Similarly, one or more long repeat unit (optionally including one or more short repeat unit; or one, more or all Modules) based on a Toxin A polypeptide may be combined with a "scaffold" region of a Toxin B polypeptide.

Thus, a further related aspect of the present invention provides a hybrid/chimera fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1850 of a *C. difficile* Toxin A sequence; and 2) the second amino acid sequence is provided by an amino acid sequence that has at least 80% sequence identity with an amino acid sequence consisting of a long repeat unit located within amino acid residues 1852-2366 of a *C. difficile* Toxin B sequence;

with the proviso that the fusion protein is not a polypeptide comprising amino acid residues 543-2710 of a *C. difficile* Toxin A;

and with the proviso that the fusion protein is not a polypeptide comprising amino acid residues 543-2366 of a *C. difficile* Toxin B.

Embodiments of the first and second amino acid sequences are as detailed above.

For example, in one embodiment a fusion protein is provided, which comprises or consists of a sequence based on amino acid residues 1852-2366 of a Toxin B polypeptide (or a portion thereof) and an N-terminal polypeptide based on amino acid residues 770-1849 of a Toxin A polypeptide (or a portion thereof).

In another embodiment a fusion protein is provided, which comprises or consists of a sequence based on amino acid residues 1852-2366 of a Toxin B polypeptide (or a portion thereof) and an N-terminal polypeptide based on amino acid residues 1131-1849 of a Toxin A polypeptide (or a portion thereof).

In another embodiment, a fusion protein is provided, which comprises or consists of a sequence based on amino acid residues 1852-2366 of a Toxin B polypeptide (or a portion thereof) and an N-terminal polypeptide based on amino acid residues 1500-1849 of a Toxin A polypeptide (or a portion thereof). In one embodiment, said Toxin A polypeptide component is preferably based on a sequence that is shorter than residues 543-1849 of a Toxin A polypeptide.

Specific examples include fusion proteins consisting of or comprising an amino acid sequence based on any one or more of SEQ ID NOs: 16 or 17.

Similarly, a further related first aspect of the present invention provides a hybrid/chimera fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1851 of a *C. difficile* Toxin B sequence; and 2) the second amino acid sequence is provided by an amino acid sequence that has at least 80% sequence identity with an amino acid sequence consisting of a long repeat unit located within amino acid residues 1851-2710 of a *C. difficile* Toxin A sequence;

with the proviso that the fusion protein is not a polypeptide comprising amino acid residues 543-2710 of a *C. difficile* Toxin A and with the proviso that the fusion protein is not a polypeptide comprising amino acid residues 543-2366 of a *C. difficile* Toxin B.

Embodiments of the first and second amino acid sequences are as detailed above.

In one embodiment a fusion protein is provided, which comprises or consists of a sequence based on amino acid residues 1850-2710 of a Toxin A polypeptide (or a portion thereof) and an N-terminal polypeptide based on amino acid residues 767-1851 of a Toxin B polypeptide (or a portion thereof).

In another embodiment a fusion protein is provided, which comprises or consists of a sequence based on amino acid residues 1850-2710 of a Toxin A polypeptide (or a portion thereof) and an N-terminal polypeptide based on amino acid residues 1145-1851 of a Toxin B polypeptide (or a portion thereof).

In another embodiment, a fusion protein is provided, which comprises or consists of a sequence based on amino acid residues 1850-2710 of a Toxin A polypeptide (or a portion thereof) and an N-terminal polypeptide based on 1500-1851 of a Toxin B polypeptide. In one embodiment, the Toxin B polypeptide component is preferably based on a sequence that is shorter than residues 543-1851 of a Toxin B polypeptide.

Specific examples include fusion proteins consisting of or comprising an amino acid sequence based on SEQ ID NO: 15.

As hereinbefore described, the present invention relates to fusion proteins based on a "scaffold" section plus a LR portion (of the C-terminal repeating units) of a *C. difficile* Toxin A and/or a *C. difficile* Toxin B. In this regard, the total portion(s) of said fusion proteins that is based on said *C. difficile* Toxin A and/or Toxin B sequences typically amounts to a maximum of 1940 contiguous amino acid residues (for example a maximum of 1890, or 1840, or 1790, or 1740, or 1690, or 1640, or 1590, or 1540, or 1490, 1440, or 1390, or 1340, or 1290, or 1240 contiguous amino acid residues).

In one embodiment, the fusion protein substantially lacks cysteine protease activity. In another (or the same) embodiment, the fusion protein substantially lacks glucosyl transferase activity. For example, part or all of the amino acid sequence(s) providing said activity (activities) are typically absent (e.g., deleted) from the fusion proteins of the present invention. These enzymatic activities are present in native Toxin A and/or Toxin B, and are associated with N-terminal domains of said Toxins (see FIG. 1).

In another embodiment, the fusion protein substantially lacks the glucosyl transferase domain (amino acid residues 1-542 Toxin A; amino acid residues 1-543 Toxin B) of a native *C. difficile* Toxin. In another (or the same) embodiment, the fusion protein substantially lacks the cysteine protease domain (amino acid residues 543-770 Toxin A; 544-767 Toxin B) of a native *C. difficile* Toxin. Said amino acid residue numbering refers to any Toxin A or Toxin B toxinotype, for example any one or more of the reference Toxin A and/or Toxin B toxinotype SEQ ID NOs recited in the present specification. Accordingly, said amino acid residue numbering may refer to any specific Toxin A and/or Toxin B reference SEQ ID NOs recited in the present specification including an amino acid sequence variant having at least 80%, at least 85%, at least 90%, at least 93%, at least 95%, at least 97%, or at least 99% thereto.

Fusion protein constructs of the invention may be derived from any Toxin A and/or B sequence (including any toxinotype sequence), such as those illustrated in the present specification. For example, in one embodiment, first and/or second amino acid sequences are derived from Toxins A and/or B of toxinotype 0 (SEQ ID NOs: 1 and 2, respectively). In another embodiment, first and/or second amino acid sequences are derived from Toxins A and/or B of toxinotype 3 (SEQ NOs: 3 and 4, respectively).

Fusion proteins of the invention may further comprise a fusion protein partner to facilitate soluble expression. Fusion protein partners may be attached at the N- or C-terminus of the antigen construct but are usually placed at the N-terminal end. Examples of fusion partners are: NusA, thioredoxin, maltose-binding protein, small ubiquitin-like molecules (Sumo™-tag). To facilitate removal of the fusion protein partner during purification, a unique protease site may be inserted between the fusion protein partner and the fusion protein per se. Such protease sites may include those for thrombin, factor Xa, enterokinase, PreScission™, Sumo™. Alternatively, removal of the fusion protein partner may be achieved via inclusion of an intein sequence between the fusion protein partner and the fusion protein per se. Inteins are self cleaving proteins and in response to a stimulus (e.g., lowered pH) are capable of self splicing at the junction between the intein and the antigen construct thus eliminating the need for the addition of specific proteases. Examples of inteins include domains derived from *Mycobacterium tuberculosis* (RecA), and *Pyrococcus horikoshii* (RadA) (Fong et al., (2010) Trends Biotechnol. 28:272-279).

To facilitate purification, fusion proteins of the invention may include one or more purification tags to enable specific chromatography steps (e.g., metal ion chelating, affinity chromatography) to be included in the purification processes. Such purification tags may, for example, include: repeat histidine residues (e.g., 6-10 histidine residues), maltose binding protein, glutathione S-transferase; and streptavidin. These tags may be attached at the N- and/or C-terminus of the antigen fusion proteins of the invention. To facilitate removal of such tags during purification, protease sites and/or inteins (examples above) may be inserted between the fusion protein and the purification tag(s).

Thus, a typical fusion protein construct of the invention (starting from the N-terminus) may comprise:

a first purification tag
a fusion protein partner (to facilitate expression)
a first (preferably specific) protease sequence or intein sequence
the Toxin A and/or B antigen sequence
an optional second (preferably specific) protease sequence or intein sequence
an optional second purification tag The first and second purification tags may be the same or different. Similarly, the first and second protease/intein sequence may be the same or different. The first and second options are preferably different to enable selective and controllable cleavage/purification.

Specific examples of such fusion protein constructs are show in SEQ ID NOs: 18-27.

In one embodiment spacers may be introduced to distance the purification tag from the fusion protein—this may help to increase binding efficiency to affinity purification column media. The spacer may be placed (immediately) after the purification tag or between the fusion protein partner and the fusion protein per se. Typical spacer sequences may consist of between 10-40 amino acid residues to give either a linear or alpha-helical structure.

Accordingly, in one embodiment, a fusion protein construct of the invention may comprise (starting from the N-terminus):

a first purification tag
an optional first spacer sequence
a fusion protein partner (to facilitate expression)
an optional second spacer sequence
a (preferably specific) protease sequence or intein sequence
the Toxin A and/or B derived antigen sequence
an optional second (preferably specific) protease sequence or intein sequence
an optional third spacer sequence
an optional second purification tag Specific examples of such protein fusion constructs are shown in SEQ ID Nos: 28-57.

Genes encoding the constructs of the invention may be generated by PCR from *C. difficile* genomic DNA and sequenced by standard methods to ensure integrity. Alternatively and preferably genes may be synthesised providing the optimal codon bias for the expression host (e.g., *E. coli, Bacillus megaterium*). Thus, the present invention provides corresponding nucleic acid sequences that encode the aforementioned fusion proteins of the present invention.

Accordingly, a second aspect of the present invention provides a method for expressing one or more of the aforementioned fusion proteins, said method comprising:

1) providing a nucleic acid sequence that encodes one or more of said fusion proteins in a host cell, wherein said nucleic acid sequence is operably linked to a promoter; and
2) expressing said nucleic acid sequence in the host cell Fusion proteins of the invention may be formulated as vaccines for human or animal use in a number of ways. For example, formulation may include treatment with an agent to introduce intra-molecular cross-links. One example of such an agent is formaldehyde, which may be incubated, for example, with antigen fusion proteins of the invention for between 1-24 hours. Alternatively, longer incubation times of, for example, up to 2, 4, 6, 8 or 10 days may be employed. Following treatment with such an agent, antigen fusions of the invention may be combined with a suitable adjuvant, which may differ depending on whether the antigen fusion protein is intended for human or animal use.

A human or animal vaccine formulation may contain Toxin A and/or Toxin B and/or corresponding hybrid/chimera antigen fusions of the present invention. Thus, in one embodiment, a vaccine formulation procedure of the present invention comprises the following steps:

providing a recombinant Toxin A and/or Toxin B and/or hybrid/chimera toxin fusion protein in suitable buffer system
optionally (preferably) treating said mixture with a toxoiding component such as formaldehyde
optionally transferring the fusion proteins to a new buffer system
combining the fusion proteins with one or more suitable adjuvants and optionally other excipients Accordingly, a third aspect of the present invention provides one or more of the aforementioned fusion proteins of the invention, for use in the generation of antibodies that bind to *C. difficile* Toxin A and/or Toxin B. In one embodiment, said antibodies bind to and neutralise *C. difficile* Toxin A and/or Toxin B.

For immunisation of animals, the *C. difficile* recombinant fusion protein antigens of the invention may be used as immunogens separately or in combination, either concurrently or sequentially, in order to produce antibodies specific for individual *C. difficile* toxins or combinations. For example, two or more recombinant antigens may be mixed together and used as a single immunogen. Alternatively a *C. difficile* toxin fusion protein antigen (e.g., Toxin A-derived) may be used separately as a first immunogen on a first animal group, and another *C. difficile* toxin antigen (e.g., Toxin B-derived) may be used separately on a second animal group. The antibodies produced by separate immunisation may be combined to yield an antibody composition directed against *C. difficile* toxins. Non-limiting examples of suitable adjuvants for animal/veterinary use include Freund's (complete and incomplete forms), alum (aluminium phosphate or aluminium hydroxide), saponin and its purified component Quil A.

A fourth (vaccine) aspect of the present invention provides one or more of the aforementioned fusion proteins of the invention, for use in the prevention, treatment or suppression of CDI (e.g., in a mammal such as man) Put another way, the present invention provides a method for the prevention, treatment or suppression of CDI (e.g., in a mammal such as man), said method comprising administration of a therapeutically effective amount of one or more of the aforementioned fusion proteins of the invention to a subject (e.g., a mammal such as man).

By way of example, a Toxin A-based fusion protein (any A toxinotype) may be employed alone or in combination with a Toxin B-based fusion protein (any B toxinotype). Similarly, a Toxin B-based fusion protein (any B toxinotype) may be employed alone or in combination with a Toxin A-based fusion protein (any A toxinotype). Said fusion proteins may be administered in a sequential or simultaneous manner Vaccine applications of the present invention may further include the combined use (e.g., prior, sequential or subsequent administration) of one or more antigens such as a *C. difficile* antigen (e.g., a non-Toxin antigen; or a *C. difficile* bacterium such as one that has been inactivated or attenuated), and optionally one or more nosocomial infection antigens (e.g., an antigen, notably a surface antigen, from a bacterium that causes nosocomial infection; and/or a bacterium that causes a nosocomial infection such as one that has been inactivated or attenuated). Examples of bacteria that cause nosocomial infection include one or more of: *E. coli, Klebsiella pneumoniae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example to treat a patient before said patient enters a hospital (or similar treatment facility) to help prevent hospital-acquired infection. Alternatively, said vaccine application may be administered to vulnerable patients as a matter of routine.

A related vaccine aspect of the invention provides one or more antibodies (comprising or consisting whole IgG and/or Fab and/or $F(ab')_2$ fragments) that binds to the one or more aforementioned fusion proteins of the invention, for use in the prevention, treatment or suppression of CDI (e.g., in a mammal such as man) Put another way, the present invention provides a method for the prevention, treatment or suppression of CDI (e.g., in a mammal such as man), said method comprising administration of a therapeutically effective amount of said antibody (or antibodies) to a subject (e.g., a mammal such as man).

By way of example, an anti-Toxin A-based fusion protein (any A toxinotype) antibody may be employed alone or in combination with an anti-Toxin B-based fusion protein (any B toxinotype).antibody. Similarly, an anti-Toxin B-based fusion protein (any B toxinotype) antibody may be employed alone or in combination with an anti-Toxin A-based fusion protein (any A toxinotype) antibody. Said antibodies may be administered in a sequential or simultaneous manner Vaccine applications of the present invention may further include the combined use (e.g., prior, sequential or subsequent administration) of one or more antibodies that bind to antigens such as a *C. difficile* antigen (e.g., a non-Toxin antigen; or a *C. difficile* bacterium), and optionally one or more antibodies that bind to one or more nosocomial infection antigens (e.g., an antigen, notably a surface antigen, from a bacterium that causes nosocomial infection; and/or a bacterium that causes a nosocomial infection). Examples of bacteria that cause nosocomial infection include one or more of: *E. coli, Klebsiella pneumoniae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example once a patient has entered hospital (or similar treatment facility). Alternatively, said vaccine application may be administered to patients in combination with one or more antibiotics.

In one embodiment, said antibodies have been generated by immunisation of an animal (e.g., a mammal such as man, or a non-human animal such as goat or sheep) with one or more of the aforementioned fusion proteins of the present invention.

In one embodiment, the antibodies of the present invention do not (substantially) bind to the effector domain and/or to the cysteine protease domain of a *C. difficile* Toxin A and/or Toxin B.

For the preparation of vaccines for human (or non-human animal) use, the active immunogenic ingredients (whether these be antigenic fusion protein/s of the present invention and/or corresponding antibodies of the invention that bind thereto) may be mixed with carriers or excipients, which are pharmaceutically acceptable and compatible with the active ingredient. Suitable carriers and excipients include, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

The vaccine may further comprise one or more adjuvants. One non-limiting example of an adjuvant with the scope of the invention is aluminium hydroxide. Other non-limiting examples of adjuvants include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Typically, the vaccines are prepared as injectables, either as liquid solutions or suspensions. Of course, solid forms suitable for solution in, or suspension in, liquid prior to injection may also be prepared. The preparation may also be emulsified, or the peptide encapsulated in liposomes or microcapsules.

Vaccine administration is generally by conventional routes e.g., intravenous, subcutaneous, intraperitoneal, or mucosal routes. The administration may be by parenteral injection, for example, a subcutaneous or intramuscular injection.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be particular to each subject.

The vaccine may be given in a single dose schedule, or optionally in a multiple dose schedule. A multiple dose schedule is one in which a primary course of vaccination may be with 1-6 separate doses, followed by other doses given at subsequent time intervals required to maintain and/or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFN gamma)

Additional formulations suitable for use with the present invention include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of about 0.5% to 10%, including for instance, about 1%-2%.

Fusion proteins of the invention may also have uses as ligands for use in affinity chromatography procedures. In such procedures, fusion proteins of the invention may be covalently immobilised onto a matrix, such as Sepharose, e.g., using cyanogen bromide-activated Sepharose. Such affinity columns may then be used to purify antibody from antisera or partially purified solutions of immunoglobulins by passing them through the column and then eluting the bound IgG fraction (e.g., by low pH). Almost all of the antibody in the eluted fraction will be directed against the fusion proteins of the invention, with non-specific antibodies and other proteins having been removed. These affinity purified IgG fractions have applications both as immunotherapeutics and as reagents in diagnostics. For immunotherapeutics, affinity purified antibodies enable a lower dose to be administered making adverse side effects less likely. For diagnostics, affinity purified agents often give improved specificity and fewer false positive results.

Definitions Section

*Clostridium difficile* is a species of Gram-positive bacterium of the genus *Clostridium.*

*Clostridium difficile* infection (CDI) means a bacterial infection which affects humans and animals and which results in a range of symptoms from mild self-limiting diarrhoea to life-threatening conditions such as pseudomembranous colitis and cytotoxic megacolon. In this disease, *C. difficile* replaces some of the normal gut flora and starts to produce cytotoxins which attack and damage the gut epithelium. Primary risk factors for human CDI include: receiving broad-spectrum antibiotics, being over 65 years old and being hospitalised.

*Clostridium difficile* Toxin A is a family of protein cytotoxins/enterotoxins of approximately 300 kDa in size. Toxin A has an enzyme activity within the N-terminal region which acts to disrupt the cytoskeleton of the mammalian cell causing cell death. There a number of naturally occurring variants of Toxin A within the strains of *Clostridium difficile* which are called 'toxinotypes'. The various toxinotypes of Toxin A have variations within their primary sequence of usually <10% overall. Examples of suitable Toxin A sequences include SEQ ID NOs: 1 and 3.

*Clostridium difficile* Toxin B is a family of protein cytotoxins of approximately 270 kDa in size which are similar to Toxin A but significantly more cytotoxic. Like Toxin A, Toxin B has an enzyme activity within the N-terminal region which acts to disrupt the cytoskeleton of the mammalian cell causing cell death. There are a number of naturally occurring variants of Toxin B within the strains of *C. difficile* which are called 'toxinotypes'. The various toxinotypes of Toxin B have variations within their primary sequence of up to 15% overall. Examples of suitable Toxin B sequences include SEQ ID NOs: 2 and 4.

*C. difficile* repeat units are regions within the C-terminus of Toxin A and B that contain repeating motifs which were first identified by von Eichel-Streiber and Sauerborn (1990; Gene 30: 107-113). In the case of Toxin A there are 31 short repeats and 7 long repeats with each repeat consisting of a β-hairpin followed by a loop. Toxin B consists of a similar structure but with fewer repeats. The repeat units of Toxin A are contained within residues 1850-2710 and those for Toxin B within residues 1852-2366. The repeat regions play a role in receptor binding. The receptor binding regions (i.e., that define the toxin's structural binding pockets) appear to be clustered around the long repeat regions to form 'binding modules' (see Tables 1 and 2).

Central domains of Toxin A and B are believed to play a role in translocation of the toxins into mammalian cells. The central domains of Toxin A are based on residues 543-1849 and those for Toxin B are based on residues 543-1851. Of the central domain regions of Toxins A and B, the first domain is a cysteine protease, which plays a role in the internalisation of the toxin's effector domain (which contains the glucosyl transferase activity).

Toxinotypes are often used to classify strains of *C. difficile*. Toxinotyping is based on a method which characterises the restriction patterns obtained with the toxin genes. Toxinotypes of Toxins A and B represent variants, by primary amino acid sequence, of these protein toxins. In one embodiment, the *C. difficile* toxin is selected from one of toxinotypes 0 to XV. Preferred Toxinotypes (plus example Ribotypes and Strains) are listed in the Table immediately below. The listed Toxinotypes are purely illustrative and are not intended to be limiting to the present invention

| Toxinotype | Example Ribotypes | Example Strains | Reference |
|---|---|---|---|
| 0 | 001, 106 | VPI10463 | Rupnik et al. |
| 1 | 003, 012, 102 | EX623 | (1998) |
| 2 | 103 | AC008 | J. Clinical |
| 3 | 027, 034, 075, 080 | R20291, QCD-32g58 | Microbiol. 36: 2240-2247 |
| 4 | 023, 034, 075, 080 | 55767 | |
| 5 | 066, 078 | SE881 | |
| 6 | 045, 063, 066 | 51377 | |
| 7 | 063 | 57267 | |

-continued

| Toxinotype | Example Ribotypes | Example Strains | Reference |
|---|---|---|---|
| 8 | 017, 047 | 1470 | |
| 9 | 019 | 51680 | |
| 10 | 036 | 8864 | |
| 11 | 033 | IS58, R11402 | Rupnik et al. |
| 12 | 056 | IS25 | (2001) |
| 13 | 070 | R9367 | Microbiology |
| 14 | 111 | R10870 | 147: 439-447 |
| 15 | 122 | R9385 | |

An "antibody" is used in the broadest sense and specifically covers polyclonal antibodies and antibody fragments so long as they exhibit the desired biological activity. For example, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference). Preferably, each VHC and VLC is composed of three CDRs and four FRs, arranged from amino-terminus to carboxy-terminus in the following order: 1-R1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (CIq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a toxin of *C. difficile* (e.g., Toxin A or B), e.g., a molecule in which one or more immunoglobulin chains is not full length, but which binds to a toxin. Examples of binding portions encompassed within the term antibody include (i) a Fab fragment, a monovalent fragment consisting of the VLC, VHC, CL and CH1 domains; (ii) a $F(ab')_2$ fragment, a bivalent fragment comprising two Fab fragments linked by a disulfide bridge at the hinge region; (iii) a Fc fragment consisting of the VHC and CH1 domains; (iv) a Fv fragment consisting of the VLC and VHC domains of a single arm of an antibody, (v) a dAb fragment (Ward et al., (1989) Nature 341:544-546), which consists of a VHC domain; and (vi) an isolated complementarity determining region (CDR) having sufficient framework to bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single-chain antibodies (as well as camelids) are also encompassed within the term antibody. These are obtained using conventional techniques known to those with skill in the art, and the portions are screened for utility in the same manner as are intact antibodies.

The term "fragment" means a peptide typically having at least seventy, preferably at least eighty, more preferably at least ninety percent of the consecutive amino acid sequence of the reference sequence.

The term "variant" means a peptide or peptide fragment having at least eighty, preferably at least eighty five, more preferably at least ninety percent amino acid sequence homology with a *C. difficile* toxin polypeptide. For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, (1994) Nucleic Acids Research 22(22):4673-4680; and iterative refinement, see, e.g., Osamu Gotoh, Significant Improvement in Accuracy of Multiple Protein. Sequence Alignments by Iterative Refinement as Assessed by Reference to Structural Alignments, (1996) J. Mol. Biol. 264(4):823-838. Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, (1992) CABIOS 8(5):501-509; Gibbs sampling, see, e.g., C. E. Lawrence et al., Detecting Subtle Sequence Signals: A Gibbs Sampling Strategy for Multiple Alignment, (1993) Science 262(5131):208-214; Align-M, see, e.g., Ivo Van WaIle et al., Align-M—A New Algorithm for Multiple Alignment of Highly Divergent Sequences, (2004) Bioinformatics 20(9):1428-1435.

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment scores for determining sequence identity (SEQ ID NO: 82)

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 15 | | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{\text{length of the longer sequence plus the number of gaps introduced into the longer sequence in order to align the two sequences]}} x100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
lysine
histidine
Acidic: glutamic acid
aspartic acid
Polar: glutamine
asparagine
Hydrophobic: leucine
isoleucine
valine
Aromatic: phenylalanine
tryptophan
tyrosine
Small: glycine
alanine
serine
threonine
methionine In addition to the 20 standard amino acids, non-standard amino acids (such as 4-hydroxyproline, 6-N-methyl lysine, 2-aminoisobutyric acid, isovaline and a-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g., the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenised polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Toxin-neutralising means the capacity of a substance to prevent the cytotoxic action of either Toxin A or B on a mammalian cell. In assays for toxin-neutralising activity, a fixed amount of toxin is mixed with various concentrations of a neutralising substance (e.g., an antibody) and the mixture applied to and incubated with a mammalian cell line (e.g., Vero cells) for a fixed time. The dilution of the substance (antibody) that completely protects the cells from the cytotoxic effects of either Toxin A or B (evident by cell rounding) may be defined as the neutralising titre.

EXAMPLES

Figure 1:
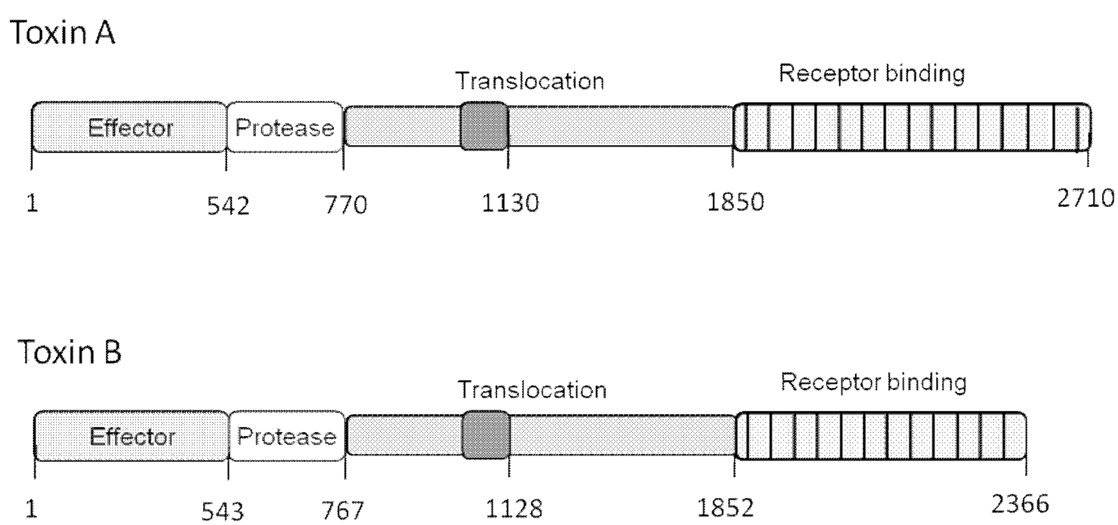
FIG. 1 illustrates the structures of *C. difficile* Toxins A and B showing amino acid residues at the various domain boundaries.

Example 1—Cloning and Expression of Antigens Derived from Toxins A and B

Genes encoding these peptides may be made commercially with codon bias for any desired expression host (e.g., *E. coli, Pichia pastoris*). Peptides are expressed from these genes using standard molecular biology methods (e.g., Sambrook et al. 1989, Molecular Cloning a Laboratory Manual, Second Edition, Cold Spring Harbor Laboratory Press, Cold Spring Harbor, New York). One convenient method of cloning is the Gateway® system (Invitrogen) which allow genetic constructs to be assembled in a modular fashion.

Protocol 1: The Gateway LR Recombination Reaction—a General Protocol

Materials: Antigen gene (Toxin A or B)) entry clones were synthesised by Entelechon. Gateway® LR Clonase™ II Enzyme Mix was purchased from Invitrogen. Gateway® Nova pET Destination vectors were purchased from Calbiochem Nova, part of Merck Chemicals Ltd.

Toxin A or B entry clone (1 μl), destination vector (1 μl) and TE buffer (6 μl) were mixed at room temperature in a 1.5 ml microcentrifuge tube. LR Clonase™ II was placed on ice for two minutes and mixed briefly with vortexing (2×2 s). The clonase enzyme (2 μl) was added to the microcentrifuge tube and the components mixed with gentle pipetting. Recombinations were incubated at 25° C. for 1 hour. Proteinase K solution (1 μl, 2 μg/μl) was added and the reactions incubated at 37° C. for 10 minutes. The resultant solution (1 μl) was used to transform chemically competent *E. coli.*

Protocol 2: Transformation of Chemically Competent Cells—a General Protocol

Materials: OneShot® BL21 Star™ (DE3) and One Shot® TOP10 chemically competent *E. coli* and SOC media were purchased from Invitrogen. Ampicillin was purchased from Sigma Aldrich.

LR recombination reaction or plasmid DNA (1 μl) was pipetted into an aliquot (50 μl) of BL21 Star™ or TOP10 chemically competent *E. coli*. The mixture was incubated on ice for 30 minutes and subsequently heat shocked in a water bath at 42° C. for 30 seconds. The cell aliquot was returned to the ice and SOC media (250 μl) added. Transformations were maintained in SOC media at 37° C. for 1 hour with orbital shaking (180 rpm). Transformation culture (100-200 μl) was plated out onto LB agar supplemented with ampicillin (100 μg/ml). The plates were incubated at 37° C. for 15 minutes, inverted and maintained at the same temperature overnight.

Example 2—Purification of Antigens of the Invention—Expression and Purification of *C. difficile* Toxin B Fragment TxB3

Toxin B-derived antigen TxB3(-h) (e.g., SEQ ID NO: 9) was expressed as a thioredoxin fusion protein (SEQ ID NO: 27).

An N-his$_6$-thioredoxin fusion of TxB3 was expressed in BL21 Star™ (DE3) *E. coli* harbouring plasmid pDest59TxB3. LB media (3×20 ml) supplemented with 100 μg/ml ampicillin and 0.5% glucose was inoculated from a glycerol cell stock (cell culture<$OD_{600}$ 1 [500 μl]+glycerol [125 μl]). Cultures were maintained at 37° C. for 6-7 hours with orbital shaking (180 rpm). Each culture was used to inoculate LB media (100 ml) supplemented with 100 μg/ml ampicillin and 0.5% glucose. Cultures were maintained at 37° C. for 1 hour with orbital shaking (180 rpm). Terrific Broth (3×1 L) supplemented with 100 μg/ml ampicillin and 0.1% glucose was inoculated with the LB culture (100 ml per litre) and maintained at 37° C. as before to an absorbance at 600 nm of 0.5. Expression was induced with the addition of IPTG to a final concentration of 1 mM and the cultures maintained at 16° C. overnight with orbital shaking (180 rpm). Cells were harvested by centrifugation for 30 minutes (3000 rpm, Sorvall RC3BP centrifuge, rotor #H6000A), resuspended in low imidazole buffer (100 ml, pH 7.4, 50 mM HEPES, 500 mM sodium chloride, 20 mM imidazole) and frozen at −80° C.

(i) Nickel Affinity Purification of the Thioredoxin TxB3 Fusion Protein

Cell paste was thawed at room temperature and then on ice until liquefied. Cells were disrupted with sonication (10 cycles of 30 s ON and 30 s OFF) and the resultant lysate cleared by centrifugation for 30 minutes (14,000 rpm, Sorvall RC5C centrifuge, rotor #SS-34). Cleared lysate was applied to fast flow chelating sepharose charged with nickel ions (40 ml bed volume) at a flow rate of 1 ml/min. The column was washed with low imidazole buffer (pH 7.4, 50 mM HEPES, 500 mM sodium chloride, 20 mM imidazole) until the absorbance of the flow through at 280 nM returned to near baseline levels. Bound material was eluted with sequential steps to 15, 25 and 70% high imidazole buffer (pH 7.4, 50 mM HEPES, 500 mM sodium chloride, 500 mM imidazole). Material eluted at 70% high imidazole buffer was pooled and dialysed into thrombin cleavage buffer (20 mM Tris-HCl pH 8.4, 150 mM sodium chloride, 2.5 mM calcium chloride) overnight.

(ii) Thrombin Digestion of the Thioredoxin TxB3 Fusion Protein

Human thrombin (Novagen, 1 U per mg of total protein) was added to the pooled nickel column fractions which had been dialysed into thrombin cleavage buffer. The digest was incubated at 25° C. for 4 hours and frozen at −80° C. to prevent continued cleavage.

(iii) Nickel Affinity Purification of TxB3

Figure 2:
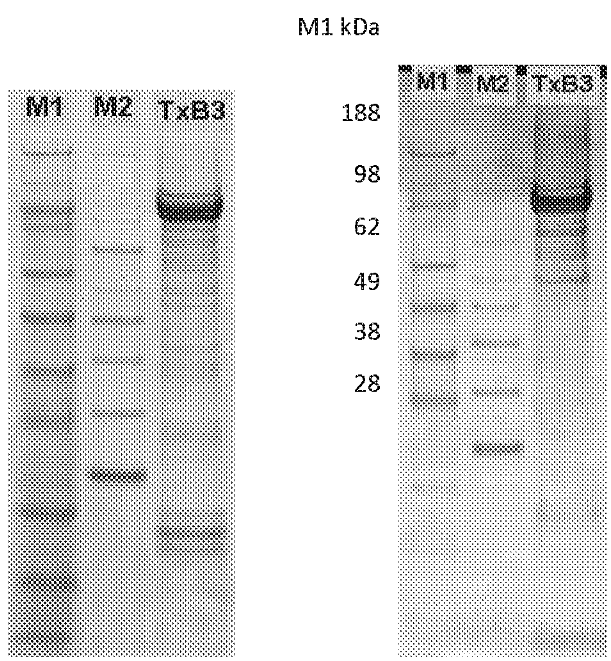
FIG. 2 illustrates TxB3 purification. The left-hand Figure shows a 4-12% SDS-PAGE analysis of TxB3. M1=SeeBlue® Plus2 Pre-Stained Standard, M2=MagicMark™ XP Standard. The right-hand Figure shows a Western blot analysis of TxB3 with ovine anti-TcdB polyclonal antibodies. M1 and M2 are as described for the left-hand Figure.

The thrombin digest was thawed on ice and p-Aminobenzamidine resin added (0.1 ml drained resin per 6U of thrombin). The mixture was gently rocked over ice for 30 minutes and the resin filtered off. The cleared filtrate was passed over fast flow chelating sepharose charge with nickel ions (6 ml bed volume) at a flow rate of 1 ml/min and the flow through pooled and dialysed into storage buffer (pH 7.4, 50 mM HEPES, 150 mM sodium chloride). The solution was sterile filtered into 1 ml aliquots. The total protein obtained was 10.5 mg, which was estimated to be 55% TxB3. Protein was also analysed by Western blotting with ovine anti-TcdB polyclonal antibodies (FIG. 2).

Example 3—Purification of Antigens of the Invention—Expression and Purification of *C. difficile* Toxin B Fragment TxB4

Large Scale Expression of the Nus TxB4 Fusion Protein

A bead from a −80° C. stock of BL21 Star™ (DE3) *E. coli* harbouring plasmid pDest57TxB4His was streaked onto L-agar supplemented with 100 μg/ml ampicillin and incubated at 37° C. overnight. A single colony was used to inoculate 2YT media (100 ml) supplemented with 100 μg/ml ampicillin and 0.5% glucose. The culture was maintained at 37° C. with orbital shaking (180 rpm) to an absorbance of 0.6 at 600 nm and used as a 5% inoculum for Terrific Broth (2×1 L) supplemented with 100 μg/ml ampicillin and 0.5% glucose. Cultures were maintained as before to an absorbance of 0.6 at 600 nm and the temperature lowered to 16° C. Protein expression was induced by the addition of IPTG to a final concentration of 1 mM following thermal equilibration and the culture maintained overnight. Cells were harvested by centrifugation for 30 minutes (3000 rpm, Sorvall RC3BP centrifuge, rotor #H6000A), resuspended in low imidazole buffer (1:4 cell paste to buffer w/v, 50 mM HEPES pH 7.4, 500 mM sodium chloride, 20 mM imidazole) and frozen at −80° C.

Nickel Affinity Purification of the Nus TxB4 Fusion Protein

Cell paste was thawed at room temperature and then on ice until liquefied. Cells were disrupted with sonication (15 cycles of 30 s ON and 30 s OFF) and the resultant lysate cleared by centrifugation for 30 minutes at 4° C. (16,000 rpm, Sorvall RC5C centrifuge, rotor #SS-34). Cleared lysate was applied to fast flow chelating sepharose charged with nickel ions (40 ml bed volume) at a flow rate of 2 ml/min. The column was washed with low imidazole buffer (pH 7.4, 50 mM HEPES, 500 mM sodium chloride, 20 mM imidazole) until the absorbance of the flow through at 280 nm returned to near baseline levels. Bound material was eluted with a step to 50% high imidazole buffer (pH 7.4, 50 mM HEPES, 500 mM sodium chloride, 500 mM imidazole). Material eluted from the column was analysed by SDS-PAGE and selected fractions pooled. Protein concentration was determined from the absorbance at 280 nm.

Thrombin Digestion of the Nus TxB4 Fusion Protein

To each 10 μg of protein, 5 μl of thrombin digest buffer (200 mM Tris-HCl pH 8.4, 1.5 M NaCl, 25 mM $CaCl_2$), 1 μl of Human thrombin (Novagen) diluted 200 fold in thrombin dilution buffer (50 mM sodium citrate, pH 6.5, 200 mM NaCl, 0.1% PEG-8000, 50% glycerol) and water to a volume of 50 μl were added. The protein was digested overnight at room temperature and dialysed into low imidazole buffer at 4° ° C.

Nickel Affinity Purification of TxB4

Figure 3:
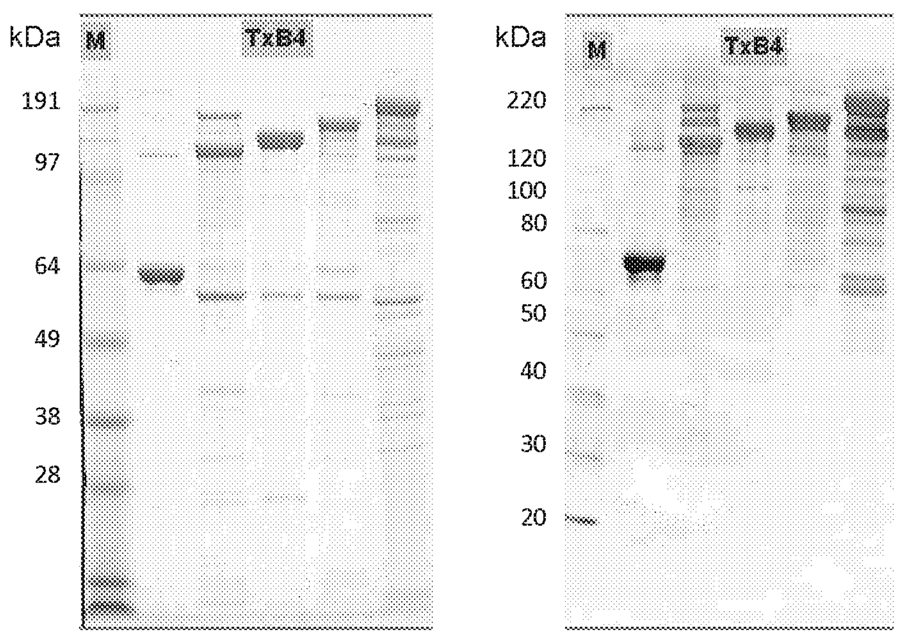
FIG. 3 illustrates TxB4 purification. The left-hand Figure shows a 4-12% SDS-PAGE analysis of TxB4. M=SeeBlue® Plus2 Pre-Stained Standard. The right-hand Figure shows a Western blot analysis of TxB4 with ovine anti-TcdB polyclonal antibodies, M=MagicMark™ XP Standard.

TxB4 in low imidazole buffer was applied to fast flow chelating sepharose charged with nickel ions (40 ml bed volume) at a flow rate of 3 ml/min. The column was washed with low imidazole buffer until the absorbance of the flow through at 280 nm returned to near baseline levels. The column was washed with 80 mM imidazole, protein eluting after the resultant initial peak in UV absorbance (280 nm) was collected and dialysed into storage buffer (50 mM HEPES pH 7.4, 150 mM sodium chloride). Protein was analysed by SDS-PAGE and Western blotting with ovine anti-TcdB polyclonal antibodies (FIG. 3).

Example 4—Expression and Purification of *C. difficile* Toxin B Fragment TxB5 (Residues 544-2366 of Toxin B)

Large Scale Expression of the Nus TxB5 Fusion Protein

An N-$his_6$-Nus fusion of TxB5 was expressed in BL21 Star™ (DE3) *E. coli* harbouring plasmid pDest57TxB5. An overnight culture in LB media supplemented with 100 μg/ml ampicillin was used as a 3% inoculum for Terrific Broth (3 L) supplemented with 100 μg/ml ampicillin. Cultures were maintained at 37° C. to an absorbance at 600 nm of 0.6 with orbital shaking (180 rpm). Expression was induced with the addition of IPTG to a final concentration of 1 mM and the cultures maintained at 16° C. overnight with orbital shaking (180 rpm). Cells (25 g) were harvested by centrifugation for 30 minutes (3000 rpm, Sorvall RC3BP centrifuge, rotor #H6000A) and resuspended in low imidazole buffer (250 ml, pH 7.4, 50 mM HEPES, 500 mM sodium chloride, 20 mM imidazole).

Nickel Affinity Purification of the Nus TxB5 Fusion Protein

Lysozyme (10 mg) was added to the resuspended cells and the mixture stirred for 15 minutes. Cells were disrupted with sonication (10 cycles of 30 s ON and 30 s OFF) and the resultant lysate cleared by centrifugation for 30 minutes (14,000 rpm, Sorvall RC5C centrifuge, rotor #SS-34). Half of the cleared lysate was applied to fast flow chelating sepharose charged with nickel ions (40 ml bed volume) at a flow rate of 2 ml/min. The column was washed with low imidazole buffer until the UV absorbance of the flow through at 280 nm returned to near baseline levels. Protein, including Nus TxB5, was eluted with a step to 38% (200 mM imidazole) high imidazole buffer (pH 7.4, 50 mM HEPES, 500 mM sodium chloride, 500 mM imidazole). The second half of the lysate was processed in the same manner and the pooled eluted protein dialysed overnight into high salt HIC buffer (pH 7.4, 50 mM HEPES, 750 mM ammonium sulphate).

Butyl-s Hydrophobic Interaction Chromatography Purification of Nus TxB5

Half of the pooled protein solution in high salt HIC buffer was applied to a column containing butyl-s-sepharose 6 fast flow resin (9 ml bed volume). The column was washed with high salt HIC buffer (pH 7.4, 50 mM HEPES, 750 mM ammonium sulphate) until the UV absorbance of the flow through at 280 nm returned to near baseline levels. Protein was eluted from the column with a step to 100% low salt HIC buffer ((pH 7.4, 50 mM HEPES). The other half of the protein from the first nickel column was purified in the same manner. The eluted protein was pooled in preparation for digestion with thrombin.

Thrombin Digestion of the Nus TxB5 Fusion Protein

Pooled protein from the HIC column (69 mg, 30 ml) was added to a solution containing 10× thrombin cleavage buffer (15 ml, 200 mM Tris-HCl pH 8.4, 1.5 M sodium chloride, 25 mM calcium chloride), deionised water (105 ml) and human thrombin (Novagen, 40 U). The solution was incubated at room temperature for 4 hours and PMSF added to a final concentration of 1 mM. The resultant protein including the TxB5 was dialysed into high salt HIC buffer.

Butyl-s Hydrophobic Interaction Chromatography Purification of TxB5

The TxB5 from the thrombin digest was purified in two batches. Each batch was applied in high salt HIC buffer (pH 7.4, 50 mM HEPES, 750 mM ammonium sulphate) to a column containing butyl-s-sepharose 6 fast flow resin (9 ml bed volume) at a flow rate of 1 ml/min. The column was washed with high salt HIC buffer until the UV absorbance of the flow through at 280 nm returned to near baseline levels. Protein was eluted from the column with a step to 100% low salt HIC buffer (pH 7.4, 50 mM HEPES). The eluted material was dialysed against buffer (pH 7.4, 50 mM HEPES) overnight.

Q Sepharose Ion Exchange Chromatography Purification of TxB5

Figure 4:
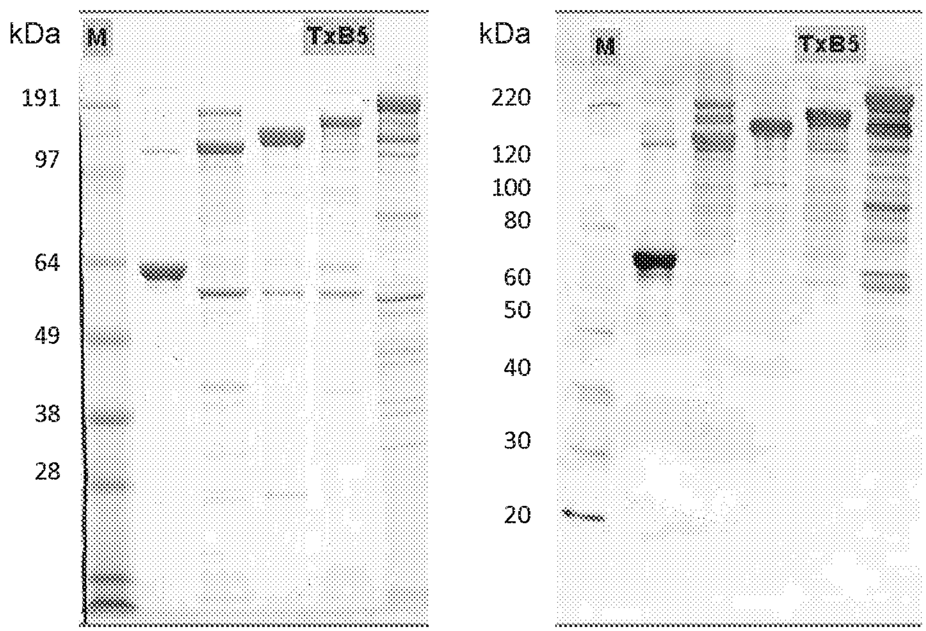
FIG. 4 illustrates TxB5 purification. The left-hand Figure shows a 4-12% SDS-PAGE analysis of TxB5. M=SeeBlue® Plus2 Pre-Stained Standard. The right-hand Figure shows a Western blot analysis of TxB5 with ovine anti-TcdB polyclonal antibodies, M=MagicMark™ XP Standard.

The TxB5 in buffer (pH 7.4, 50 mM HEPES) was run through a column containing Q sepharose fast flow resin (5 ml bed volume) at a flow rate of 1 ml/min. The flow through was pooled and dialysed into storage buffer (pH 7.4, 50 mM HEPES, 150 mM sodium chloride). Approximately 20 mg of protein was produced, of this 60% was TxB5 based on SDS-PAGE analysis. The protein was frozen in 1 ml aliquots at −80° C. Protein was analysed by SDS-PAGE and Western blotting with ovine anti-TcdB polyclonal antibodies (FIG. 4).

Example 5—Expression and Purification of *C. difficile* Toxin A Fragment TxA4 (Residues 770-2710 of Toxin A)

Expression

L-broth (100 ml) supplemented with 50 μg/ml kanamycin and 0.2% glucose was inoculated with a scrape from a glycerol freeze (BL21 (DE3) *E. coli* harbouring plasmid pET28a$His_6$TrxHRV3CαNaturalTxA4) and maintained overnight at 30° C. and 180 rpm. The overnight culture was used as a 2% inoculum for Terrific Broth (4×0.5 L in 2 L unbaffled flasks) supplemented with 50 μg/ml kanamycin and 0.2% glucose. Cultures were maintained at 37° C. with orbital shaking (180 rpm) to an absorbance at 600 nm of 0.6. The temperature of the cultures was reduced to 16° C. and protein expression induced with the addition of 1 mM IPTG. The culture was maintained overnight at 16° C. with orbital shaking as before. Cell paste (23 g) was harvested by centrifugation (Sorvall RC3BP centrifuge, H6000A rotor, 4000 g, 20 minutes). The paste was recovered from the centrifuge pots by resuspension in low imidazole buffer (pH 7.5, 50 mM Hepes, 0.5 M sodium chloride, 20 mM Imidazole) and stored at −80° C.

Immobilised Nickel Affinity Purification of the TxA4 Precursor

Cells (23 g) resuspended with 85 ml of low imidazole buffer (pH7.5, 50 mM Hepes, 0.5 M NaCl 20 mM imidazole) was subjected to lysis using sonication. The lysate was cleared by centrifugation (Sorvall RC5C centrifuge, SS-34 rotor, 20,000 g, 20 minutes) and applied to a 20 ml nickel column (Ø26 mm) at a flow rate of 1.5 ml/min. The column was washed with ten column volumes of low imidazole buffer and bound protein eluted using a five column volume gradient to 100% high imidazole buffer (pH 7.5, 50 mM Hepes, 0.5 M NaCl, 0.5 M imidazole). Fractions were analysed on 4-12% NuPAGE Bis-Tris polyacrylamide gels with coomassie staining.

Cleavage of the Fusion Partner and $His_6$-Tag

The purest fractions were pooled and dialysed against HRV3C cleavage buffer (2 L, pH 7.5, 20 mM Tris-HCl, 0.5 M NaCl) overnight at 4° C. HRV3C protease (10 U per mg of full length target protein) was added to the solution and incubated at 20° C. for five hours followed by 4° C. overnight.

Immobilised Nickel Affinity Purification of Post Cleavage TxA4

Figure 5:
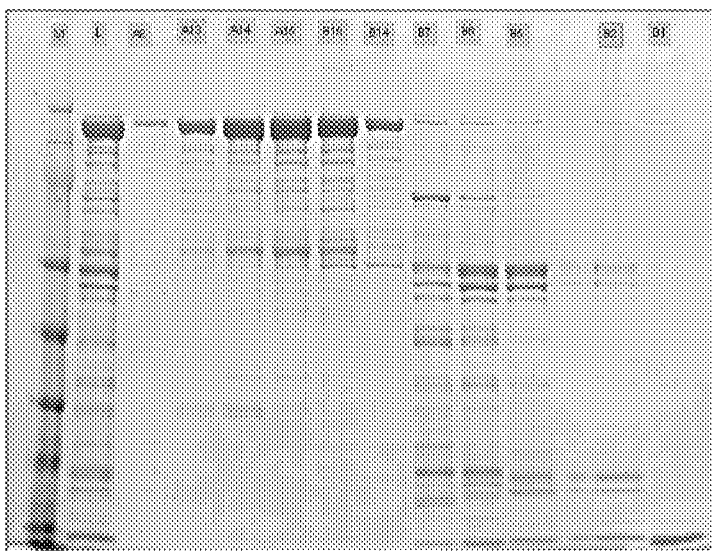
FIG. 5 illustrates TxA4 purification and SDS-PAGE analysis of the nickel affinity purification of HRV3C protease treated TxA4. M=Molecular weight markers, L=column load, A8=column flow-through. Fractions A14-B14 showed the purified TxA4.

The protein solution (pH 7.5 20 mM Tris-HCl, 0.5 M NaCl) was passed over a 20 ml nickel column (Ø26 mm) at a flow rate of 1.5 ml/min. Some protein was seen to elute in the flow through as judged by the UV absorbance. The column was given a short wash with the HRV3C cleavage buffer and the TxA4 eluted with 5% high imidazole buffer (pH7.5, 50 mM Hepes, 0.5 M NaCl, 0.5 M imidazole) at an imidazole concentration of 25 mM. The remaining proteins were eluted from the column with a four column volume gradient to 100% high imidazole buffer. The purest fractions were pooled and dialysed into storage buffer (pH 7.5, 50 mM Hepes, 0.5 M NaCl). Fractions from the final purification column are shown in FIG. 5.

Example 6—Expression and Purification of *C. difficile* Toxin A Fragment TxA4 Truncated (Residues 770-2389 of Toxin A)

Expression

L-Broth (100 ml) supplemented with 100 μg/ml ampicillin and 0.5% glucose was inoculated with a colony (harbouring pET59His6TRXtcsαnaturalTxA4truncate) from an overnight growth on a L-agar plate supplemented with 100 μg/ml ampicillin and maintained overnight at 37° C. and 180 rpm. This was used as an inoculum for Terrific Broth (6×1000 mls in 2000 ml unbaffled flasks) supplemented with 100 μg/ml ampicillin and 0.5% glucose. Cultures were maintained at 37° C. with orbital shaking (180 rpm) to an absorbance at 600 nm of 0.6. The temperature of the cultures was reduced to 16° C. and protein expression induced with the addition of IPTG to a final concentration of 1 mM. The culture was maintained overnight at 16° C. with orbital shaking as before. Cell paste was harvested by centrifugation (Sorvall RC3BP centrifuge, H6000A rotor, 4000 g, 30 minutes). The paste was recovered from the centrifuge pots by re-suspension in Hepes buffer (50 mM Hepes pH 7.4, 0.5 M sodium chloride) and stored at −20° C.

Immobilised Nickel Affinity Purification of the TxA4 Truncate Precursor

Cells (44 g) re-suspended with 180 ml of Hepes buffer (50 mM Hepes pH 7.4, 500 mM NaCl) were subject to lysis using sonication. The lysate was clarified by centrifugation at 4000 rpm for 20 minutes (Heraeus Multifuge). The supernatant was retained and applied to a 64 ml Zinc Sepharose column (XK26×12) at a flow rate of 5 ml/minute. The column was washed until the absorbance at 280 nm was reduced to the baseline. The bound protein was eluted using a gradient of 0-250 mM imidazole in 50 mM Hepes pH 7.4, 500 mM sodium chloride. The fractions were analysed on 4-12% NuPAGE® Bis-Tris polyacrylamide gels with coomassie staining.

Cleavage of the Fusion Partner and $His_6$-Tag

The purest fractions were pooled and dialysed against thrombin cleavage buffer (20 mM Tris/HCl pH 8.4+150 mM NaCl+2.5 mM $CaCl_2$) overnight at +4° C. Restriction grade thrombin (Novagen) was added at 1:2000 wt:wt with respect to the target protein. The mixture was incubated at room temperature overnight.

Immobilised Zinc Affinity Purification of Post Cleavage TxA4 Truncate

The protein solution (in 50 mM Hepes pH 7.4, 500 mM sodium chloride) was passed over a 24 ml zinc column (XK16×12) at a flow rate of 2 ml/minute. The column was washed with equilibration buffer (50 mM Hepes pH 7.4, 500 mM sodium chloride) until the absorbance at 280 nm was reduced to the baseline. The bound protein was eluted using a gradient of 0-250 mM imidazole in 50 mM Hepes pH 7.4, 500 mM sodium chloride.

Example 7—Formulation of Antigens of the Invention for Immunisation of Animals

Purified *C. difficile* antigens at a concentration of between 0.5-2 mg/ml (nominally 1 mg/mi) were dialysed against a suitable buffer (e.g., 10 mM Hepes buffer pH 7.4 containing 150 mM NaCl) and then formaldehyde added to a final concentration of 0.2% and incubated for up to 7 days at 35° C. After incubation, the formaldehyde may optionally be removed by dialysis against a suitable buffer, e.g., phosphate buffered saline.

For sheep, 2 ml of buffer solution containing between 10 and 500 μg of the above *C. difficile* antigen is mixed with 2.6 ml of Freund's adjuvant to form an emulsion. Mixing with the adjuvant is carried out for several minutes to ensure a stable emulsion. The complete form of the adjuvant is used for the primary immunisation and incomplete Freund's adjuvant for all subsequent boosts.

Example 8—Generation of Antibodies to Antigens of the Invention

A number of conventional factors are taken into consideration during the preparation of antiserum in order to achieve the optimal humoral antibody response. These include: breed of animal; choice of adjuvant; number and location of immunisation sites; quantity of immunogen; and number of and interval between doses. With conventional optimisation of these parameters is routine to obtain specific antibody levels in excess of 6 g/litre of serum.

For sheep, an emulsion of the antigen with Freund's adjuvant was prepared as described as in Example 7. The complete form of the adjuvant is used for the primary immunisation and incomplete Freund's adjuvant for all subsequent boosts. About 4.2 ml of the antigen/adjuvant mixture was used to immunise each sheep by i.m. injection and spread across 6 sites including the neck and all the upper limbs. This was repeated every 28 days. Blood samples were taken 14 days after each immunisation.

For comparison of the toxin-neutralising immune response to the different antigens, 3 sheep were used per antigen. They were immunised as above using an identical protocol and the same protein dose per immunisation.

Example 9—Assessment of the Neutralising Efficacy of Antisera to Toxins Using the In Vitro Cell Assay The toxin neutralizing activity of the antisera against *C. difficile* Toxins was measured by cytotoxicity assays using Vero cells. A fixed amount of either purified *C. difficile* Toxin A or Toxin B was mixed with various dilutions of the antibodies, incubated for 30 min at 37° C. and then applied to Vero cells growing on 96-well tissue culture plates. Both Toxin A and B possess cytotoxic activity which results in a characteristic rounding of the Vero cells over a period of 24-72 h. In the presence of neutralising antibodies this activity is inhibited and the neutralising strength of an antibody preparation may be assessed by the dilution required to neutralise the effect of a designated quantity of either Toxin A or B.

Data demonstrating the neutralising activity of ovine antibody to various recombinant *C. difficile* Toxin B antigens are shown in Tables 3-6. In these experiments, various dilutions of ovine antibody were mixed with Toxin B at a final concentration of 0.5 ng/ml and incubated for 30 min at 37° C. and then applied to Vero cells as above and incubated at 37° and monitored over a period of 24-72 h. The antibody dilutions which completely protect the cells against the cytotoxic effects of the Toxin B were calculated. Similar data for Toxin A-derived antigens are shown in tables 7-10.

Collectively, the data in Tables 3-10 show the superior capacity of fusion proteins of the invention to elicit a toxin-neutralising immune response compared to fragments containing just the repeat domains of either Toxin A or B.

Example 10—Assessment of the In Vivo Efficacy of Antiserum Generated Using Recombinant Antigens of the Invention for Treating CDI To demonstrate the efficacy of the antisera generated, using recombinant antigens, to treat CDI in vivo, Syrian hamsters are passively immunised with antibodies which have neutralising activity against one or more of the toxins of *C. difficile*. For assessing the efficacy of a treatment formulation, hamsters will be given antibody either intravenously or by the intraperitoneal route at various times from 6 hours post-challenge to 240 hours post challenge with *C. difficile*

Prior to passively immunisation hamsters are administered a broad spectrum antibiotic (e.g., clindamycin) and 12-72 h later challenged with *C. difficile* spores by mouth. Animals are then monitored for up to 15 days for symptoms of *C. difficile*-associated disease. Control, non-immunised animals develop signs of the disease (e.g., diarrhoea, swollen abdomen, lethargy, ruffled fur) while those treated with ovine antibody appear normal.

Example 11—Vaccination by Peptide/Peptide Fragments of the Invention

A vaccine, represented by a peptide/peptide fragment of the invention is prepared by current Good Manufacturing Practice. Using such practices, peptides/peptide fragments of the invention may be bound to an adjuvant of aluminium hydroxide which is commercially available (e.g., Alhydrogel®). The vaccine would normally contain a combination of antigens of the invention derived from Toxin A and Toxin B but could also contain either Toxin A or B antigens. The vaccine may also contain Toxin A and B antigens in combination with other antigens of bacterial or viral origin.

Purified *C. difficile* Toxin A and/or Toxin B antigen of the invention may be treated with formaldehyde at a final concentration of 0.2% and incubated for up to 24 hours at 35° C. (as described in Example 7).

In addition to the antigens of the invention, a typical vaccine composition comprises:

A) A buffer (e.g., Hepes buffer between 5 and 20 mM and pH between 7.0 and 7.5;
B) A salt component to make the vaccine physiologically isotonic (e.g., between 100 and 150 mM NaCl);
C) An adjuvant (e.g., aluminium hydroxide at a final aluminium concentration of between 100 and 700 μg per vaccine dose); and
D) A preservative (e.g., Thiomersal at 0.01% or formaldehyde at 0.01%).

Such vaccine compositions are administered to humans by a variety of different immunisation regimens, such as:

1. A single dose (e.g., 20 μg adsorbed fragment of the invention) in 0.5 ml administered sub-cutaneously.
2. Two doses (e.g., of 10 μg adsorbed fragment of the invention) in 0.5 mls administered at 0 and 4 weeks.
3. 3. Three doses (e.g., of 10 μg adsorbed fragment of the invention) in 0.5 mls administered at 0, 2 and 12 weeks.

These vaccination regimens confer levels of protection against exposure to the homologous serotypes of *C. difficile* toxins Example 12—Affinity Purification of IgG Using Immobilised Constructs of the Invention Preparation of the Affinity Chromatography Medium The construct of the invention to be immobilised is dialysed against a suitable coupling buffer e.g., 0.1 M $NaHCO_3$ pH 8.3 containing 0.5 M NaCl. Approximately 5 ml of protein solution at 1-3 mg/ml is added per ml of CNBr-activated Sepharose 4B powder. The mixture is rotated end-over end for 1 h at room temperature or overnight at 4° C. Other gentle stirring methods may be employed. Excess ligand is then wash away excess with at least 5 medium (gel) volumes of coupling buffer. Any remaining active groups and then blocked. The medium is transferred to 0.1 M Tris-HCl buffer, pH 8.0 or 1 M ethanolamine, pH 8.0 and incubated 2 hours at room temperature. The gel is then washed with at least three cycles of alternating pH (at least 5 medium volumes of each buffer). Each cycle should consist of a wash with 0.1 M acetic acid/sodium acetate, pH 4.0 containing 0.5 M NaCl followed by a wash with. 0.1 M Tris-HCl, pH 8 containing 0.5 M NaCl. After washing the gel is transferred to a suitable storage buffer (e.g., 50 mM HEPES pH 7.4 containing 0.15 M NaCl and stored at 4° C. until use Purification of IgG Affinity columns are prepared as above using antigens of the invention derived from either Toxin A or B. For purification of antibodies to Toxin B, a construct such as TxB4 (residues 767-2366) could be used. For purification of antibodies to Toxin A, a construct such as TxA4 (residues 770-2710) could be used. For affinity purification of antibodies which bind toxin B, serum which contains antibodies to Toxin B is diluted 1:1 with a suitable buffer (e.g. 20 mM HEPES pH 7.4 buffer containing 0.5M NaCl) and the mixture applied to column containing immobilised TxB4 packed in a suitable column (2-6 ml mixture per ml of gel). After the unbound fraction (which contains serum albumin and non-specific IgG) is washed off with at least 10 column volumes of 20 mM HEPES pH 7.4 buffer containing 0.5M NaCl buffer, the bound fraction is eluted from the column with 5 column volumes of elution buffer (e.g., 100 mM glycine buffer, pH 2.5). The eluted fractions containing the IgG are then immediately neutralised to approximately pH 7.0 with of 1 M Tris-HCl pH 8.0. These fractions, which contain the IgG which binds Toxin B, are then dialysed against 50 mM HEPES pH 7.4 containing 0.15 m NaCl and stored frozen until required Affinity purified IgG fractions which bind and neutralises either Toxin A or B may be used as therapeutic agents to either treatment of prevent CDI. They may also be used in assay systems such as enzyme-linked immunosorbant assay (ELISA) for the detection of Toxins A or B. In such diagnostic systems, affinity purified antibodies may provide assays of higher sensitivity and with reduced background interference.

FIGURES AND TABLES

TABLE 1

| Toxin A Receptor-Binding Repeat Modules | |
|---|---|
| Toxin A Receptor-Binding Modules | Amino acid Sequence (Long Repeat regions shown in bold) |
| Module 1 LR = SEQ ID NO: 60 | **GVFKGPDGFEYFAPANTQNNNIEGQAIVYQS** |
| Module 1 (residues 1851-2007 = SEQ ID NO: 61) | VTGWQTINGKKYYFDINTGAALTSYKIINGKHF<br>YFNNDGVMQL**GVFKGPDGFEYFAPANTQNN**<br>**NIEGQAIVYQS**KFLTLNGKKYYFDNNSKAVTG<br>WRIINNEKYYFNPNNAIAAVGLQVIDNNKYYF<br>NPDTAIISKGWQTVNGSRYYFDTDTAIAFN |
| Module 2 LR = SEQ ID NO: 62 | **GVFSTSNGFEYFAPANTYNNNIEGQAIVYQS** |
| Module 2 (residues 2008-2141 = SEQ ID NO: 63) | GYKTIDGKHFYFDSDCVVKI**GVFSTSNGFEYF**<br>**APANTYNNNIEGQAIVYQS**KFLTLNGKKYYFD<br>NNSKAVTGLQTIDSKKYYFNTNTAEAATGWQT<br>IDGKKYYFNTNTAEAATGWQTIDGKKYYFNTN<br>TAIAST |
| Module 3 LR = SEQ ID NO: 64) | **GVFKGPNGFEYFAPANTDANNIEGQAILYQN** |
| Module 3 (residues 2142-2253 = SEQ ID NO: 65) | GYTIINGKHFYFNTDGIMQI**GVFKGPNGFEYF**<br>**APANTDANNIEGQAILYQN**EFLTLNGKKYYFG<br>SDSKAVTGWRIINNKKYYFNPNNAIAAIHLCTI<br>NNDKYYFSYDGILQN |
| Module 4 LR = SEQ ID NO: 66) | **GVFKGPNGFEYFAPANTHNNNIEGQAIVYQN** |
| Module 4 (residues 2254-2389 = SEQ ID NO: 67) | GYITIERNNFYFDANNESKMVT**GVFKGPNGFE**<br>**YFAPANTHNNNIEGQAIVYQN**KFLTLNGKKY<br>YFDNDSKAVTGWQTIDGKKYYFNLNTAEAAT<br>GWQTIDGKKYYFNLNTAEAATGWQTIDGKKY<br>YFNTNTFIAST |
| Module 5 LR = SEQ ID NO: 68) | **GVFKGPNGFEYFAPANTDANNIEGQAILYQN** |
| Module 5 (residues 2390-2502 = SEQ ID NO: 69) | GYTSINGKHFYFNTDGIMQI**GVFKGPNGFEYF**<br>**APANTDANNIEGQAILYQN**KFLTLNGKKYYF<br>GSDSKAVTGLRTIDGKKYYFNTNTAVAVTGW<br>QTINGKKYYFNTNTSIAST |
| Module 6 LR = SEQ ID NO: 70) | **GVFKGPDGFEYFAPANTDANNIEGQAIRYQN** |
| Module 6 (residues 2503-2594 = SEQ ID NO: 71) | GYTIISGKHFYFNTDGIMQI**GVFKGPDGFEYFA**<br>**PANTDANNIEGQAIRYQN**RFLYLHDNIYYFGN<br>NSKAATGWVTIDGNRYYFEPNTAMGAN |
| Module 7 LR = SEQ ID NO: 72) | **GVFKGSNGFEYFAPANTDANNIEGQAIRYQN** |
| Module 7 (residues 2595-2710 = SEQ ID NO: 73) | GYKTIDNKNFYFRNGLPQI**GVFKGSNGFEYFA**<br>**PANTDANNIEGQAIRYQN**RFLHLLGKIYYFGN<br>NSKAVTGWQTINGKVYYYFMPDTAMAAAGGLF<br>EIDGVIYFFGVDGVKAPGIYG |

TABLE 2

| Toxin B Receptor-Binding Repeat Modules | |
|---|---|
| Toxin B Receptor-Binding Modules | Amino acid Sequence (Long Repeat regions shown in bold) |
| Module 1 LR = SEQ ID NO: 74 | **GVFSTEDGFKYFAPANTLDENLEGEAIDFT** |
| Module 1 (residues 1852-2007 = SEQ ID NO: 75) | DDKYYFNPINGGAASIGETIIDDKNYYFNQSGV<br>LQT**GVFSTEDGFKYFAPANTLDENLEGEAID**<br>**FT**GKLIIDENIYYFDDNYRGAVEWKELDGEMH<br>YFSPETGKAFKGLNQIGDYKYYFNSDGVMQKG<br>FVSINDNKHYFDDSGVMKV |

TABLE 2-continued

| Toxin B Receptor-Binding Repeat Modules | |
|---|---|
| Toxin B Receptor-Binding Modules | Amino acid Sequence (Long Repeat regions shown in bold) |
| Module 2 LR = SEQ ID NO: 76 | **GVFNTEDGFKYFAHHNEDLGNEEGEEISYS** |
| Module 2 (residues 2008-2139 = SEQ ID NO: 77) | GYTEIDGKHFYFAENGEMQI**GVFNTEDGFKYF**<br>**AHHNEDLGNEEGEEISYS**GILNFNNKIYYFDD<br>SFTAVVGWKDLEDGSKYYFDEDTAEAYIGLSLI<br>NDGQYYFNDDGIMQVGFVTINDKVFYFSDSGII<br>ES |
| Module 3 LR = SEQ ID NO: 78 | **GVFDTSDGYKYFAPANTVNDNIYGQAVEYS** |
| Module 3 (residues 2140-2273 = SEQ ID NO: 79) | GVQNIDDNYFYIDDNGIVQI**GVFDTSDGYKYF**<br>**APANTVNDNIYGQAVEYS**GLVRVGEDVYYFG<br>ETYTIETGWIYDMENESDKYYFNPETKKACKGI<br>NLIDDIKYYFDEKGIMRTGLISFENNNYYFNEN<br>GEMQF |
| Module 4 LR = SEQ ID NO: 80 | **GVFNTPDGFKYFAHQNTLDENFEGESINYT** |
| Module 4 (residues 2274-2366 = SEQ ID NO: 81) | GYINIEDKMFYFGEDGVMQI**GVFNTPDGFKYF**<br>**AHQNTLDENFEGESINYT**GWLDLDEKRYYFT<br>DEYIAATGSVIIDGEEYYFDPDTAQLVISE |

TABLE 3

Neutralisation titres obtained by immunisation of sheep with recombinant Toxin B-derived antigens (6 weeks time point; 2 doses of 100 μg each)

| Toxin B- derived Antigen (amino acid sequence) | Neutralisation titre against Toxin B (0.5 ng/ml) |
|---|---|
| Recombinant Toxin B (1756-2366) | <10 |
| Recombinant Toxin B (1145-2366) | 960 |
| Recombinant Toxin B (767-2366) | 2,560 |
| Recombinant Toxin B (543-2366) | 1,280 |

TABLE 4

Neutralisation titres obtained by immunisation of sheep with recombinant Toxin B-derived antigens (18 weeks time point; 5 doses of 100 μg each)

| Toxin B- derived Antigen (amino acid sequence) | Neutralisation titre against Toxin B (0.5 ng/ml) |
|---|---|
| Recombinant Toxin B (1756-2366) | 80 |
| Recombinant Toxin B (1145-2366) | 5,120 |
| Recombinant Toxin B (767-2366) | 10,250 |
| Recombinant Toxin B (543-2366) | 5,120 |

TABLE 5

Neutralisation titres obtained by immunisation of sheep with a recombinant Toxin B-derived antigen (TxB4; residues 767-2366) of the invention

| Antigen | No of Doses | Immunisation period (weeks) | Neutralisation titre against Toxin B (0.5 ng/ml) |
|---|---|---|---|
| Recombinant Toxin B | 2 | 6 | 2,560 |
| (residues 767-2366) | 3 | 10 | 2,560 |
| at 100 μg/dose | 4 | 14 | 10,250 |
| | 5 | 18 | 10,250 |
| | 6 | 22 | 20,480 |

TABLE 6

Neutralisation titres obtained by immunisation of sheep with a recombinant Toxin B-derived antigen (TxB2, 1756-2366) representing the repeat regions

| Antigen | No of Doses | Immunisation period (weeks) | Neutralisation titre against Toxin B (0.5 ng/ml) |
|---|---|---|---|
| Recombinant Toxin B | 2 | 6 | <10 |
| (residues 1756-2366) | 3 | 10 | 10 |
| at 100 μg/dose | 4 | 14 | 10 |
| | 5 | 18 | 80 |

TABLE 7

Neutralisation titres obtained by immunisation of sheep with recombinant Toxin A-derived antigens (10 weeks time point)

| Toxin A- derived Antigen (amino acid sequence) | No of Doses (100 μg) | Neutralisation titre against Toxin A (50 ng/ml) |
|---|---|---|
| Recombinant Toxin A (1850-2710) | 3 | 640 |
| Recombinant Toxin A (770-2710) | 2 | 7,680 |
| Recombinant Toxin A(770-2389) | 3 | 10,240 |

TABLE 8

Neutralisation titres obtained by immunisation of sheep with recombinant Toxin A-derived antigens (18 weeks time point)

| Toxin A- derived Antigen (amino acid sequence) | No of Doses (100 μg) | Neutralisation titre against Toxin A (50 ng/ml) |
|---|---|---|
| Recombinant Toxin A (1850-2710) | 5 | 1,280 |
| Recombinant Toxin A (770-2710) | 4 | 15,360 |

TABLE 9

Neutralisation titres obtained by immunisation of sheep with a recombinant Toxin A-derived antigen (TxA4; residues 770-2710) of the invention

| Antigen | No of Doses | Immunisation period (weeks) | Neutralisation titre against Toxin A (50 ng/ml) |
|---|---|---|---|
| Recombinant Toxin A | 2 | 10 | 7,680 |
| (residues 770-2710) | 3 | 14 | 10,240 |
| at 100 μg/dose | 4 | 18 | 15,360 |

TABLE 10

Neutralisation titres obtained by immunisation of sheep with a recombinant Toxin A-derived antigen (TxA2; residues 1850-2710) representing the repeat region only

| Antigen | No of Doses | Immunisation period (weeks) | Neutralisation titre against Toxin A (50 ng/ml) |
|---|---|---|---|
| Recombinant Toxin A | 2 | 6 | 320 |
| (residues 1850-2710) | 3 | 10 | 630 |
| at 100 μg/dose | 4 | 14 | 1,280 |
| | 5 | 18 | 1,280 |

SEQ ID NOs

SEQ ID NO: 1 - *Clostridium difficile* Toxin A (Toxinotype 0)
MSLISKEELIKLAYSIRPRENEYKTILTNLDEYNKLTTNNNENKYLQLKKLNESID
VFMNKYKTSSRNRALSNLKKDILKEVILIKNSNTSPVEKNLHFVWIGGEVSDIALE
YIKQWADINAEYNIKLWYDSEAFLVNTLKKAIVESSTTEALQLLEEEIQNPQFDN
MKFYKKRMEFIYDRQKRFINYYKSQINKPTVPTIDDIIKSHLVSEYNRDETVLESY
RTNSLRKINSNHGIDIRANSLFTEQELLNIYSQELLNRGNLAAASDIVRLLALKNF
GGVYLDVDMLPGIHSDLFKTISRPSSIGLDRWEMIKLEAIMKYKKYINNYTSENF
DKLDQQLKDNFKLIIESKSEKSEIFSKLENLNVSDLEIKIAFALGSVINQALISKQGS
YLTNLVIEQVKNRYQFLNQHLNPAIESDNNFTDTTKIFHDSLFNSATAENSMFLTK
IAPYLQVGFMPEARSTISLSGPGAYASAYYDFINLQENTIEKTLKASDLIEFKFPEN
NLSQLTEQEINSLWSFDQASAKYQFEKYVRDYTGGSLSEDNGVDFNKNTALDKN
YLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVD
SLSNEISSFLDTIKLDISPKNVEVNLLGCNMFSYDFNVEETYPGKLLLSIMDKITST
LPDVNKNSITIGANQYEVRINSEGRKELLAHSGKWINKEEAIMSDLSSKEYIFFDSI
DNKLKAKSKNIPGLASISEDIKTLLLDASVSPDTKFILNNLKLNIESSIGDYIYYEKL
EPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQV
NTLNAAFFIQSLIDYSSNKDVLNDLSTSVKVQLYAQLFSTGLNTIYDSIQLVNLISN
AVNDTINVLPTITEGIPIVSTILDGINLGAAIKELLDEHDPLLKKELEAKVGVLAIN
MSLSIAATVASIVGIGAEVTIFLLPIAGISAGIPSLVNNELILHDKATSVVNYFNHLS
ESKKYGPLKTEDDKILVPIDDLVISEIDFNNNSIKLGTCNILAMEGGSGHTVTGNID
HFFSSPSISSHIPSLSIYSAIGIETENLDFSKKIMMLPNAPSRVFWWETGAVPGLRSL
ENDGTRLLDSIRDLYPGKFYWRFYAFFDYAITTLKPVYEDTNIKIKLDKDTRNFIM
PTITTNEIRNKLSYSFDGAGGTYSLLLSSYPISTNINLSKDDLWIFNIDNEVREISIEN
GTIKKGKLIKDVLSKIDINKNKLIIGNQTIDFSGDIDNKDRYIFLTCELDDKISLIIEI
NLVAKSYSLLLSGDKNYLISNLSNTIEKINTLGLDSKNIAYNYTDESNNKYFGAIS
KTSQKSIIHYKKDSKNILEFYNDSTLEFNSKDFIAEDINVFMKDDINTITGKYYVD
NNTDKSIDFSISLVSKNQVKVNGLYLNESVYSSYLDFVKNSDGHHNTSNFMNLFL
DNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LTSYKIINGKHFYFNNDGVMQLGVFKGPDGFEYFAPANTQNNNIEGQAIVYQSKF
LTLNGKKYYFDNNSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGLQTIDSKKYYF
NTNTAEAATGWQTIDGKKYYFNTNTAEAATGWQTIDGKKYYFNTNTAIASTGY
TIINGKHFYFNTDGIMQIGVFKGPNGFEYFAPANTDANNIEGQAILYQNEFLTLNG
KKYYFGSDSKAVTGWRIINNKKYYFNPNNAIAAIHLCTINNDKYYFSYDGILQNG
YITIERNNFYFDANNESKMVTGVFKGPNGFEYFAPANTHNNNIEGQAIVYQNKFL
TLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTDANNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG SEQ ID NO: 2 - *C. difficile* Toxin B (Toxinotype 0)
MSLVNRKQLEKMANVRFRTQEDEYVAILDALEEYHNMSENTVVEKYLKLKDIN
SLTDIYIDTYKKSGRNKALKKFKEYLVTEVLELKNNNLTPVEKNLHFVWIGGQIN
DTAINYINQWKDVNSDYNVNVFYDSNAFLINTLKKTVVESAINDTLESFRENLND
PRFDYNKFFRKRMEIIYDKQKNFINYYKAQREENPELIIDDIVKTYLSNEYSKEIDE
LNTYIEESLNKITQNSGNDVRNFEEFKNGESFNLYEQELVERWNLAAASDILRISA
LKEIGGMYLDVDMLPGIQPDLFESIEKPSSVTVDFWEMTKLEAIMKYKEYIPEYTS
EHFDMLDEEVQSSFESVLASKSDKSEIFSSLGDMEASPLEVKIAFNSKGIINQGLIS
VKDSYCSNLIVKQIENRYKILNNSLNPAISEDNDFNTTTNTFIDSIMAEANADNGR
FMMELGKYLRVGFFPDVKTTINLSGPEAYAAAYQDLLMFKEGSMNIHLIEADLR -continued

| SEQ ID NOs |
|---|

NFEISKTNISQSTEQEMASLWSFDDARAKAQFEEYKRNYFEGSLGEDDNLDFSQN
IVVDKEYLLEKISSLARSSERGYIHYIVQLQGDKISYEAACNLFAKTPYDSVLFQK
MEDSEIAYYYNPGDGEIQEIDKYKIPSIISDRPKIKLTFIGHGKDEFNTDIFAGFDV
DSLSTEIEAAIDLAKEDISPKSIEINLLGCNMFSYSINVEETYPGKLLLKVKDKISEL
MPSISQDSIIVSANQYEVRINSEGRRELLDHSGEWINKEESIIKDISSKEYISFNPKEN
KITVKSKNLPELSTLLQEIRNNSNSSDIELEEKVMLTECEINVISNIDTQIVEERIEEA
KNLTSDSINYIKDEFKLIESISDALCDLKQQNELEDSHFISFEDISETDEGFSIRFINK
ETGESIFVETEKTIFSEYANHITEEISKIKGTIFDTVNGKLVKKVNLDTTHEVNTLN
AAFFIQSLIEYNSSKESLSNLSVAMKVQVYAQLFSTGLNTITDAAKVVELVSTALD
ETIDLLPTLSEGLPIIATIIDGVSLGAAIKELSETSDPLLRQEIEAKIGIMAVNLTTAT
TAIITSSLGIASGFSILLVPLAGISAGIPSLVNNELVLRDKATKVVDYFKHVSLVETE
GVFTLLDDKIMMPQDDLVISEIDFNNNSIVLGKCEIWRMEGGSGHTVTDDIDHFF
SAPSITYREPHLSIYDVLEVQKEELDLSKDLMVLPNAPNRVFAWETGWTPGLRSL
ENDGTKLLDRIRDNYEGEFYWRYFAFIADALITTLKPRYEDTNIRINLDSNTRSFIV
PIITTEYIREKLSYSFYGSGGTYALSLSQYNMGINIELSESDVWIIDVDNVVRDVTI
ESDKIKKGDLIEGILSTLSIEENKIILNSHEINFSGEVNGSNGFVSLTFSILEGINAIIE
VDLLSKSYKLLISGELKILMLNSNHIQQKIDYIGFNSELQKNIPYSFVDSEGKENGF
INGSTKEGLFVSELPDVVLISKVYMDDSKPSFGYYSNNLKDVKVITKDNVNILTG
YYLKDDIKISLSLTLQDEKTIKLNSVHLDESGVAEILKFMNRKGNTNTSDSLMSFL
ESMNIKSIFVNFLQSNIKFILDANFIISGTTSIGQFEFICDENDNIQPYFIKFNTLETNY
TLYVGNRQNMIVEPNYDLDDSGDISSTVINFSQKYLYGIDSCVNKVVISPNIYTDE
INITPVYETNNTYPEVIVLDANYINEKINVNINDLSIRYVWSNDGNDFILMSTSEEN
KVSQVKIRFVNVFKDKTLANKLSFNFSDKQDVPVSEIILSFTPSYYEDGLIGYDLG
LVSLYNEKFYINNFGMMVSGLIYINDSLYYFKPPVNNLITGFVTVGD
DKYYFNPINGGAASIGETIIDDKNYYFNQSGVLQTGVFSTEDGFKYFAPANTLDE
NLEGEAIDFTGKLIIDENIYYPDDNYRGAVEWKELDGEMHYFSPETGKAFKGLNQ
IGDYKYYFNSDGVMQKGFVSINDNKHYFDDSGVMKVGYTEIDGKHFYFAENGE
MQIGVFNTEDGFKYFAHHNEDLGNEEGEEISYSGILNFNNKIYYPDDSFTAVVGW
KDLEDGSKYYFDEDTAEAYIGLSLINDGQYYFNDDGIMQVGFVTINDKVFYFSDS
GIIESGVQNIDDNYFYIDDNGIVQIGVFDTSDGYKYFAPANTVNDNIYGQAVEYS
GLVRVGEDVYYFGETYTIETGWIYDMENESDKYYFNPETKKACKGINLIDDIKYY
FDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYY
FDPDTAQLVISE

SEQ ID NO: 3 - *C. difficile* Toxin A (Toxinotype 3)
MSLISKEELIKLAYSIRPRENEYKTILTNLDEYNKLTTNNNENKYLQLKKLNESID
VFMNKYKNSSRNRALSNLKKDILKEVILIKNSNTSPVEKNLHFVWIGGEVSDIALE
YIKQWADINAEYNIKLWYDSEAFLVNTLKKAIVESSTTEALQLLEEEIQNPQFDN
MKFYKKRMEFIYDRQKRFINYYKSQINKPTVPTIDDIIKSHLVSEYNRDETLLESY
RTNSLRKINSNHGIDIRANSLFTEQELLNIYSQELLNRGNLAAASDIVRLLALKNF
GGVYLDVDMLPGIHSDLFKTIPRPSSIGLDRWEMIKLEAIMKYKKYINNYTSENF
DKLDQQLKDNFKLIIESKSEKSEIFSKLENLNVSDLEIKIAFALGSVINQALISKQGS
YLTNLVIEQVKNRYQFLNQHLNPAIESDNNFTDTTKIFHDSLFNSATAENSMFLTK
IAPYLQVGFMPEARSTISLSGPGAYASAYYDFINLQENTIEKTLKASDLIEFKFPEN
NLSQLTEQEINSLWSFDQASAKYQFEKYVRDYTGGSLSEDNGVDFNKNTALDKN
YLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVD
SLSNEISSFLDTIKLDISPKNVEVNLLGCNMFSYDFNVEETYPGKLLLSIMDKITST
LPDVNKDSITIGANQYEVRINSEGRKELLAHSGKWINKEEAIMSDLSSKEYIFFDSI
DNKLKAKSKNIPGLASISEDIKTLLLDASVSPDTKFILNNLKLNIESSIGDYIYYEKL
EPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQV
NTLNAAFFIQSLIDYSSNKDVLNDLSTSVKVQLYAQLFSTGLNTIYDSIQLVNLISN
AVNDTINVLPTITEGIPIVSTILDGINLGAAIKELLDEHDPLLKKELEAKVGVLAIN
MSLSIAATVASIVGIGAEVTIFLLPIAGISAGIPSLVNNELILHDKATSVVNYFNHLS
ESKEYGPLKTEDDKILVPIDDLVISEIDFNNNSIKLGTCNILAMEGGSGHTVTGNID
HFFSSPYISSHIPSLSVYSAIGIKTENLDFSKKIMMLPNAPSRVFWWETGAVPGLRS
LENNGTKLLDSIRDLYPGKFYWRFYAFFDYAITTLKPVYEDTNTKIKLDKDTRNFI
MPTITTDEIRNKLSYSFDGAGGTYSLLLSSYPISMNINLSKDDLWIFNIDNEVREISI
ENGTIKKGNLIEDVLSKIDINKNKLIIGNQTIDFSGDIDNKDRYIFLTCELDDKISLII
EINLVAKSYSLLLSGDKNYLISNLSNTIEKINTLGLDSKNIAYNYTDESNNKYFGAI
SKTSQKSIIHYKKDSKNILEFYNGSTLEFNSKDFIAEDINVFMKDDINTITGKYYVD
NNTDKSIDFSISLVSKNQVKVNGLYLNESVYSSYLDFVKNSDGHHNTSNFMNLFL
NNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIESNLVTGWQTINGKKYYFDINTGAA
STSYKIINGKHFYFNNNGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSGSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTSIASTGY
TIINGKYFYFNTDGIMQIGVFKVPNGFEYFAPANTHNNNIEGQAILYQNKFLTLNG
KKYYFGSDSKAITGWQTIDGKKYYFNPNNAIAATHLCTINNDKYYFSYDGILQN
GYITIERNNFYFDANNESKMVTGVFKGPNGFEYFAPANTHNNNIEGQAIVYQNKF -continued SEQ ID NOs LTLNGKKYYFDNDSKAVTGWQTIDSKKYYFNLNTAVAVTGWQTIDGEKYYFNL
NTAEAATGWQTIDGKRYYFNTNTYIASTGYTIINGKHFYFNTDGIMQIGVFKGPD
GFEYFAPANTHNNNIEGQAILYQNKFLTLNGKKYYFGSDSKAVTGLRTIDGKKY
YFNTNTAVAVTGWQTINGKKYYFNTNTYIASTGYTIISGKHFYFNTDGIMQIGVF
KGPDGFEYFAPANTDANNIEGQAIRYQNRFLYLHDNIYYFGNDSKAATGWATID
GNRYYFEPNTAMGANGYKTIDNKNFYFRNGLPQIGVFKGPNGFEYFAPANTDAN
NIDGQAIRYQNRFLHLLGKIYYFGNNSKAVTGWQTINSKVYYFMPDTAMAAAG
GLFEIDGVIYFFGVDGVKAPGIYG SEQ ID NO: 4 - *C. difficile* Toxin B (Toxinotype 3)
MSLVNRKQLEKMANVRFRVQEDEYVAILDALEEYHNMSENTVVEKYLKLKDIN
SLTDIYIDTYKKSGRNKALKKFKEYLVTEVLELKNNNLTPVEKNLHFVWIGGQIN
DTAINYINQWKDVNSDYNVNVFYDSNAFLINTLKKTIVESATNDTLESFRENLND
PRFDYNKFYRKRMEIIYDKQKNFINYYKTQREENPDLIIDDIVKIYLSNEYSKDIDE
LNSYIEESLNKVTENSGNDVRNFEEFKGGESFKLYEQELVERWNLAAASDILRISA
LKEVGGVYLDVDMLPGIQPDLFESIEKPSSVTVDFWEMVKLEAIMKYKEYIPGYT
SEHFDMLDEEVQSSFESVLASKSDKSEIFSSLGDMEASPLEVKIAFNSKGIINQGLI
SVKDSYCSNLIVKQIENRYKILNNSLNPAISEDNDFNTTTNAFIDSIMAEANADNG
RFMMELGKYLRVGFFPDVKTTINLSGPEAYAAAYQDLLMFKEGSMNIHLIEADL
RNFEISKTNISQSTEQEMASLWSFDDARAKAQFEEYKKNYFEGSLGEDDNLDFSQ
NTVVDKEYLLEKISSLARSSERGYIHYIVQLQGDKISYEAACNLFAKTPYDSVLFQ
KNIEDSEIAYYYNPGDGEIQEIDKYKIPSIISDRPKIKLTFIGHGKDEFNTDIFAGLD
VDSLSTEIETAIDLAKEDISPKSIEINLLGCNMFSYSVNVEETYPGKLLLRVKDKVS
ELMPSISQDSIIVSANQYEVRINSEGRRELLDHSGEWINKEESIIKDISSKEYISFNPK
ENKIIVKSKNLPELSTLLQEIRNNSNSSDIELEEKVMLAECEINVISNIDTQVVEGRI
EEAKSLTSDSINYIKNEFKLIESISDALYDLKQQNELEESHFISFEDILETDEGFSIRFI
DKETGESIFVETEKAIFSEYANHITEEISKIKGTIFDTVNGKLVKKVNLDATHEVNT
LNAAFFIQSLIEYNSSKESLSNLSVAMKVQVYAQLFSTGLNTITDAAKVVELVSTA
LDETIDLLPTLSEGLPVIATIIDGVSLGAAIKELSETSDPLLRQEIEAKIGIMAVNLT
AATTAIITSSLGIASGFSILLVPLAGISAGIPSLVNNELILRDKATKVVDYFSHISLAE
SEGAFTSLDDKIMMPQDDLVISEIDFNNNSITLGKCEIWRMEGGSGHTVTDDIDHF
FSAPSITYREPHLSIYDVLEVQKEELDLSKDLMVLPNAPNRVFAWETGWTPGLRS
LENDGTKLLDRIRDNYEGEFYWRYFAFIADALITTLKPRYEDTNIRINLDSNTRSFI
VPVITTEYIREKLSYSFYGSGGTYALSLSQYNMNINIELNENDTWVIDVDNVVRD
VTIESDKIKKGDLIENILSKLSIEDNKIILDNHEINFSGTLNGGNGFVSLTFSILEGIN
AVIEVDLLSKSYKVLISGELKTLMANSNSVQQKIDYIGLNSELQKNIPYSFMDDK
GKENGFINCSTKEGLFVSELSDVVLISKVYMDNSKPLFGYCSNDLKDVKVITKDD
VIILTGYYLKDDIKISLSFTIQDENTIKLNGVYLDENGVAEILKFMNKKGSTNTSDS
LMSFLESMNIKSIFINSLQSNTKLILDTNFIISGTTSIGQFEFICDKDNNIQPYFIKFNT
LETKYTLYVGNRQNMIVEPNYDLDDSGDISSTVINFSQKYLYGIDSCVNKVIISPNI
YTDEINITPIYEANNTYPEVIVLDTNYISEKINININDLSIRYVWSNDGSDFILMSTD
EENKVSQVKIRFTNVFKGNTISDKISFNFSDKQDVSINKVISTFTPSYYVEGLLNYD
LGLISLYNEKFYINNFGMMVSGLVYINDSLYYFKPPIKNLITGFTTIGDDKYYFNP
DNGGAASVGETIIDGKNYYFSQNGVLQTGVFSTEDGFKYFAPADTLDENLEGEAI
DFTGKLTIDENVYYFGDNYRAAIEWQTLDDEVYYFSTDTGRAFKGLNQIGDDKF
YFNSDGIMQKGFVNINDKTFYFDDSGVMKSGYTEIDGKYFYFAENGEMQIGVFN
TADGFKYFAHHDEDLGNEEGEALSYSGILNFNNKIYYFDDSFTAVVGWKDLEDG
SKYYFDEDTAEAYIGISIINDGKYYFNDSGIMQIGFVTINNEVFYFSDSGIVESGMQ
NIDDNYFYIDENGLVQIGVFDTSDGYKYFAPANTVNDNIYGQAVEYSGLVRVGE
DVYYFGETYTIETGWIYDMENESDKYYFDPETKKAYKGINVIDDIKYYFDENGIM
RTGLITFEDNHYYFNEDGIMQYGYLNIEDKTFYFSEDGIMQIGVFNTPDGFKYFA
HQNTLDENFEGESINYTGWLDLDEKRYYFTDEYIAATGSVIIDGEEYYFDPDTAQ
LVISE SEQ ID NO: 5 - Toxin A fragment - TxA3 (Toxinotype 0)(Residues 1131-2710)
ESKKYGPLKTEDDKILVPIDDLVISEIDFNNNSIKLGTCNILAMEGGSGHTVTGNID
HFFSSPSISSHIPSLSIYSAIGIETENLDFSKKIMMLPNAPSRVFWWETGAVPGLRSL
ENDGTRLLDSIRDLYPGKFYWRFYAFFDYAITTLKPVYEDTNIKIKLDKDTRNFIM
PTITTNEIRNKLSYSFDGAGGTYSLLLSSYPISTNINLSKDDLWIFNIDNEVREISIEN
GTIKKGKLIKDVLSKIDINKNKLIIGNQTIDFSGDIDNKDRYIFLTCELDDKISLIIEI
NLVAKSYSLLLSGDKNYLISNLSNIIEKINTLGLDSKNIAYNYTDESNNKYFGAISK
TSQKSIIHYKKDSKNILEFYNDSTLEFNSKDFIAEDINVFMKDDINTITGKYYVDN
NTDKSIDFSISLVSKNQVKVNGLYLNESVYSSYLDFVKNSDGHHNTSNFMNLFLD
NISFWKLFGFENINFVIDKYFTLVGKTNLGYVEFICDNNKNIDIYFGEWKTSSSKS
TIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LISYKIINGKHFYFNNDGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTAIASTG
YTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQN
GYITIERNNFYFDANNESKMVTGVFKGPNGFEYFAPANTHNNNIEGQAIVYQNKF
LTLNGKKYYFDNDSKAVTGWQTIDGKKYYFNLNTAEAATGWQTIDGKKYYFNL -continued

| SEQ ID NOs |
|---|

NTAEAATGWQTIDGKKYYFNTNTFIASTGYTSINGKHFYFNTDGIMQIGVFKGPN
GFEYFAPANTHNNNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG

SEQ ID NO: 6 - Toxin A fragment - TxA3 (Toxinotype 3)(Residues 1131-2710)
ESKKYGPLKTEDDKILVPIDDLVISEIDFNNNSIKLGTCNILAMEGGSGHTVTGNID
HFFSSPSISSHIPSLSIYSAIGIETENLDFSKKIMMLPNAPSRVFWWETGAVPGLRSL
ENDGTRLLDSIRDLYPGKFYWRFYAFFDYAITTLKPVYEDTNIKIKLDKDTRNFIM
PTITTNEIRNKLSYSFDGAGGTYSLLLSSYPISTNINLSKDDLWIFNIDNEVREISIEN
GTIKKGKLIKDVLSKIDINKNKLIIGNQTIDFSGDIDNKDRYIFLTCELDDKISLIIEI
NLVAKSYSLLLSGDKNYLISNLSNTIEKINTLGLDSKNIAYNYTDESNNKYFGAIS
KTSQKSIIHYKKDSKNILEFYNDSTLEFNSKDFIAEDINVFMKDDINTITGKYYVD
NNTDKSIDFSISLVSKNQVKVNGLYLNESVYSSYLDFVKNSDGHHNTSNFMNLFL
DNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LTSYKIINGKHFYFNNDGVMQLGVFKGPDGFEYFAPANTQNNNIEGQAIVYQSKF
LTLNGKKYYFDNNSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGLQTIDSKKYYF
NTNTAEAATGWQTIDGKKYYFNTNTAEAATGWQTIDGKKYYFNTNTAIASTGY
TIINGKHFYFNTDGIMQIGVFKGPNGFEYFAPANTDANNIEGQAILYQNEFLTLNG
KKYYFGSDSKAVTGWRIINNKKYYFNPNNAIAAIHLCTINNDKYYFSYDGILQNG
YITIERNNFYFDANNESKMVTGVFKGPNGFEYFAPANTHNNNIEGQAIVYQNKFL
TLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTDANNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG SEQ ID NO: 7 - Toxin A fragment - TxA4 (Toxinotype 0)(Residues 770-2710)
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
LKKELEAKVGVLAINMSLSIAATVASIVGIGAEVTIFLLPIAGISAGIPSLVNNELIL
HDKATSVVNYFNHLSESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYSPDGAGGTYSLLLSSYPISTNINLSKD
DLWIFNIDNEVREISIENGTIKKGKLIKDVLSKIDINKNKLIIGNQTIDFSGDIDNKD
RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
KNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLVTGW
QTINGKKYYFDINTGAALISYKIINGKHFYFNNDGVMQLGVFKGPDGFEYFAPAN
TQNNNIEGQAIVYQSKFLTLNGKKYYFDNDSKAVTGWRIINNEKYYFNPNNAIA
AVGLQVIDNNKYYFNPDTAIISKGWQTVNGSRYYFDTDTAIAFNGYKTIDGKHF
YFDSDCVVKIGVFSTSNGFEYFAPANTYNNNIEGQAIVYQSKFLTLNGKKYYFDN
NSKAVTGWQTIDSKKYYFNTNTAEAATGWQTIDGKKYYFNTNTAEAATGWQTI
DGKKYYFNTNTAIASTGYTIINGKHFYFNTDGIMQIGVFKGPNGFEYFAPANTDA
NNIEGQAILYQNEFLTLNGKKYYFGSDSKAVTGWRIINNKKYYFNPNNAIAAIHL
CTINNDKYYFSYDGILQNGYITIERNNFYFDANNESKMVTGVFKGPNGFEYFAPA
NTHNNNIEGQAIVYQNKFLTLNGKKYYFDNDSKAVTGWQTIDGKKYYFNLNTA
EAATGWQTIDGKKYYFNLNTAEAATGWQTIDGKKYYFNTNTFIASTGYTSINGK
HFYFNTDGIMQIGVFKGPNGFEYFAPANTHNNNIEGQAILYQNKFLTLNGKKYYF
GSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNI
YYFGNNSKAATGWVTIDGNRYYFEPNTAMGANGYKTIDNKNFYFRNGLPQIGV
FKGSNGFEYFAPANTDANNIEGQAIRYQNRFLHLLGKIYYFGNNSKAVTGWQTIN
GKVYYFMPDTAMAAAGGLFEIDGVIYFFGVDGVKAPGIYG -continued

| SEQ ID NOs |
|---|

SEQ ID NO: 8 - Toxin A fragment - TxA4 (Toxinotype 3)(Residues 770-2710)
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
LKKELEAKVGVLAINMSLSIAATVASIVGIGAEVTIFLLPIAGISAGIPSLVNNELIL
HDKATSVVNYFNHLSESKEYGPLKTEDDKILVPIDDLVISEIDFNNNSIKLGTCNIL
AMEGGSGHTVTGNIDHFFSSPYISSHIPSLSVYSAIGIKTENLDFSKKIMMLPNAPS
RVFWWETGAVPGLRSLENNGTKLLDSIRDLYPGKFYWRFYAFFDYAITTLKPVY
EDTNTKIKLDKDTRNFIMPTITTDEIRNKLSYSFDGAGGTYSLLLSSYPISMNINLS
KDDLWIFNIDNEVREISIENGTIKKGNLIEDVLSKIDINKNKLIIGNQTIDFSGDIDN
KDRYIFLTCELDDKISLIIEINLVAKSYSLLLSGDKNYLISNLSNTIEKINTLGLDSK
NIAYNYTDESNNKYFGAISKTSQKSIIHYKKDSKNILEFYNGSTLEFNSKDFIAEDI
NVFMKDDINTITGKYYVDNNTDKSIDFSISLVSKNQVKVNGLYLNESVYSSYLDF
VKNSDGHHNTSNFMNLFLNNISFWKLFGFENINFVIDKYFTLVGKTNLGYVEFIC
DNNKNIDIYFGEWKTSSSKSTIFSGNGRNVVVEPIYNPDTGEDISTSLDFSYEPLYG
IDRYINKVLIAPDLYTSLININTNYYSNEYYPEIIVLNPNTFHKKVNINLDSSSFEYK
WSTEGSDFILVRYLEESNKKILQKIRIKGILSNTQSFNKMSIDFKDIKKLSLGYIMS
NFKSFNSENELDRDHLGFKIIDNKTYYYDEDSKLVKGLININNSLFYFDPIESNLVT
GWQTINGKKYYPDINTGAASTSYKIINGKHFYFNNNGVMQLGVFKGPDGFEYFA
PANTQNNNIEGQAIVYQSKFLTLNGKKYYFDNDSKAVTGWRIINNEKYYFNPNN
AIAAVGLQVIDNNKYYFNPDTAIISKGWQTVNGSRYYFDTDTAIAFNGYKTIDGK
HFYFDSDCVVKIGVFSGSNGFEYFAPANTYNNNIEGQAIVYQSKFLTLNGKKYYF
DNNSKAVTGWQTIDSKKYYFNTNTAEAATGWQTIDGKKYYFNTNTAEAATGW
QTIDGKKYYFNTNTSIASTGYTIINGKYFYFNTDGIMQIGVFKVPNGFEYFAPANT
HNNNIEGQAILYQNKFLTLNGKKYYFGSDSKAITGWQTIDGKKYYFNPNNAIAA
THLCTINNDKYYFSYDGILQNGYITIERNNFYFDANNESKMVTGVFKGPNGFENF
APANTHNNNIEGQAIVYQNKFLTLNGKKYYPDNDSKAVTGWQTIDSKKYYFNL
NTAVAVTGWQTIDGEKYYFNLNTAEAATGWQTIDGKRYYFNTNTYIASTGYTII
NGKHFYFNTDGIMQIGVFKGPDGFEYFAPANTHNNNIEGQAILYQNKFLTLNGK
KYYFGSDSKAVTGLRTIDGKKYYFNTNTAVAVTGWQTINGKKYYFNTNTYIAST
GYTIISGKHFYFNTDGIMQIGVFKGPDGFEYFAPANTDANNIEGQAIRYQNRFLYL
HDNIYYFGNDSKAATGWATIDGNRYYFEPNTAMGANGYKTIDNKNFYFRNGLP
QIGVFKGPNGFEYFAPANTDANNIDGQAIRYQNRFLHLLGKIYYFGNNSKAVTG
WQTINSKVYYFMPDTAMAAAGGLFEIDGVIYFFGVDGVKAPGIYG SEQ ID NO: 9 - Toxin B fragment - TxB3(-h)(Toxinotype 0)(Residues 1145-2366)
MPQDDLVISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKLLDRI
RDNYEGEFYWRYFAFIADALITTLKPRYEDTNIRINLDSNTRSFIVPIITTEYIREKL
SYSFYGSGGTYALSLSQYNMGINIELSESDVWIIDVDNVVRDVTIESDKIKKGDLI
EGILSTLSIEENKIILNSHEINFSGEVNGSNGFVSLTFSILEGINAIIEVDLLSKSYKLL
ISGELKILMLNSNHIQQKIDYIGFNSELQKNIPYSFVDSEGKENGFINGSTKEGLFV
SELPDVVLISKVYMDDSKPSFGYYSNNLKDVKVITKDNVNILTGYYLKDDIKISLS
LTLQDEKTIKLNSVHLDESGVAEILKFMNRKGNTNTSDSLMSFLESMNIKSIFVNF
LQSNIKFILDANFIISGTTSIGQFEFICDENDNIQPYFIKFNTLETNYTLYVGNRQNM
IVEPNYDLDDSGDISSTVINFSQKYLYGIDSCVNKVVISPNIYTDEINITPVYETNNT
YPEVIVLDANYINEKINVNINDLSIRYVWSNDGNDFILMSTSEENKVSQVKIRFVN
VFKDKTLANKLSFNFSDKQDVPVSEIILSFTPSYYEDGLIGYDLGLVSLYNEKFYI
NNFGMMVSGLIYINDSLYYFKPPVNNLITGFVTVGDDKYYFNPINGGAASIGETII
DDKNYYFNQSGVLQTGVFSTEDGFKYFAPANTLDENLEGEAIDFTGKLIIDENIY
YFDDNYRGAVEWKELDGEMHYFSPETGKAFKGLNQIGDYKYYFNSDGVMQKG
FVSINDNKHYFDDSGVMKVGYTEIDGKHFYFAENGEMQIGVFNTEDGFKYFAHH
NEDLGNEEGEEISYSGILNFNNKIYYFDDSFTAVVGWKDLEDGSKYYFDEDTAEA
YIGLSLINDGQYYFNDDGIMQVGFVTINDKVFYFSDSGIIESGVQNIDDNYFYIDD
NGIVQIGVFDTSDGYKYFAPANTVNDNIYGQAVEYSGLVRVGEDVYYFGETYTI
ETGWIYDMENESDKYYFNPETKKACKGINLIDDIKYYFDEKGIMRTGLISFENNN
YYFNENGEMQFGYINIEDKMFYFGEDGVMQIGVFNTPDGFKYFAHQNTLDENFE
GESINYTGWLDLDEKRYYFTDEYIAATGSVIIDGEEYYPDPDTAQLVISE SEQ ID NO: 10 - Toxin B fragment - TxB3(-h)(Toxinotype 3)(Residues 1145-2366)
MPQDDLVISEIDFNNNSITLGKCEIWRMEGGSGHTVTDDIDHFFSAPSITYREPHLS
IYDVLEVQKEELDLSKDLMVLPNAPNRVFAWETGWTPGLRSLENDGTKLLDRIR
DNYEGEFYWRYFAFIADALITTLKPRYEDTNIRINLDSNTRSFIVPVITTEYIREKLS
YSFYGSGGTYALSLSQYNMNINIELNENDTWVIDVDNVVRDVTIESDKIKKGDLI
ENILSKLSIEDNKIILDNHEINFSGTLNGGNGFVSLTFSILEGINAVIEVDLLSKSYK
VLISGELKTLMANSNSVQQKIDYIGLNSELQKNIPYSFMDDKGKENGFINCSTKEG
LFVSELSDVVLISKVYMDNSKPLFGYCSNDLKDVKVITKDDVIILTGYYLKDDIKI
SLSFTIQDENTIKLNGVYLDENGVAEILKFMNKKGSTNTSDSLMSFLESMNIKSIFI
NSLQSNTKLILDTNFIISGTTSIGQFEFICDKDNNIQPYFIKFNTLETKYTLYVGNRQ
NMIVEPNYDLDDSGDISSTVINFSQKYLYGIDSCVNKVIISPNIYTDEINITPIYEAN
NTYPEVIVLDTNYISEKINININDLSIRYVWSNDGSDFILMSTDEENKVSQVKIRFT
NVFKGNTISDKISFNFSDKQDVSINKVISTFTPSYYVEGLLNYDLGLISLYNEKFYI
NNFGMMVSGLVYINDSLYYFKPPIKNLITGFTTIGDDKYYFNPDNGGAASVGETII
DGKNYYFSQNGVLQTGVFSTEDGFKYFAPADTLDENLEGEAIDFTGKLTIDENVY -continued

| SEQ ID NOs |
|---|

YFGDNYRAAIEWQTLDDEVYYFSTDTGRAFKGLNQIGDDKFYFNSDGIMQKGFV
NINDKTFYFDDSGVMKSGYTEIDGKYFYFAENGEMQIGVFNTADGFKYFAHHDE
DLGNEEGEALSYSGILNFNNKIYYFDDSFTAVVGWKDLEDGSKYYFDEDTAEAY
IGISIINDGKYYFNDSGIMQIGFVTINNEVFYFSDSGIVESGMQNIDDNYFYIDENG
LVQIGVFDTSDGYKYFAPANTVNDNIYGQAVEYSGLVRVGEDVYYFGETYTIET
GWIYDMENESDKYYPDPETKKAYKGINVIDDIKYYFDENGIMRTGLITFEDNHYY
FNEDGIMQYGYLNIEDKTFYFSEDGIMQIGVFNTPDGFKYFAHQNTLDENFEGESI
NYTGWLDLDEKRYYFTDEYIAATGSVIIDGEEYYPDPDTAQLVISE

SEQ ID NO: 11 - Toxin B fragment - TxB3 (Toxinotype 0)(Residues 957-2366)
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL
ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLITGFVTVGDDKYY
FNPINGGAASIGETIIDDKNYYFNQSGVLQTGVFSTEDGFKYFAPANTLDENLEGE
AIDFTGKLIIDENIYYFDDNYRGAVEWKELDGEMHYFSPETGKAFKGLNQIGDYK
YYFNSDGVMQKGFVSINDNKHYFDDSGVMKVGYTEIDGKHFYFAENGEMQIGV
FNTEDGFKYFAHHNEDLGNEEGEEISYSGILNFNNKIYYFDDSFTAVVGWKDLED
GSKYYFDEDTAEAYIGLSLINDGQYYFNDDGIMQVGFVTINDKVFYFSDSGIIESG
VQNIDDNYFYIDDNGIVQIGVFDTSDGYKYFAPANTVNDNIYGQAVEYSGLVRV
GEDVYYFGETYTIETGWIYDMENESDKYYFNPETKKACKGINLIDDIKYYFDEKG
IMRTGLISFENNNYYFNENGEMQFGYINIEDKMFYFGEDGVMQIGVFNTPDGFKY
FAHQNTLDENFEGESINYTGWLDLDEKRYYFTDEYIAATGSVIIDGEEYYPDPDT
AQLVISE SEQ ID NO: 12 - Toxin B fragment - TxB3 (Toxinotype 3)(Residues 957-2366)
NTLNAAFFIQSLIEYNSSKESLSNLSVAMKVQVYAQLFSTGLNTITDAAKVVELVS
TALDETIDLLPTLSEGLPVIATIIDGVSLGAAIKELSETSDPLLRQEIEAKIGIMAVN
LTAATTAIITSSLGIASGFSILLVPLAGISAGIPSLVNNELILRDKATKVVDYFSHISL
AESEGAFTSLDDKIMMPQDDLVISEIDFNNNSITLGKCEIWRMEGGSGHTVTDDID
HFFSAPSITYREPHLSIYDVLEVQKEELDLSKDLMVLPNAPNRVFAWETGWTPGL
RSLENDGTKLLDRIRDNYEGEFYWRYFAFIADALITTLKPRYEDTNIRINLDSNTR
SFIVPVITTEYIREKLSYSFYGSGGTYALSLSQYNMNINIELNENDTWVIDVDNVV
RDVTIESDKIKKGDLIENILSKLSIEDNKIILDNHEINFSGTLNGGNGFVSLTFSILEG
INAVIEVDLLSKSYKVLISGELKTLMANSNSVQQKIDYIGLNSELQKNIPYSFMDD
KGKENGFINCSTKEGLFVSELSDVVLISKVYMDNSKPLFGYCSNDLKDVKVITKD
DVIILTGYYLKDDIKISLSFTIQDENTIKLNGVYLDENGVAEILKFMNKKGSTNTSD
SLMSFLESMNIKSIFINSLQSNTKLILDTNFIISGTTSIGQFEFICDKDNNIQPYFIKFN
TLETKYTLYVGNRQNMIVEPNYDLDDSGDISSTVINFSQKYLYGIDSCVNKVIISP
NIYTDEINITPIYEANNTYPEVIVLDTNYISEKINININDLSIRYVWSNDGSDFILMST
DEENKVSQVKIRFTNVFKGNTISDKISFNFSDKQDVSINKVISTFTPSYYVEGLLNY
DLGLISLYNEKFYINNFGMMVSGLVYINDSLYYFKPPIKNLITGFTTIGDDKYYFN
PDNGGAASVGETIIDGKNYYFSQNGVLQTGVFSTEDGFKYFAPADTLDENLEGE
AIDFTGKLTIDENVYYFGDNYRAAIEWQTLDDEVYYFSTDTGRAFKGLNQIGDD
KFYFNSDGIMQKGFVNINDKTFYFDDSGVMKSGYTEIDGKYFYFAENGEMQIGV
FNTADGFKYFAHHDEDLGNEEGEALSYSGILNFNNKIYYFDDSFTAVVGWKDLE
DGSKYYFDEDTAEAYIGISIINDGKYYFNDSGIMQIGFVTINNEVFYFSDSGIVESG
MQNIDDNYFYIDENGLVQIGVFDTSDGYKYFAPANTVNDNIYGQAVEYSGLVRV
GEDVYYFGETYTIETGWIYDMENESDKYYFDPETKKAYKGINVIDDIKYYFDEN
GIMRTGLITFEDNHYYFNEDGIMQYGYLNIEDKTFYFSEDGIMQIGVFNTPDGFK
YFAHQNTLDENFEGESINYTGWLDLDEKRYYFTDEYIAATGSVIIDGEEYYFDPD
TAQLVISE SEQ ID NO: 13 - Toxin B fragment - TxB 4 (Toxinotype 0)(Residues 767-2366)
SIIKDISSKEYISFNPKENKITVKSKNLPELSTLLQEIRNNSNSSDIELEEKVMLTECE
INVISNIDTQIVEERIEEAKNLTSDSINYIKDEFKLIESISDALCDLKQQNELEDSHFI
SFEDISETDEGFSIRFINKETGESIFVETEKTIFSEYANHITEEISKIKGTIFDTVNGKL
VKKVNLDTTHEVNTLNAAFFIQSLIEYNSSKESLSNLSVAMKVQVYAQLFSTGLN
TITDAAKVVELVSTALDETIDLLPTLSEGLPIIATIIDGVSLGAAIKELSETSDPLLRQ
EIEAKIGIMAVNLTTATTAIITSSLGIASGFSILLVPLAGISAGIPSLVNNELVLRDKA
TKVVDYFKHVSLVETEGVFTLLDDKIMMPQDDLVISEIDFNNNSIVLGKCEIWRM
EGGSGHTVTDDIDHFFSAPSITYREPHLSIYDVLEVQKEELDLSKDLMVLPNAPNR
VFAWETGWTPGLRSLENDGTKLLDRIRDNYEGEFYWRYFAFIADALITTLKPRYE
DTNIRINLDSNTRSFIVPIITTEYIREKLSYSFYGSGGTYALSLSQYNMGINIELSESD
VWIIDVDNVVRDVTIESDKIKKGDLIEGILSTLSIEENKIILNSHEINFSGEVNGSNG -continued

| SEQ ID NOs |
| --- |

FVSLTFSILEGINAIIEVDLLSKSYKLLISGELKILMLNSNHIQQKIDYIGFNSELQKN
IPYSFVDSEGKENGFINGSTKEGLFVSELPDVVLISKVYMDDSKPSFGYYSNNLKD
VKVITKDNVNILTGYYLKDDIKISLSLTLQDEKTIKLNSVHLDESGVAEILKFMNR
KGNTNTSDSLMSFLESMNIKSIFVNFLQSNIKFILDANFIISGTTSIGQFEFICDENDN
IQPYFIKFNTLETNYTLYVGNRQNMIVEPNYDLDDSGDISSTVINFSQKYLYGIDS
CVNKVVISPNIYTDEINITPVYETNNTYPEVIVLDANYINEKINVNINDLSIRYVWS
NDGNDFILMSTSEENKVSQVKIRFVNVFKDKTLANKLSFNFSDKQDVPVSEIILSF
TPSYYEDGLIGYDLGLVSLYNEKFYINNFGMMVSGLIYINDSLYYFKPPVNNLITG
FVTVGDDKYYFNPINGGAASIGETIIDDKNYYFNQSGVLQTGVFSTEDGFKYFAP
ANTLDENLEGEAIDFTGKLIIDENIYYFDDNYRGAVEWKELDGEMHYFSPETGKA
FKGLNQIGDYKYYFNSDGVMQKGFVSINDNKHYFDDSGVMKVGYTEIDGKHFY
FAENGEMQIGVFNTEDGFKYFAHHNEDLGNEEGEEISYSGILNFNNKIYYFDDSFT
AVVGWKDLEDGSKYYFDEDTAEAYIGLSLINDGQYYFNDDGIMQVGFVTINDK
VFYFSDSGIIESGVQNIDDNYFYIDDNGIVQIGVFDTSDGYKYFAPANTVNDNIYG
QAVEYSGLVRVGEDVYYFGETYTIETGWIYDMENESDKYYFNPETKKACKGINL
IDDIKYYFDEKGIMRTGLISFENNNYYFNENGEMQFGYINIEDKMFYFGEDGVMQ
IGVFNTPDGFKYFAHQNTLDENFEGESINYTGWLDLDEKRYYFTDEYIAATGSVII
DGEEYYFDPDTAQLVISE

SEQ ID NO: 14 - Toxin B fragment - TxB 4 (Toxinotype 3)(Residues 767-2366)
SIIKDISSKEYISFNPKENKIIVKSKNLPELSTLLQEIRNNSNSSDIELEEKVMLAECE
INVISNIDTQVVEGRIEEAKSLTSDSINYIKNEFKLIESISDALYDLKQQNELEESHFI
SFEDILETDEGFSIRFIDKETGESIFVETEKAIFSEYANHITEEISKIKGTIFDTVNGKL
VKKVNLDATHEVNTLNAAFFIQSLIEYNSSKESLSNLSVAMKVQVYAQLFSTGLN
TITDAAKVVELVSTALDETIDLLPTLSEGLPVIATIIDGVSLGAAIKELSETSDPLLR
QEIEAKIGIMAVNLTAATTAIITSSLGIASGFSILLVPLAGISAGIPSLVNNELILRDK
ATKVVDYFSHISLAESEGAFTSLDDKIMMPQDDLVISEIDFNNNSITLGKCEIWRM
EGGSGHTVTDDIDHFFSAPSITYREPHLSIYDVLEVQKEELDLSKDLMVLPNAPNR
VFAWETGWTPGLRSLENDGTKLLDRIRDNYEGEFYWRYFAFIADALITTLKPRYE
DTNIRINLDSNTRSFIVPVITTEYIREKLSYSFYGSGGTYALSLSQYNMNINIELNEN
DTWVIDVDNVVRDVTIESDKIKKGDLIENILSKLSIEDNKIILDNHEINFSGTLNGG
NGFVSLTFSILEGINAVIEVDLLSKSYKVLISGELKTLMANSNSVQQKIDYIGLNSE
LQKNIPYSFMDDKGKENGFINCSTKEGLFVSELSDVVLISKVYMDNSKPLFGYCS
NDLKDVKVITKDDVIILTGYYLKDDIKISLSFTIQDENTIKLNGVYLDENGVAEILK
FMNKKGSTNTSDSLMSFLESMNIKSIFINSLQSNTKLILDTNFIISGTTSIGQFEFICD
KDNNIQPYFIKFNTLETKYTLYVGNRQNMIVEPNYDLDDSGDISSTVINFSQKYLY
GIDSCVNKVIISPNIYTDEINITPIYEANNTYPEVIVLDTNYISEKININIDLSIRYV
WSNDGSDFILMSTDEENKVSQVKIRFTNVFKGNTISDKISFNFSDKQDVSINKVIST
FTPSYYVEGLLNYDLGLISLYNEKFYINNFGMMVSGLVYINDSLYYFKPPIKNLIT
GFTTIGDDKYYFNPDNGGAASVGETIIDGKNYYFSQNGVLQTGVFSTEDGFKYFA
PADTLDENLEGEAIDFTGKLTIDENVYYFGDNYRAAIEWQTLDDEVYYFSTDTGR
AFKGLNQIGDDKFYFNSDGIMQKGFVNINDKTFYFDDSGVMKSGYTEIDGKYFY
FAENGEMQIGVFNTADGFKYFAHHDEDLGNEEGEALSYSGILNFNNKIYYFDDSF
TAVVGWKDLEDGSKYYFDEDTAEAYIGISIINDGKYYFNDSGIMQIGFVTINNEVF
YFSDSGIVESGMQNIDDNYFYIDENGLVQIGVFDTSDGYKYFAPANTVNDNIYGQ
AVEYSGLVRVGEDVYYFGETYTIETGWIYDMENESDKYYFDPETKKAYKGINVI
DDIKYYFDENGIMRTGLITFEDNHYYFNEDGIMQYGYLNIEDKTFYFSEDGIMQIG
VFNTPDGFKYFAHQNTLDENFEGESINYTGWLDLDEKRYYFTDEYIAATGSVIID
GEEYYFDPDTAQLVISE SEQ ID NO: 15 - Toxin B fragment - Toxin B-A hybrid (toxinotype 0)
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL
ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLVTGWQTINGKKY
YFDINTGAALISYKIINGKHFYFNNDGVMQLGVFKGPDGFEYFAPANTQNNNIEG
QAIVYQSKFLTLNGKKYYFDNDSKAVTGWRIINNEKYYFNPNNAIAAVGLQVID
NNKYYFNPDTAIISKGWQTVNGSRYYFDTDTAIAFNGYKTIDGKHFYFDSDCVV
KIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG -continued

| SEQ ID NOs |
|---|

IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
IAATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG

SEQ ID NO: 16 - Toxin B fragment - Toxin A-B hybrid (toxinotype 0)
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
ILKKELEAKVGVLAINMSLSIAATVASIVGIGAEVTIFLLPIAGISAGIPSLVNNELIL
HDKATSVVNYFNHLSESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYSPDGAGGTYSLLLSSYPISTNINLSKD
DLWIFNIDNEVREISIENGTIKKGKLIKDVLSKIDINKNKLIIGNQTIDFSGDIDNKD
RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
IKNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLITGFV
TVGDDKYYFNPINGGAASIGETIIDDKNYYFNQSGVLQTGVFSTEDGFKYFAPAN
TLDENLEGEAIDFTGKLIIDENIYYFDDNYRGAVEWKELDGEMHYFSPETGKAFK
GLNQIGDYKYYFNSDGVMQKGFVSINDNKHYFDDSGVMKVGYTEIDGKHFYFA
ENGEMQIGVFNTEDGFKYFAHHNEDLGNEEGEEISYSGILNFNNKIYYFDDSFTA
VVGWKDLEDGSKYYFDEDTAEAYIGLSLINDGQYYFNDDGIMQVGFVTINDKVF
YFSDSGRESGVQNIDDNYFYIDDNGIVQIGVFDTSDGYKYFAPANTVNDNIYGQA
VEYSGLVRVGEDVYYFGETYTIETGWIYDMENESDKYYFNPETKKACKGINLID
DIKYYFDEKGIMRTGLISFENNNYYFNENGEMQFGYINIEDKMFYFGEDGVMQIG
VFNTPDGFKYFAHQNTLDENFEGESINYTGWLDLDEKRYYFTDEYIAATGSVIID
GEEYYFDPDTAQLVISE SEQ ID NO: 17 - Toxin B fragment - Toxin A-B hybrid (toxinotype 0 and 3)
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
LKKELEAKVGVLAINMSLSIAATVASIVGIGAEVTIFLLPIAGISAGIPSLVNNELIL
HDKATSVVNYFNHLSESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYS14DGAGGTYSLLLSSYPISTNINLSKD
DLWIFNIDNEVREISIENGTIKKGKLIKDVLSKIDINKNKLIIGNQTIDFSGDIDNKD
RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
KNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLITGFT
TIGDDKYYFNPDNGGAASVGETIIDGKNYYFSQNGVLQTGVFSTEDGFKYFAPA
DTLDENLEGEAIDFTGKLTIDENVYYFGDNYRAAIEWQTLDDEVYYFSTDTGRAF
KGLNQIGDDKFYFNSDGIMQKGFVNINDKTFYFDDSGVMKSGYTEIDGKYFYFA
ENGEMQIGVFNTADGFKYFAHHDEDLGNEEGEALSYSGILNFNNKIYYFDDSFTA
VVGWKDLEDGSKYYFDEDTAEAYIGISIINDGKYYFNDSGIMQIGFVTINNEVFYF
SDSGIVESGMQNIDDNYFYIDENGLVQIGVFDTSDGYKYFAPANTVNDNIYGQAV
EYSGLVRVGEDVYYFGETYTIETGWIYDMENESDKYYFDPETKKAYKGINVIDDI
KYYFDENGIMRTGLITFEDNHYYFNEDGIMQYGYLNIEDKTFYFSEDGIMQIGVF
NTPDGFKYFAHQNTLDENFEGESINYTGWLDLDEKRYYFTDEYIAATGSVIIDGE
EYYFDPDTAQLVISE SEQ ID NO: 18 - Toxin A-derived recombinant antigen His-NusA-[thrombin site]-TxA4-His
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI -continued

| SEQ ID NOs |
|---|
| GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAAPFTMIMSDLSSKEYIFFD<br>SIDNKLKAKSKNIPGLASISEDIKTLLLDASVSPDTKFILNNLKLNIESSIGDYIYYE<br>KLEPVKNIIHNSIDDLIDEFNLLENVSDELYELKKLNNLDEKYLISFEDISKNNSTY<br>SVRFINKSNGESVYVETEKEIFSKYSEHITKEISTIKNSIITDVNGNLLDNIQLDHTS<br>QVNTLNAAFFIQSLIDYSSNKDVLNDLSTSVKVQLYAQLFSTGLNTIYDSIQLVNL<br>ISNAVNDTINVLPTITEGIPIVSTILDGINLGAAIKELLDEHDPLLKKELEAKVGVLA<br>INMSLSIAATVASIVGIGAEVTIFLLPIAGISAGIPSLVNNELILHDKATSVVNYFNH<br>LSESKKYGPLKTEDDKILVPIDDLVISEIDFNNNSIKLGTCNILAMEGGSGHTVTGN<br>IDHFFSSPSISSHIPSLSIYSAIGIETENLDFSKKIMMLPNAPSRVFWWETGAVPGLR<br>SLENDGTRLLDSIRDLYPGKFYWRFYAFFDYAITTLKPVYEDTNIKIKLDKDTRNF<br>IMPTITTNEIRNKLSYSFDGAGGTYSLLLSSYPISTNINLSKDDLWIFNIDNEVREISI<br>ENGTIKKGKLIKDVLSKIDINKNKLIIGNQTIDFSGDIDNKDRYIFLTCELDDKISLII<br>EINLVAKSYSLLLSGDKNYLISNLSNIIEKINTLGLDSKNIAYNYTDESNNKYFGAI<br>SKTSQKSIIHYKKDSKNILEFYNDSTLEFNSKDFIAEDINVFMKDDINTITGKYYVD<br>NNTDKSIDFSISLVSKNQVKVNGLYLNESVYSSYLDFVKNSDGHHNTSNFMNLFL<br>DNISFWKLFGFENINFVIDKYFTLVGKTNLGYVEFICDNNKNIDIYFGEWKTSSSK<br>ISTIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNK<br>KILQKIRIKGILSNTQSFNKMSIDFKDIKKLSLGYIMSNFKSFNSENELDRDHLGFKI<br>IDNKTYYYDEDSKLVKGLININNSLFYFDPIEFNLVTGWQTINGKKYYFDINTGAA<br>LISYKIINGKHFYFNNDGVMQLGVFKGPDGFEYFAPANTQNNNIEGQAIVYQSKF<br>LTLNGKKYYFDNDSKAVTGWRIINNEKYYFNPNNAIAAVGLQVIDNNKYYFNPD<br>TAIISKGWQTVNGSRYYFDTDTAIAFNGYKTIDGKHFYFDSDCVVKIGVFSTSNG<br>FEYFAPANTYNNNIEGQAIVYQSKFLTLNGKKYYFDNNSKAVTGWQTIDSKKYY<br>FNTNTAEAATGWQTIDGKKYYFNTNTAEAATGWQTIDGKKYYFNTNTAIASTG<br>YTIINGKHFYFNTDGIMQIGVFKGPNGFEYFAPANTDANNIEGQAILYQNEFLTLN<br>IGKKYYFGSDSKAVTGWRIINNKKYYFNPNNAIAAIHLCTINNDKYYFSYDGILQN<br>GYITIERNNFYFDANNESKMVTGVFKGPNGFEYFAPANTHNNNIEGQAIVYQNKF<br>LTLNGKKYYFDNDSKAVTGWQTIDGKKYYFNLNTAEAATGWQTIDGKKYYFNL<br>NTAEAATGWQTIDGKKYYFNTNTFIASTGYTSINGKHFYFNTDGIMQIGVFKGPN<br>GFEYFAPANTHNNNIEGQAILYQNKFLTLNGKKYYFGSDSKAVTGLRTIDGKKY<br>YFNTNTAVAVTGWQTINGKKYYFNTNTSIASTGYTIISGKHFYFNTDGIMQIGVF<br>KGPDGFEYFAPANTDANNIEGQAIRYQNRFLYLHDNIYYFGNNSKAATGWVTID<br>GNRYYFEPNTAMGANGYKTIDNKNFYFRNGLPQIGVFKGSNGFEYFAPANTDAN<br>NIEGQAIRYQNRFLHLLGKIYYFGNNSKAVTGWQTINGKVYYFMPDTAMAAAG<br>GLFEIDGVIYFFGVDGVKAPGIYGGGSGGSLVPRGSGGSHHHHHH<br><br>SEQ ID NO: 19 - Toxin A-derived recombinant antigen His-NusA-[thrombin site]-TxA4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAAPFTMIMSDLSSKEYIFFD<br>SIDNKLKAKSKNIPGLASISEDIKTLLLDASVSPDTKFILNNLKLNIESSIGDYIYYE<br>KLEPVKNIIHNSIDDLIDEFNLLENVSDELYELKKLNNLDEKYLISFEDISKNNSTY<br>SVRFINKSNGESVYVETEKEIFSKYSEHITKEISTIKNSIITDVNGNLLDNIQLDHTS<br>QVNTLNAAFFIQSLIDYSSNKDVLNDLSTSVKVQLYAQLFSTGLNTIYDSIQLVNL<br>ISNAVNDTINVLPTITEGIPIVSTILDGINLGAAIKELLDEHDPLLKKELEAKVGVLA<br>INMSLSIAATVASIVGIGAEVTIFLLPIAGISAGIPSLVNNELILHDKATSVVNYFNH<br>LSESKKYGPLKTEDDKILVPIDDLVISEIDFNNNSIKLGTCNILAMEGGSGHTVTGN<br>IDHFFSSPSISSHIPSLSIYSAIGIETENLDFSKKIMMLPNAPSRVFWWETGAVPGLR<br>SLENDGTRLLDSIRDLYPGKFYWRFYAFFDYAITTLKPVYEDTNIKIKLDKDTRNF<br>IMPTITTNEIRNKLSYSFDGAGGTYSLLLSSYPISTNINLSKDDLWIFNIDNEVREISI<br>ENGTIKKGKLIKDVLSKIDINKNKLIIGNQTIDFSGDIDNKDRYIFLTCELDDKISLII<br>EINLVAKSYSLLLSGDKNYLISNLSNIIEKINTLGLDSKNIAYNYTDESNNKYFGAI<br>SKTSQKSIIHYKKDSKNILEFYNDSTLEFNSKDFIAEDINVFMKDDINTITGKYYVD<br>NNTDKSIDFSISLVSKNQVKVNGLYLNESVYSSYLDFVKNSDGHHNTSNFMNLFL<br>DNISFWKLFGFENINFVIDKYFTLVGKTNLGYVEFICDNNKNIDIYFGEWKTSSSK<br>STIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNK<br>KILQKIRIKGILSNTQSFNKMSIDFKDIKKLSLGYIMSNFKSFNSENELDRDHLGFKI<br>IDNKTYYYDEDSKLVKGLININNSLFYFDPIEFNLVTGWQTINGKKYYFDINTGAA<br>LISYKIINGKHFYFNNDGVMQLGVFKGPDGFEYFAPANTQNNNIEGQAIVYQSKF<br>LTLNGKKYYFDNDSKAVTGWRIINNEKYYFNPNNAIAAVGLQVIDNNKYYFNPD<br>TAIISKGWQTVNGSRYYFDTDTAIAFNGYKTIDGKHFYFDSDCVVKIGVFSTSNG<br>FEYFAPANTYNNNIEGQAIVYQSKFLTLNGKKYYFDNNSKAVTGWQTIDSKKYY<br>FNTNTAEAATGWQTIDGKKYYFNTNTAEAATGWQTIDGKKYYFNTNTAIASTG<br>YTIINGKHFYFNTDGIMQIGVFKGPNGFEYFAPANTDANNIEGQAILYQNEFLTLN<br>GKKYYFGSDSKAVTGWRIINNKKYYFNPNNAIAAIHLCTINNDKYYFSYDGILQN |

-continued

| SEQ ID NOs |
|---|
| GYITIERNNFYFDANNESKMVTGVFKGPNGFEYFAPANTHNNNIEGQAIVYQNKF<br>LTLNGKKYYFDNDSKAVTGWQTIDGKKYYFNLNTAEAATGWQTIDGKKYYFNL<br>NTAEAATGWQTIDGKKYYFNTNTFIASTGYTSINGKHFYFNTDGIMQIGVFKGPN<br>GFEYFAPANTHNNNIEGQAILYQNKFLTLNGKKYYFGSDSKAVTGLRTIDGKKY<br>YFNTNTAVAVTGWQTINGKKYYFNTNTSIASTGYTIISGKHFYFNTDGIMQIGVF<br>KGPDGFEYFAPANTDANNIEGQAIRYQNRFLYLHDNIYYFGNNSKAATGWVTID<br>GNRYYFEPNTAMGANGYKTIDNKNFYFRNGLPQIGVFKGSNGFEYFAPANTDAN<br>NIEGQAIRYQNRFLHLLGKIYYFGNNSKAVTGWQTINGKVYYFMPDTAMAAAG<br>GLFEIDGVIYFFGVDGVKAPGIYG |
| SEQ ID NO: 20 - Toxin A-derived recombinant antigen - His-Thioredoxin-[thrombin site]-TxA4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAAPFTMIMSDLSSKEYIFFDSIDNKLK<br>AKSKNIPGLASISEDIKTLLLDASVSPDTKFILNNLKLNIESSIGDYIYYEKLEPVKN<br>IIHNSIDDLIDEFNLLENVSDELYELKKLNNLDEKYLISFEDISKNNSTYSVRFINKS<br>NGESVYVETEKEIFSKYSEHITKEISTIKNSIITDVNGNLLDNIQLDHTSQVNTLNA<br>AFFIQSLIDYSSNKDVLNDLSTSVKVQLYAQLFSTGLNTIYDSIQLVNLISNAVNDT<br>INVLPTITEGIPIVSTILDGINLGAAIKELLDEHDPLLKKELEAKVGVLAINMSLSIA<br>ATVASIVGIGAEVTIFLLPIAGISAGIPSLVNNELILHDKATSVVNYFNHLSESKKY<br>GPLKTEDDKILVPIDDLVISEIDFNNNSIKLGTCNILAMEGGSGHTVTGNIDHFFSS<br>PSISSHIPSLSIYSAIGIETENLDFSKKIMMLPNAPSRVFWWETGAVPGLRSLENDG<br>TRLLDSIRDLYPGKFYWRFYAFFDYAITTLKPVYEDTNIKIKLDKDTRNFIMPTITT<br>NEIRNKLSYSFDGAGGTYSLLLSSYPISTNINLSKDDLWIFNIDNEVREISIENGTIK<br>KGKLIKDVLSKIDINKNKLIIGNQTIDFSGDIDNKDRYIFLTCELDDKISLIIEINLVA<br>KSYSLLLSGDKNYLISNLSNIIEKINTLGLDSKNIAYNYTDESNNKYFGAISKTSQK<br>SIIHYKKDSKNILEFYNDSTLEFNSKDFIAEDINVFMKDDINTITGKYYVDNNTDK<br>SIDFSISLVSKNQVKVNGLYLNESVYSSYLDFVKNSDGHHNTSNFMNLFLDNISF<br>WKLFGFENINFVIDKYFTLVGKTNLGYVEFICDNNKNIDIYFGEWKTSSSKSTIFS<br>GNGRNVVVEPIYNPDTGEDISTSLDFSYEPLYGIDRYINKVLIAPDLYTSLININTN<br>YYSNEYYPEIIVLNPNTFHKKVNINLDSSSFENKWSTEGSDFILVRYLEESNKKILQ<br>KIRIKGILSNTQSFNKMSIDFKDIKKLSLGYIMSNFKSFNSENELDRDHLGFKIIDN<br>KTYYYDEDSKLVKGLININNSLFYFDPIEFNLVTGWQTINGKKYYFDINTGAALIS<br>YKIINGKHFYFNNDGVMQLGVFKGPDGFEYFAPANTQNNNIEGQAIVYQSKFLTL<br>NGKKYYFDNDSKAVTGWRIINNEKYYFNPNNAIAAVGLQVIDNNKYYFNPDTAI<br>ISKGWQTVNGSRYYFDTDTAIAFNGYKTIDGKHFYFDSDCVVKIGVFSTSNGFEN<br>FAPANTYNNNIEGQAIVYQSKFLTLNGKKYYFDNNSKAVTGWQTIDSKKYYFNT<br>NTAEAATGWQTIDGKKYYFNTNTAEAATGWQTIDGKKYYFNTNTAIASTGYTII<br>NGKHFYFNTDGIMQIGVFKGPNGFEYFAPANTDANNIEGQAILYQNEFLTLNGKK<br>YYFGSDSKAVTGWRIINNKKYYFNPNNAIAAIHLCTINNDKYYFSYDGILQNGYI<br>TIERNNFYFDANNESKMVTGVFKGPNGFEYFAPANTHNNNIEGQAIVYQNKFLTL<br>NGKKYYFDNDSKAVTGWQTIDGKKYYFNLNTAEAATGWQTIDGKKYYFNLNT<br>AEAATGWQTIDGKKYYFNTNTFIASTGYTSINGKHFYFNTDGIMQIGVFKGPNGF<br>EYFAPANTHNNNIEGQAILYQNKFLTLNGKKYYFGSDSKAVTGLRTIDGKKYYF<br>NTNTAVAVTGWQTINGKKYYFNTNTSIASTGYTIISGKHFYFNTDGIMQIGVFKG<br>PDGFEYFAPANTDANNIEGQAIRYQNRFLYLHDNIYYFGNNSKAATGWVTIDGN<br>RYYFEPNTAMGANGYKTIDNKNFYFRNGLPQIGVFKGSNGFEYFAPANTDANNI<br>EGQAIRYQNRFLHLLGKIYYFGNNSKAVTGWQTINGKVYYFMPDTAMAAAGGL<br>FEIDGVIYFFGVDGVKAPGIYG |
| SEQ ID NO: 21 - Toxin A-derived recombinant antigen - His-Thioredoxin-[thrombin site]-TxA3<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAAPFTMESKKYGPLKTEDDKILVPIDD<br>LVISEIDFNNNSIKLGTCNILAMEGGSGHTVTGNIDHFFSSPSISSHIPSLSIYSAIGIE<br>TENLDFSKKIMMLPNAPSRVFWWETGAVPGLRSLENDGTRLLDSIRDLYPGKFY<br>WRFYAFFDYAITTLKPVYEDTNIKIKLDKDTRNFIMPTITTNEIRNKLSYSFDGAG<br>GTYSLLLSSYPISTNINLSKDDLWIFNIDNEVREISIENGTIKKGKLIKDVLSKIDINK<br>NKLIIGNQTIDFSGDIDNKDRYIFLTCELDDKISLIIEINLVAKSYSLLLSGDKNYLIS<br>NLSNIIEKINTLGLDSKNIAYNYTDESNNKYFGAISKTSQKSIIHYKKDSKNILEFY<br>NDSTLEFNSKDFIAEDINVFMKDDINTITGKYYVDNNTDKSIDFSISLVSKNQVKV<br>NGLYLNESVYSSYLDFVKNSDGHHNTSNFMNLFLDNISFWKLFGFENINFVIDKY<br>FTLVGKTNLGYVEFICDNNKNIDIYFGEWKTSSSKSTIFSGNGRNVVVEPIYNPDT<br>GEDISTSLDFSYEPLYGIDRYINKVLIAPDLYTSLININTNYYSNEYYPEIIVLNPNTF<br>HKKVNINLDSSSFEYKWSTEGSDFILVRYLEESNKKILQKIRIKGILSNTQSFNKMS<br>IDFKDIKKLSLGYIMSNFKSFNSENELDRDHLGFKIIDNKTYYYDEDSKLVKGLINI<br>NNSLFYFDPIEFNLVTGWQTINGKKYYFDINTGAALISYKIINGKHFYFNNDGVM<br>QLGVFKGPDGFEYFAPANTQNNNIEGQAIVYQSKFLTLNGKKYYFDNDSKAVTG<br>WRIINNEKYYFNPNNAIAAVGLQVIDNNKYYFNPDTAIISKGWQTVNGSRYYFDT<br>DTAIAFNGYKTIDGKHFYFDSDCVVKIGVFSTSNGFEYFAPANTYNNNIEGQAIV<br>YQSKFLTLNGKKYYFDNNSKAVTGWQTIDSKKYYFNTNTAEAATGWQTIDGKK<br>YYFNTNTAEAATGWQTIDGKKYYFNTNTAIASTGYTIINGKHFYFNTDGIMQIGV<br>FKGPNGFENFAPANTDANNIEGQAILYQNEFLTLNGKKYYFGSDSKAVTGWRIIN<br>NKKYYFNPNNAIAAIHLCTINNDKYYFSYDGILQNGYITIERNNFYFDANNESKM<br>VTGVFKGPNGFEYFAPANTHNNNIEGQAIVYQNKFLTLNGKKYYFDNDSKAVTG |

-continued

SEQ ID NOs

WQTIDGKKYYFNLNTAEAATGWQTIDGKKYYFNLNTAEAATGWQTIDGKKYYF
NTNTFIASTGYTSINGKHFYFNTDGIMQIGVFKGPNGFEYFAPANTHNNNIEGQAI
LYQNKFLTLNGKKYYFGSDSKAVTGLRTIDGKKYYFNTNTAVAVTGWQTINGK
KYYFNTNTSIASTGYTIISGKHFYFNTDGIMQIGVFKGPDGFEYFAPANTDANNIE
GQAIRYQNRFLYLHDNIYYFGNNSKAATGWVTIDGNRYYFEPNTAMGANGYKTI
DNKNFYFRNGLPQIGVFKGSNGFEYFAPANTDANNIEGQAIRYQNRFLHLLGKIY
YFGNNSKAVTGWQTINGKVYYFMPDTAMAAAGGLFEIDGVIYFFGVDGVKAPG
IYG

SEQ ID NO: 22 - Toxin A-derived recombinant antigen - His-NusA-[thrombin site]-TxA3
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAAPFTMESKKYGPLKTEDD
KILVPIDDLVISEIDFNNNSIKLGTCNILAMEGGSGHTVTGNIDHFFSSPSISSHIPSL
SIYSAIGIETENLDFSKKIMMLPNAPSRVFWWETGAVPGLRSLENDGTRLLDSIRD
LYPGKFYWRFYAFFDYAITTLKPVYEDTNIKIKLDKDTRNFIMPTITTNEIRNKLS
YSPDGAGGTYSLLLSSYPISTNINLSKDDLWIFNIDNEVREISIENGTIKKGKLIKDV
LSKIDINKNKLIIGNQTIDFSGDIDNKDRYIFLTCELDDKISLIIEINLVAKSYSLLLS
GDKNYLISNLSNIIEKINTLGLDSKNIAYNYTDESNNKYFGAISKTSQKSIIHYKKD
SKNILEFYNDSTLEFNSKDFIAEDINVFMKDDINTITGKYYVDNNTDKSIDFSISLV
SKNQVKVNGLYLNESVYSSYLDFVKNSDGHHNTSNFMNLFLDNISFWKLFGFEN
INFVIDKYFTLVGKTNLGYVEFICDNNKNIDIYFGEWKTSSSKSTIFSGNGRNVVV
EPIYNPDTGEDISTSLDFSYEPLYGIDRYINKVLIAPDLYTSLININTNYYSNEYYPEI
IVLNPNTFHKKVNINLDSSSFEYKWSTEGSDFILVRYLEESNKKILQKIRIKGILSNT
QSFNKMSIDFKDIKKLSLGYIMSNFKSFNSENELDRDHLGFKIIDNKTYYYDEDSK
LVKGLININNSLFYFDPIEFNLVTGWQTINGKKYYFDINTGAALISYKIINGKHFYF
NNDGVMQLGVFKGPDGFEYFAPANTQNNNIEGQAIVYQSKFLTLNGKKYYFDN
DSKAVTGWRIINNEKYYFNPNNAIAAVGLQVIDNNKYYFNPDTAIISKGWQTVN
GSRYYPDTDTAIAFNGYKTIDGKHFYFDSDCVVKIGVFSTSNGFEYFAPANTYNN
NIEGQAIVYQSKFLTLNGKKYYIDNNSKAVTGWQTIDSKKYYFNTNTAEAATG
WQTIDGKKYYFNTNTAEAATGWQTIDGKKYYFNTNTAIASTGYTIINGKHFYFN
TDGIMQIGVFKGPNGFEYFAPANTDANNIEGQAILYQNEFLTLNGKKYYFGSDSK
AVTGWRIINNKKYYFNPNNAIAAIHLCTINNDKYYFSYDGILQNGYITIERNNFYF
DANNESKMVTGVFKGPNGFEYFAPANTHNNNIEGQAIVYQNKFLTLNGKKYYF
DNDSKAVTGWQTIDGKKYYFNLNTAEAATGWQTIDGKKYYFNLNTAEAATGW
QTIDGKKYYFNTNTFIASTGYTSINGKHFYFNTDGIMQIGVFKGPNGFEYFAPANT
HNNNIEGQAILYQNKFLTLNGKKYYFGSDSKAVTGLRTIDGKKYYFNTNTAVAV
TGWQTINGKKYYFNTNTSIASTGYTIISGKHFYFNTDGIMQIGVFKGPDGFEYFAP
ANTDANNIEGQAIRYQNRFLYLHDNIYYFGNNSKAATGWVTIDGNRYYFEPNTA
MGANGYKTIDNKNFYFRNGLPQIGVFKGSNGFEYFAPANTDANNIEGQAIRYQN
RFLHLLGKIYYFGNNSKAVTGWQTINGKVYYFMPDTAMAAAGGLFEIDGVIYFF
GVDGVKAPGIYG SEQ ID NO: 23 - Toxin B-derived recombinant antigen - His-NusA-[thrombin site]-TxB4-His
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAAPFTMSIIKDISSKEYISFN
PKENKITVKSKNLPELSTLLQEIRNNSNSSDIELEEKVMLTECEINVISNIDTQIVEE
RIEEAKNLTSDSINYIKDEFKLIESISDALCDLKQQNELEDSHFISFEDISETDEGFSI
RFINKETGESIFVETEKTIFSEYANHITEEISKIKGTIFDTVNGKLVKKVNLDTTHEV
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL -continued

| SEQ ID NOs |
| --- |

ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLITGFVTVGDDKYY
FNPINGGAASIGETIIDDKNYYFNQSGVLQTGVFSTEDGFKYFAPANTLDENLEGE
AIDFTGKLIIDENIYYFDDNYRGAVEWKELDGEMHYFSPETGKAFKGLNQIGDYK
YYFNSDGVMQKGFVSINDNKHYFDDSGVMKVGYTEIDGKHFYFAENGEMQIGV
FNTEDGFKYFAHHNEDLGNEEGEEISYSGILNFNNKIYYFDDSFTAVVGWKDLED
GSKYYFDEDTAEAYIGLSLINDGQYYFNDDGIMQVGFVTINDKVFYFSDSGIIESG
VQNIDDNYFYIDDNGIVQIGVFDTSDGYKYFAPANTVNDNIYGQAVEYSGLVRV
GEDVYYFGETYTIETGWIYDMENESDKYYFNPETKKACKGINLIDDIKYYFDEKG
IMRTGLISFENNNYYFNENGEMQFGYINIEDKMFYFGEDGVMQIGVFNTPDGFKY
FAHQNTLDENFEGESINYTGWLDLDEKRYYFTDEYIAATGSVIIDGEEYYPDPDT
AQLVISEGHHHHHH

SEQ ID NO: 24 - Toxin B-derived recombinant antigen - His-NusA-[thrombin site]-TxB4
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAAPFTMSIIKDISSKEYISFN
PKENKITVKSKNLPELSTLLQEIRNNSNSSDIELEEKVMLTECEINVISNIDTQIVEE
RIEEAKNLTSDSINYIKDEFKLIESISDALCDLKQQNELEDSHFISFEDISETDEGFSI
RFINKETGESIFVETEKTIFSEYANHITEEISKIKGTIFDTVNGKLVKKVNLDTTHEV
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL
ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLITGFVTVGDDKYY
FNPINGGAASIGETIIDDKNYYFNQSGVLQTGVFSTEDGFKYFAPANTLDENLEGE
AIDFTGKLIIDENIYYFDDNYRGAVEWKELDGEMHYFSPETGKAFKGLNQIGDYK
YYFNSDGVMQKGFVSINDNKHYFDDSGVMKVGYTEIDGKHFYFAENGEMQIGV
FNTEDGFKYFAHHNEDLGNEEGEEISYSGILNFNNKIYYFDDSFTAVVGWKDLED
GSKYYFDEDTAEAYIGLSLINDGQYYFNDDGIMQVGFVTINDKVFYFSDSGIIESG
VQNIDDNYFYIDDNGIVQIGVFDTSDGYKYFAPANTVNDNIYGQAVEYSGLVRV
GEDVYYFGETYTIETGWIYDMENESDKYYFNPETKKACKGINLIDDIKYYFDEKG
IMRTGLISFENNNYYFNENGEMQFGYINIEDKMFYFGEDGVMQIGVFNTPDGFKY
FAHQNTLDENFEGESINYTGWLDLDEKRYYFTDEYIAATGSVIIDGEEYYFDPDT
AQLVISE SEQ ID NO: 25 - Toxin B-derived recombinant antigen - His-Thioredoxin-[thrombin site]-TxB 4
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALVPRGSVTSLYKKAGSAAAPFTMSIIKDISSKEYISFNPKENKITV
KSKNLPELSTLLQEIRNNSNSSDIELEEKVMLTECEINVISNIDTQIVEERIEEAKNL
TSDSINYIKDEFKLIESISDALCDLKQQNELEDSHFISFEDISETDEGFSIRFINKETG
ESIFVETEKTIFSEYANHITEEISKIKGTIFDTVNGKLVKKVNLDTTHEVNTLNAAF
FIQSLIEYNSSKESLSNLSVAMKVQVYAQLFSTGLNTITDAAKVVELVSTALDETI
DLLPTLSEGLPIIATIIDGVSLGAAIKELSETSDPLLRQEIEAKIGIMAVNLTTATTAII
TSSLGIASGFSILLVPLAGISAGIPSLVNNELVLRDKATKVVDYFKHVSLVETEGVF
TLLDDKIMMPQDDLVISEIDFNNNSIVLGKCEIWRMEGGSGHTVTDDIDHFFSAPS
ITYREPHLSIYDVLEVQKEELDLSKDLMVLPNAPNRVFAWETGWTPGLRSLEND
GTKLLDRIRDNYEGEFYWRYFAFIADALITTLKPRYEDTNIRINLDSNTRSFIVPIIT
TEYIREKLSYSFYGSGGTYALSLSQYNMGINIELSESDVWIIDVDNVVRDVTIESD
KIKKGDLIEGILSTLSIEENKIILNSHEINFSGEVNGSNGFVSLTFSILEGINAIIEVDL
LSKSYKLLISGELKILMLNSNHIQQKIDYIGFNSELQKNIPYSFVDSEGKENGFING
STKEGLFVSELPDVVLISKVYMDDSKPSFGYYSNNLKDVKVITKDNVNILTGYYL
KDDIKISLSLTLQDEKTIKLNSVHLDESGVAEILKFMNRKGNTNTSDSLMSFLESM
NIKSIFVNFLQSNIKFILDANFIISGTTSIGQFEFICDENDNIQPYFIKFNTLETNYTLY
VGNRQNMIVEPNYDLDDSGDISSTVINFSQKYLYGIDSCVNKVVISPNIYTDEINIT -continued

| SEQ ID NOs |
|---|

PVYETNNTYPEVIVLDANYINEKINVNINDLSIRYVWSNDGNDFILMSTSEENKVS
QVKIRFVNVFKDKTLANKLSFNFSDKQDVPVSEIILSFTPSYYEDGLIGYDLGLVS
LYNEKFYINNFGMMVSGLIYINDSLYYFKPPVNNLITGFVTVGDDKYYFNPINGG
AASIGETIIDDKNYYFNQSGVLQTGVFSTEDGFKYFAPANTLDENLEGEAIDFTGK
LIIDENIYYFDDNYRGAVEWKELDGEMHYFSPETGKAFKGLNQIGDYKYYFNSD
GVMQKGFVSINDNKHYFDDSGVMKVGYTEIDGKHFYFAENGEMQIGVFNTEDG
FKYFAHHNEDLGNEEGEEISYSGILNFNNKIYYFDDSFTAVVGWKDLEDGSKYYF
DEDTAEAYIGLSLINDGQYYFNDDGIMQVGFVTINDKVFYFSDSGIIESGVQNIDD
NYFYIDDNGIVQIGVFDTSDGYKYFAPANTVNDNIYGQAVEYSGLVRVGEDVYY
FGETYTIETGWIYDMENESDKYYFNPETKKACKGINLIDDIKYYFDEKGIMRTGLI
SFENNNYYFNENGEMQFGYINIEDKMFYFGEDGVMQIGVFNTPDGFKYFAHQNT
LDENFEGESINYTGWLDLDEKRYYFTDEYIAATGSVIIDGEEYYFDPDTAQLVISE

SEQ ID NO: 26 - Toxin B-derived recombinant antigen - His-NusA-[thrombin site]-TxB3
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAGGSMPQDDLVISEIDFNN
NSIVLGKCEIWRMEGGSGHTVTDDIDHFFSAPSITYREPHLSIYDVLEVQKEELDL
SKDLMVLPNAPNRVFAWETGWTPGLRSLENDGTKLLDRIRDNYEGEFYWRYFA
FIADALITTLKPRYEDTNIRINLDSNTRSFIVPIITTEYIREKLSYSFYGSGGTYALSL
SQYNMGINIELSESDVWIIDVDNVVRDVTIESDKIKKGDLIEGILSTLSIEENKIILNS
HEINFSGEVNGSNGFVSLTFSILEGINAIIEVDLLSKSYKLLISGELKILMLNSNHIQ
QKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVH
LDESGVAEILKFMNRKGNTNTSDSLMSFLESMNIKSIFVNFLQSNIKFILDANFIISG
TTSIGQFEFICDENDNIQPYFIKFNTLETNYTLYVGNRQNMIVEPNYDLDDSGDISS
TVINFSQKYLYGIDSCVNKVVISPNIYTDEINITPVYETNNTYPEVIVLDANYINEKI
NVNINDLSIRYVWSNDGNDFILMSTSEENKVSQVKIRFVNVFKDKTLANKLSFNF
SDKQDVPVSEIILSFTPSYYEDGLIGYDLGLVSLYNEKFYINNFGMMVSGLIYINDS
LYYFKPPVNNLITGFVTVGDDKYYFNPINGGAASIGETIIDDKNYYFNQSGVLQT
GVFSTEDGFKYFAPANTLDENLEGEAIDFTGKLIIDENIYYFDDNYRGAVEWKEL
DGEMHYFSPETGKAFKGLNQIGDYKYYFNSDGVMQKGFVSINDNKHYFDDSGV
MKVGYTEIDGKHFYFAENGEMQIGVFNTEDGFKYFAHHNEDLGNEEGEEISYSGI
LNFNNKIYYFDDSFTAVVGWKDLEDGSKYYFDEDTAEAYIGLSLINDGQYYFND
DGIMQVGFVTINDKVFYFSDSGRESGVQNIDDNYFYIDDNGIVQIGVFDTSDGYK
YFAPANTVNDNIYGQAVEYSGLVRVGEDVYYFGETYTIETGWIYDMENESDKY
YFNPETKKACKGINLIDDIKYYFDEKGIMRTGLISFENNNYYFNENGEMQFGYINI
EDKMFYFGEDGVMQIGVFNTPDGFKYFAHQNTLDENFEGESINYTGWLDLDEKR
YYFTDEYIAATGSVIIDGEEYYFDPDTAQLVISE SEQ ID NO: 27 - Toxin B -derived recombinant antigen - His-Thioredoxin-[thrombin site]-
TxB 3 (-hyd)
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALVPRGSVTSLYKKAGSAAGGSMPQDDLVISEIDFNNNSIVLGKC
EIWRMEGGSGHTVTDDIDHFFSAPSITYREPHLSIYDVLEVQKEELDLSKDLMVLP
NAPNRVFAWETGWTPGLRSLENDGTKLLDRIRDNYEGEFYWRYFAFIADALITT
LKPRYEDTNIRINLDSNTRSFIVPIITTEYIREKLSYSFYGSGGTYALSLSQYNMGIN
IELSESDVWIIDVDNVVRDVTIESDKIKKGDLIEGILSTLSIEENKIILNSHEINFSGE
VNGSNGFVSLTFSILEGINAIIEVDLLSKSYKLLISGELKILMLNSNHIQQKIDYIGF
NSELQKNIPYSFVDSEGKENGFINGSTKEGLFVSELPDVVLISKVYMDDSKPSFGY
YSNNLKDVKVITKDNVNILTGYYLKDDIKISLSLTLQDEKTIKLNSVHLDESGVAE
ILKFMNRKGNTNTSDSLMSFLESMNIKSIFVNFLQSNIKFILDANFIISGTTSIGQFEF
ICDENDNIQPYFIKFNTLETNYTLYVGNRQNMIVEPNYDLDDSGDISSTVINFSQK
YLYGIDSCVNKVVISPNIYTDEINITPVYETNNTYPEVIVLDANYINEKINVNINDL
SIRYVWSNDGNDFILMSTSEENKVSQVKIRFVNVFKDKTLANKLSFNFSDKQDVP
VSEIILSFTPSYYEDGLIGYDLGLVSLYNEKFYINNFGMMVSGLIYINDSLYYFKPP
VNNLITGFVTVGDDKYYFNPINGGAASIGETIIDDKNYYFNQSGVLQTGVFSTED
GFKYFAPANTLDENLEGEAIDFTGKLIIDENIYYFDDNYRGAVEWKELDGEMHYF
SPETGKAFKGLNQIGDYKYYFNSDGVMQKGFVSINDNKHYFDDSGVMKVGYTE
IDGKHFYFAENGEMQIGVFNTEDGFKYFAHHNEDLGNEEGEEISYSGILNFNNKI
YYFDDSFTAVVGWKDLEDGSKYYFDEDTAEAYIGLSLINDGQYYFNDDGIMQV
GFVTINDKVFYFSDSGIIESGVQNIDDNYFYIDDNGIVQIGVFDTSDGYKYFAPAN
TVNDNIYGQAVEYSGLVRVGEDVYYFGETYTIETGWIYDMENESDKYYFNPETK
KACKGINLIDDIKYYFDEKGIMRTGLISFENNNYYFNENGEMQFGYINIEDKMFYF
GEDGVMQIGVFNTPDGFKYFAHQNTLDENFEGESINYTGWLDLDEKRYYFTDEY
IAATGSVIIDGEEYYFDPDTAQLVISE -continued

| SEQ ID NOs |
|---|

SEQ ID NO: 28 - Toxin A-derived recombinant antigen - His-[linear spacer]-NusA-[thrombin site]-TxA4
HHHHHHHHHHGGSGGSGGSGGSGGSGGSGGSGGSGGSGGSHMASNKEILAVVEA
VSNEKALPREKIFEALESALATATKKKYEQEIDVRVQIDRKSGDFDTPRRWLVVD
EVTQPTKEITLEAARYEDESLNLGDYVEDQIESVTFDRITTQTAKQVIVQKVREAE
RAMVVDQFREHEGEIITGVVKKVNRDNISLDLGNNAEAVILREDMLPRENFRPG
DRVRGVLYSVRPEARGAQLFVTRSKPEMLIELFRIEVPEIGEEVIEIKAAARDPGSR
AKIAVKTNDKRIDPVGACVGMRGARVQAVSTELGGERIDIVLWDDNPAQFVINA
MAPADVASIVVDEDKHTMDIAVEAGNLAQAIGRNGQNVRLASQLSGWELNVMT
VDDLQAKHQAEAHAAIDTFTKYLDIDEDFATVLVEEGFSTLEELAYVPMKELLEI
EGLDEPTVEALRERAKNALATIAQAQEESLGDNKPADDLLNLEGVDRDLAFKLA
ARGVCTLEDLAEQGIDDLADIEGLTDEKAGALIMAARNICWFGDEASGALVPRG
SVTSLYKKAGSAAAPFTMIMSDLSSKEYIFFDSIDNKLKAKSKNIPGLASISEDIKT
LLLDASVSPDTKFILNNLKLNIESSIGDYIYYEKLEPVKNIIHNSIDDLIDEFNLLEN
VSDELYELKKLNNLDEKYLISFEDISKNNSTYSVRFINKSNGESVYVETEKEIFSKY
SEHITKEISTIKNSIITDVNGNLLDNIQLDHTSQVNTLNAAFFIQSLIDYSSNKDVLN
DLSTSVKVQLYAQLFSTGLNTIYDSIQLVNLISNAVNDTINVLPTITEGIPIVSTILD
GINLGAAIKELLDEHDPLLKKELEAKVGVLAINMSLSIAATVASIVGIGAEVTIFLL
PIAGISAGIPSLVNNELILHDKATSVVNYFNHLSESKKYGPLKTEDDKILVPIDDLV
ISEIDFNNNSIKLGTCNILAMEGGSGHTVTGNIDHFFSSPSISSHIPSLSIYSAIGIETE
NLDFSKKIMMLPNAPSRVFWWETGAVPGLRSLENDGTRLLDSIRDLYPGKFYWR
FYAFFDYAITTLKPVYEDTNIKIKLDKDTRNFIMPTITTNEIRNKLSYSFDGAGGTY
SLLLSSYPISTNINLSKDDLWIFNIDNEVREISIENGTIKKGKLIKDVLSKIDINKNKL
IIGNQTIDFSGDIDNKDRYIFLTCELDDKISLIIEINLVAKSYSLLLSGDKNYLISNLS
NIIEKINTLGLDSKNIAYNYTDESNNKYFGAISKTSQKSIIHYKKDSKNILEFYNDS
TLEFNSKDFIAEDINVFMKDDINTITGKYYVDNNTDKSIDFSISLVSKNQVKVNGL
YLNESVYSSYLDFVKNSDGHHNTSNFMNLFLDNISFWKLFGFENINFVIDKYFTL
VGKTNLGYVEFICDNNKNIDIYFGEWKTSSSKSTIFSGNGRNVVVEPIYNPDTGED
ISTSLDFSYEPLYGIDRYINKVLIAPDLYTSLININTNYYSNEYYPEIIVLNPNTFHK
KVNINLDSSSFEYKWSTEGSDFILVRYLEESNKKILQKIRIKGILSNTQSFNKMSIDF
KDIKKLSLGYIMSNFKSFNSENELDRDHLGFKIIDNKTYYYDEDSKLVKGLININN
SLFYFDPIEFNLVTGWQTINGKKYYFDINTGAALISYKIINGKHFYFNNDGVMQL
GVFKGPDGFEYFAPANTQNNNIEGQAIVYQSKFLTLNGKKYYFDNDSKAVTGW
RIINNEKYYFNPNNAIAAVGLQVIDNNKYYFNPDTAIISKGWQTVNGSRYYFDTD
TAIAFNGYKTIDGKHFYFDSDCVVKIGVFSTSNGFEYFAPANTYNNNIEGQAIVY
QSKFLTLNGKKYYFDNNSKAVTGWQTIDSKKYYFNTNTAEAATGWQTIDGKKY
YFNTNTAEAATGWQTIDGKKYYFNTNTAIASTGYTIINGKHFYFNTDGIMQIGVF
KGPNGFEYFAPANTDANNIEGQAILYQNEFLTLNGKKYYFGSDSKAVTGWRIINN
KKYYFNPNNAIAAIHLCTINNDKYYFSYDGILQNGYITIERNNFYFDANNESKMV
TGVFKGPNGFEYFAPANTHNNNIEGQAIVYQNKFLTLNGKKYYFDNDSKAVTG
WQTIDGKKYYFNLNTAEAATGWQTIDGKKYYFNLNTAEAATGWQTIDGKKYYF
NTNTFIASTGYTSINGKHFYFNTDGIMQIGVFKGPNGFEYFAPANTHNNNIEGQAI
LYQNKFLTLNGKKYYFGSDSKAVTGLRTIDGKKYYFNTNTAVAVTGWQTINGK
KYYFNTNTSIASTGYTIISGKHFYFNTDGIMQIGVFKGPDGFEYFAPANTDANNIE
GQAIRYQNRFLYLHDNIYYFGNNSKAATGWVTIDGNRYYFEPNTAMGANGYKTI
DNKNFYFRNGLPQIGVFKGSNGFEYFAPANTDANNIEGQAIRYQNRFLHLLGKIY
YFGNNSKAVTGWQTINGKVYYFMPDTAMAAAGGLFEIDGVIYFFGVDGVKAPG
IYG.

SEQ ID NO: 29 - Toxin A-derived recombinant antigen - His-[helical spacer]-NusA-[thrombin site]-TxA4
HHHHHHHHHHGGSLAEAAAKEAAAKEAAAKEAAAKEAAAKAAAGGSHMASN
KEILAVVEAVSNEKALPREKIFEALESALATATKKKYEQEIDVRVQIDRKSGDFDT
FRRWLVVDEVTQPTKEITLEAARYEDESLNLGDYVEDQIESVTFDRITTQTAKQVI
VQKVREAERAMVVDQFREHEGEIITGVVKKVNRDNISLDLGNNAEAVILREDML
PRENFRPGDRVRGVLYSVRPEARGAQLFVTRSKPEMLIELFRIEVPEIGEEVIEIKA
AARDPGSRAKIAVKTNDKRIDPVGACVGMRGARVQAVSTELGGERIDIVLWDD
NPAQFVINAMAPADVASIVVDEDKHTMDIAVEAGNLAQAIGRNGQNVRLASQLS
GWELNVMTVDDLQAKHQAEAHAAIDTFTKYLDIDEDFATVLVEEGFSTLEELAY
VPMKELLEIEGLDEPTVEALRERAKNALATIAQAQEESLGDNKPADDLLNLEGV
DRDLAFKLAARGVCTLEDLAEQGIDDLADIEGLTDEKAGALIMAARNICWFGDE
ASGALVPRGSVTSLYKKAGSAAAPFTMIMSDLSSKEYIFFDSIDNKLKAKSKNIPG
LASISEDIKTLLLDASVSPDTKFILNNLKLNIESSIGDYIYYEKLEPVKNIIHNSIDDL
IDEFNLLENVSDELYELKKLNNLDEKYLISFEDISKNNSTYSVRFINKSNGESVYV
ETEKEIFSKYSEHITKEISTIKNSIITDVNGNLLDNIQLDHTSQVNTLNAAFFIQSLID
YSSNKDVLNDLSTSVKVQLYAQLFSTGLNTIYDSIQLVNLISNAVNDTINVLPTITE
GIPIVSTILDGINLGAAIKELLDEHDPLLKKELEAKVGVLAINMSLSIAATVASIVGI
GAEVTIFLLPIAGISAGIPSLVNNELILHDKATSVVNYFNHLSESKKYGPLKTEDDK
ILVPIDDLVISEIDFNNNSIKLGTCNILAMEGGSGHTVTGNIDHFFSSPSISSHIPSLSI
YSAIGIETENLDFSKKIMMLPNAPSRVFWWETGAVPGLRSLENDGTRLLDSIRDL
YPGKFYWRFYAFFDYAITTLKPVYEDTNIKIKLDKDTRNFIMPTITTNEIRNKLSYS
FDGAGGTYSLLLSSYPISTNINLSKDDLWIFNIDNEVREISIENGTIKKGKLIKDVLS
KIDINKNKLIIGNQTIDFSGDIDNKDRYIFLTCELDDKISLIIEINLVAKSYSLLLSGD
KNYLISNLSNIIEKINTLGLDSKNIAYNYTDESNNKYFGAISKTSQKSIIHYKKDSK
NILEFYNDSTLEFNSKDFIAEDINVFMKDDINTITGKYYVDNNTDKSIDFSISLVSK
NQVKVNGLYLNESVYSSYLDFVKNSDGHHNTSNFMNLFLDNISFWKLFGFENIN -continued SEQ ID NOs FVIDKYFTLVGKTNLGYVEFICDNNKNIDIYFGEWKTSSSKSTIFSGNGRNVVVEP
IYNPDTGEDISTSLDFSYEPLYGIDRYINKVLIAPDLYTSLININTNYYSNEYYPEIIV
LNPNTFHKKVNINLDSSSFEYKWSTEGSDFILVRYLEESNKKILQKIRIKGILSNTQ
SFNKMSIDFKDIKKLSLGYIMSNFKSFNSENELDRDHLGFKIIDNKTYYYDEDSKL
VKGLININNSLFYFDPIEFNLVTGWQTINGKKYYFDINTGAALISYKIINGKHFYFN
NDGVMQLGVFKGPDGFENFAPANTQNNNIEGQAIVYQSKFLTLNGKKYYFDND
SKAVTGWRIINNEKYYFNPNNAIAAVGLQVIDNNKYYFNPDTAIISKGWQTVNGS
RYYIDTDTAIAFNGYKTIDGKHFYFDSDCVVKIGVFSTSNGFEYFAPANTYNNNI
EGQAIVYQSKFLTLNGKKYYFDNNSKAVTGWQTIDSKKYYFNTNTAEAATGWQ
TIDGKKYYFNTNTAEAATGWQTIDGKKYYFNTNTAIASTGYTIINGKHFYFNTDG
IMQIGVFKGPNGFEYFAPANTDANNIEGQAILYQNEFLTLNGKKYYFGSDSKAVT
GWRIINNKKYYFNPNNAIAAIHLCTINNDKYYFSYDGILQNGYITIERNNFYFDAN
NESKMVTGVFKGPNGFEYFAPANTHNNNIEGQAIVYQNKFLTLNGKKYYFDNDS
KAVTGWQTIDGKKYYFNLNTAEAATGWQTIDGKKYYFNLNTAEAATGWQTID
GKKYYFNTNTFIASTGYTSINGKHFYFNTDGIMQIGVFKGPNGFEYFAPANTHNN
NIEGQAILYQNKFLTLNGKKYYFGSDSKAVTGLRTIDGKKYYFNTNTAVAVTGW
QTINGKKYYFNTNTSIASTGYTIISGKHFYFNTDGIMQIGVFKGPDGFEYFAPANT
DANNIEGQAIRYQNRFLYLHDNIYYFGNNSKAATGWVTIDGNRYYFEPNTAMGA
NGYKTIDNKNFYFRNGLPQIGVFKGSNGFEYFAPANTDANNIEGQAIRYQNRFLH
LLGKIYYFGNNSKAVTGWQTINGKVYYFMPDTAMAAAGGLFEIDGVIYFFGVDG
VKAPGIYG SEQ ID NO: 30 - Toxin A-derived recombinant antigen - His-NusA-[linear spacer]-[thrombin site]-TxA4
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALGGSGGSGGSGGSGGSGGSGGSGGSGGSLVPRGSGS
AAAPFTMIMSDLSSKEYIFFDSIDNKLKAKSKNIPGLASISEDIKTLLLDASVSPDT
KFILNNLKLNIESSIGDYIYYEKLEPVKNIIHNSIDDLIDEFNLLENVSDELYELKKL
NNLDEKYLISFEDISKNNSTYSVRFINKSNGESVYVETEKEIFSKYSEHITKEISTIK
NSIITDVNGNLLDNIQLDHTSQVNTLNAAFFIQSLIDYSSNKDVLNDLSTSVKVQL
YAQLFSTGLNTIYDSIQLVNLISNAVNDTINVLPTITEGIPIVSTILDGINLGAAIKEL
LDEHDPLLKKELEAKVGVLAINMSLSIAATVASIVGIGAEVTIFLLPIAGISAGIPSL
VNNELILHDKATSVVNYFNHLSESKKYGPLKTEDDKILVPIDDLVISEIDFNNNSIK
LGTCNILAMEGGSGHTVTGNIDHFFSSPSISSHIPSLSIYSAIGIETENLDFSKKIMM
LPNAPSRVFWWETGAVPGLRSLENDGTRLLDSIRDLYPGKFYWRFYAFFDYAITT
LKPVYEDTNIKIKLDKDTRNFIMPTITTNEIRNKLSYSFDGAGGTYSLLLSSYPIST
NINLSKDDLWIFNIDNEVREISIENGTIKKGKLIKDVLSKIDINKNKLIIGNQTIDFSG
DIDNKDRYIFLTCELDDKISLIIEINLVAKSYSLLLSGDKNYLISNLSNIIEKINTLGL
DSKNIAYNYTDESNNKYFGAISKTSQKSIIHYKKDSKNILEFYNDSTLEFNSKDFIA
EDINVFMKDDINTITGKYYVDNNTDKSIDFSISLVSKNQVKVNGLYLNESVYSSY
LDFVKNSDGHHNTSNFMNLFLDNISFWKLFGFENINFVIDKYFTLVGKTNLGYVE
FICDNNKNIDIYFGEWKTSSSKSTIFSGNGRNVVVEPIYNPDTGEDISTSLDFSYEPL
YGIDRYINKVLIAPDLYTSLININTNYYSNEYYPEIIVLNPNTFHKKVNINLDSSSFE
YKWSTEGSDFILVRYLEESNKKILQKIRIKGILSNTQSFNKMSIDFKDIKKLSLGYI
MSNFKSFNSENELDRDHLGFKIIDNKTYYYDEDSKLVKGLININNSLFYFDPIEFN
LVTGWQTINGKKYYFDINTGAALISYKIINGKHFYFNNDGVMQLGVFKGPDGFE
YFAPANTQNNNIEGQAIVYQSKFLTLNGKKYYFDNDSKAVTGWRIINNEKYYFN
PNNAIAAVGLQVIDNNKYYFNPDTAIISKGWQTVNGSRYYFDTDTAIAFNGYKTI
DGKHFYFDSDCVVKIGVFSTSNGFEYFAPANTYNNNIEGQAIVYQSKFLTLNGKK
YYFDNNSKAVTGWQTIDSKKYYFNTNTAEAATGWQTIDGKKYYFNTNTAEAAT
GWQTIDGKKYYFNTNTAIASTGYTIINGKHFYFNTDGIMQIGVFKGPNGFEYFAP
ANTDANNIEGQAILYQNEFLTLNGKKYYFGSDSKAVTGWRIINNKKYYFNPNNAI
AAIHLCTINNDKYYFSYDGILQNGYITIERNNFYFDANNESKMVTGVFKGPNGFE
YFAPANTHNNNIEGQAIVYQNKFLTLNGKKYYFDNDSKAVTGWQTIDGKKYYF
NLNTAEAATGWQTIDGKKYYFNLNTAEAATGWQTIDGKKYYFNTNTFIASTGYT
SINGKHFYFNTDGIMQIGVFKGPNGFEYFAPANTHNNNIEGQAILYQNKFLTLNG
KKYYFGSDSKAVTGLRTIDGKKYYFNTNTAVAVTGWQTINGKKYYFNTNTSIAS
TGYTIISGKHFYFNTDGIMQIGVFKGPDGFEYFAPANTDANNIEGQAIRYQNRFLY
LHDNIYYFGNNSKAATGWVTIDGNRYYFEPNTAMGANGYKTIDNKNFYFRNGL
PQIGVFKGSNGFEYFAPANTDANNIEGQAIRYQNRFLHLLGKIYYFGNNSKAVTG
WQTINGKVYYFMPDTAMAAAGGLFEIDGVIYFFGVDGVKAPGIYG SEQ ID NO: 31 - Toxin A-derived recombinant antigen - His-NusA-[helical spacer]-[thrombin site]-TxA4
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST -continued SEQ ID NOs ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALLAEAAAKEAAAKEAAAKEAAAKEAAAKAAAGGS
LVPRGSGSAAAPFTMIMSDLSSKEYIFFDSIDNKLKAKSKNIPGLASISEDIKTLLL
DASVSPDTKFILNNLKLNIESSIGDYIYYEKLEPVKNIIHNSIDDLIDEFNLLENVSD
ELYELKKLNNLDEKYLISFEDISKNNSTYSVRFINKSNGESVYVETEKEIFSKYSEH
ITKEISTIKNSIITDVNGNLLDNIQLDHTSQVNTLNAAFFIQSLIDYSSNKDVLNDLS
TSVKVQLYAQLFSTGLNTIYDSIQLVNLISNAVNDTINVLPTITEGIPIVSTILDGINL
GAAIKELLDEHDPLLKKELEAKVGVLAINMSLSIAATVASIVGIGAEVTIFLLPIAG
ISAGIPSLVNNELILHDKATSVVNYFNHLSESKKYGPLKTEDDKILVPIDDLVISEID
FNNNSIKLGTCNILAMEGGSGHTVTGNIDHFFSSPSISSHIPSLSIYSAIGIETENLDF
SKKIMMLPNAPSRVFWWETGAVPGLRSLENDGTRLLDSIRDLYPGKFYWRFYAF
FDYAITTLKPVYEDTNIKIKLDKDTRNFIMPTITTNEIRNKLSYSFDGAGGTYSLLL
SSYPISTNINLSKDDLWIFNIDNEVREISIENGTIKKGKLIKDVLSKIDINKNKLIIGN
QTIDFSGDIDNKDRYIFLTCELDDKISLIIEINLVAKSYSLLLSGDKNYLISNLSNIIE
KINTLGLDSKNIAYNYTDESNNKYFGAISKTSQKSIIHYKKDSKNILEFYNDSTLEF
NSKDFIAEDINVFMKDDINTITGKYYVDNNTDKSIDFSISLVSKNQVKVNGLYLNE
SVYSSYLDFVKNSDGHHNTSNFMNLFLDNISFWKLFGFENINFVIDKYFTLVGKT
NLGYVEFICDNNKNIDIYFGEWKTSSSKSTIFSGNGRNVVVEPIYNPDTGEDISTSL
DFSYEPLYGIDRYINKVLIAPDLYTSLININTNYYSNEYYPEIIVLNPNTFHKKVNIN
LDSSSPENKWSTEGSDFILVRYLEESNKKILQKIRIKGILSNTQSFNKMSIDFKDIKK
LSLGYIMSNFKSFNSENELDRDHLGFKIIDNKTYYYDEDSKLVKGLININNSLFYF
DPIEFNLVTGWQTINGKKYYFDINTGAALISYKIINGKHFYFNNDGVMQLGVFKG
PDGFEYFAPANTQNNNIEGQAIVYQSKFLTLNGKKYYFDNDSKAVTGWRIINNE
KYYFNPNNAIAAVGLQVIDNNKYYFNPDTAIISKGWQTVNGSRYYFDTDTAIAFN
GYKTIDGKHFYFDSDCVVKIGVFSTSNGFEYFAPANTYNNNIEGQAIVYQSKFLT
LNGKKYYPDNNSKAVTGWQTIDSKKYYFNTNTAEAATGWQTIDGKKYYFNTNT
AEAATGWQTIDGKKYYFNTNTAIASTGYTIINGKHFYFNTDGIMQIGVFKGPNGF
EYFAPANTDANNIEGQAILYQNEFLTLNGKKYYFGSDSKAVTGWRIINNKKYYF
NPNNAIAAIHLCTINNDKYYFSYDGILQNGYITIERNNFYFDANNESKMVTGVFK
GPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFI
ASTGYTSINGKHFYFNTDGIMQIGVFKGPNGFEYFAPANTHNNNIEGQAILYQNK
FLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRY
QNRFLYLHDNIYYFGNNSKAATGWVTIDGNRYYFEPNTAMGANGYKTIDNKNF
YFRNGLPQIGVFKGSNGFEYFAPANTDANNIEGQAIRYQNRFLHLLGKIYYFGNN
SKAVTGWQTINGKVYYFMPDTAMAAAGGLFEIDGVIYFFGVDGVKAPGIYG SEQ ID NO: 32 - Toxin A-derived recombinant antigen - His-[linear spacer]-NusA-[thrombin site]-TxA3
HHHHHHHHHGGSGGSGGSGGSGGSGGSGGSGGSGGSGGSHMASNKEILAVVEA
VSNEKALPREKIFEALESALATATKKKYEQEIDVRVQIDRKSGDFDTPRRWLVVD
EVTQPTKEITLEAARYEDESLNLGDYVEDQIESVTFDRITTQTAKQVIVQKVREAE
RAMVVDQFREHEGEIITGVVKKVNRDNISLDLGNNAEAVILREDMLPRENFRPG
DRVRGVLYSVRPEARGAQLFVTRSKPEMLIELFRIEVPEIGEEVIEIKAAARDPGSR
AKIAVKTNDKRIDPVGACVGMRGARVQAVSTELGGERIDIVLWDDNPAQFVINA
MAPADVASIVVDEDKHTMDIAVEAGNLAQAIGRNGQNVRLASQLSGWELNVMT
VDDLQAKHQAEAHAAIDTFTKYLDIDEDFATVLVEEGFSTLEELAYVPMKELLEI
EGLDEPTVEALRERAKNALATIAQAQEESLGDNKPADDLLNLEGVDRDLAFKLA
ARGVCTLEDLAEQGIDDLADIEGLTDEKAGALIMAARNICWFGDEASGALVPRG
SVTSLYKKAGSAAAPFTMESKKYGPLKTEDDKILVPIDDLVISEIDFNNNSIKLGT
CNILAMEGGSGHTVTGNIDHFFSSPSISSHIPSLSIYSAIGIETENLDFSKKIMMLPN
APSRVFWWETGAVPGLRSLENDGTRLLDSIRDLYPGKFYWRFYAFFDYAITTLKP
VYEDTNIKIKLDKDTRNFIMPTITTNEIRNKLSYSFDGAGGTYSLLLSSYPISTNINL
SKDDLWIFNIDNEVREISIENGTIKKGKLIKDVLSKIDINKNKLIIGNQTIDFSGDID
NKDRYIFLTCELDDKISLIIEINLVAKSYSLLLSGDKNYLISNLSNIIEKINTLGLDSK
NIAYNYTDESNNKYFGAISKTSQKSIIHYKKDSKNILEFYNDSTLEFNSKDFIAEDI
NVFMKDDINTITGKYYVDNNTDKSIDFSISLVSKNQVKVNGLYLNESVYSSYLDF
VKNSDGHHNTSNFMNLFLDNISFWKLFGFENINFVIDKYFTLVGKTNLGYVEFIC
DNNKNIDIYFGEWKTSSSKSTIFSGNGRNVVVEPIYNPDTGEDISTSLDFSYEPLYG
IDRYINKVLIAPDLYTSLININTNYYSNEYYPEIIVLNPNTFHKKVNINLDSSSFEYK
WSTEGSDFILVRYLEESNKKILQKIRIKGILSNTQSFNKMSIDFKDIKKLSLGYIMS
NFKSFNSENELDRDHLGFKIIDNKTYYYDEDSKLVKGLININNSLFYFDPIEFNLVT
GWQTINGKKYYFDINTGAALISYKIINGKHFYFNNDGVMQLGVFKGPDGFEYFA
PANTQNNNIEGQAIVYQSKFLTLNGKKYYFDNDSKAVTGWRIINNEKYYFNPNN
AIAAVGLQVIDNNKYYFNPDTAIISKGWQTVNGSRYYFDTDTAIAFNGYKTIDGK
HFYFDSDCVVKIGVFSTSNGFEYFAPANTYNNNIEGQAIVYQSKFLTLNGKKYYF
DNNSKAVTGWQTIDSKKYYFNTNTAEAATGWQTIDGKKYYFNTNTAEAATGW
QTIDGKKYYFNTNTAIASTGYTIINGKHFYFNTDGIMQIGVFKGPNGFENFAPANT
DANNIEGQAILYQNEFLTLNGKKYYFGSDSKAVTGWRIINNKKYYFNPNNAIAAI
HLCTINNDKYYFSYDGILQNGYITIERNNFYFDANNESKMVTGVFKGPNGFEYFA
PANTHNNNIEGQAIVYQNKFLTLNGKKYYFDNDSKAVTGWQTIDGKKYYFNLN
TAEAATGWQTIDGKKYYFNLNTAEAATGWQTIDGKKYYFNTNTFIASTGYTSIN
GKHFYFNTDGIMQIGVFKGPNGFENFAPANTHNNNIEGQAILYQNKFLTLNGKK -continued SEQ ID NOs YYFGSDSKAVTGLRTIDGKKYYFNTNTAVAVTGWQTINGKKYYFNTNTSIASTG
YTIISGKHFYFNTDGIMQIGVFKGPDGFEYFAPANTDANNIEGQAIRYQNRFLYLH
DNIYYFGNNSKAATGWVTIDGNRYYFEPNTAMGANGYKTIDNKNFYFRNGLPQI
GVFKGSNGFEYFAPANTDANNIEGQAIRYQNRFLHLLGKIYYFGNNSKAVTGWQ
TINGKVYYFMPDTAMAAAGGLFEIDGVIYFFGVDGVKAPGIYG SEQ ID NO: 33 - Toxin A-derived recombinant antigen - His-[helical spacer]-NusA-[thrombin site]-TxA3
HHHHHHHHHHGGSLAEAAAKEAAAKEAAAKEAAAKEAAAKAAAGGSHMASN
KEILAVVEAVSNEKALPREKIFEALESALATATKKKYEQEIDVRVQIDRKSGDFDT
FRRWLVVDEVTQPTKEITLEAARYEDESLNLGDYVEDQIESVTFDRITTQTAKQVI
VQKVREAERAMVVDQFREHEGEIITGVVKKVNRDNISLDLGNNAEAVILREDML
PRENFRPGDRVRGVLYSVRPEARGAQLFVTRSKPEMLIELFRIEVPEIGEEVIEIKA
AARDPGSRAKIAVKTNDKRIDPVGACVGMRGARVQAVSTELGGERIDIVLWDD
NPAQFVINAMAPADVASIVVDEDKHTMDIAVEAGNLAQAIGRNGQNVRLASQLS
GWELNVMTVDDLQAKHQAEAHAAIDTFTKYLDIDEDFATVLVEEGFSTLEELAY
VPMKELLEIEGLDEPTVEALRERAKNALATIAQAQEESLGDNKPADDLLNLEGV
DRDLAFKLAARGVCTLEDLAEQGIDDLADIEGLTDEKAGALIMAARNICWFGDE
ASGALVPRGSVTSLYKKAGSAAAPFTMESKKYGPLKTEDDKILVPIDDLVISEIDF
NNNSIKLGTCNILAMEGGSGHTVTGNIDHFFSSPSISSHIPSLSIYSAIGIETENLDFS
KKIMMLPNAPSRVFWWETGAVPGLRSLENDGTRLLDSIRDLYPGKFYWRFYAFF
DYAITTLKPVYEDTNIKIKLDKDTRNFIMPTITTNEIRNKLSYSFDGAGGTYSLLLS
SYPISTNINLSKDDLWIFNIDNEVREISIENGTIKKGKLIKDVLSKIDINKNKLIIGNQ
TIDFSGDIDNKDRYIFLTCELDDKISLIIEINLVAKSYSLLLSGDKNYLISNLSNIIEKI
NTLGLDSKNIAYNYTDESNNKYFGAISKTSQKSIIHYKKDSKNILEFYNDSTLEFN
SKDFIAEDINVFMKDDINTITGKYYVDNNTDKSIDFSISLVSKNQVKVNGLYLNES
VYSSYLDFVKNSDGHHNTSNFMNLFLDNISFWKLFGFENINFVIDKYFTLVGKTN
LGYVEFICDNNKNIDIYFGEWKTSSSKSTIFSGNGRNVVVEPIYNPDTGEDISTSLD
FSYEPLYGIDRYINKVLIAPDLYTSLININTNYYSNEYYPEIIVLNPNTFHKKVNINL
DSSSFEYKWSTEGSDFILVRYLEESNKKILQKIRIKGILSNTQSFNKMSIDFKDIKKL
SLGYIMSNFKSFNSENELDRDHLGFKIIDNKTYYYDEDSKLVKGLININNSLFYI-D
PIEFNLVTGWQTINGKKYYFDINTGAALISYKIINGKHFYFNNDGVMQLGVFKGP
DGFEYFAPANTQNNNIEGQAIVYQSKFLTLNGKKYYFDNDSKAVTGWRIINNEK
YYFNPNNAIAAVGLQVIDNNKYYFNPDTAIISKGWQTVNGSRYYFDTDTAIAFNG
YKTIDGKHFYFDSDCVVKIGVFSTSNGFEYFAPANTYNNNIEGQAIVYQSKFLTL
NGKKYYFDNNSKAVTGWQTIDSKKYYFNTNTAEAATGWQTIDGKKYYFNTNT
AEAATGWQTIDGKKYYFNTNTAIASTGYTIINGKHFYFNTDGIMQIGVFKGPNGF
EYFAPANTDANNIEGQAILYQNEFLTLNGKKYYFGSDSKAVTGWRIINNKKYYF
NPNNAIAAIHLCTINNDKYYFSYDGILQNGYITIERNNFYFDANNESKMVTGVFK
GPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFI
ASTGYTSINGKHFYFNTDGIMQIGVFKGPNGFEYFAPANTHNNNIEGQAILYQNK
FLTLNGKKYYFGSDSKAVTGLRTIDGKKYYFNTNTAVAVTGWQTINGKKYYFN
TNTSIASTGYTIISGKHFYFNTDGIMQIGVFKGPDGFEYFAPANTDANNIEGQAIRY
QNRFLYLHDNIYYFGNNSKAATGWVTIDGNRYYFEPNTAMGANGYKTIDNKNF
YFRNGLPQIGVFKGSNGFEYFAPANTDANNIEGQAIRYQNRFLHLLGKIYYFGNN
SKAVTGWQTINGKVYYFMPDTAMAAAGGLFEIDGVIYFFGVDGVKAPGIYG SEQ ID NO: 34 - Toxin A-derived recombinant antigen - His-NusA-[linear spacer]-[thrombin site]-TxA3
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALGGSGGSGGSGGSGGSGGSGGSGGSGGSLVPRGSGS
AAAPFTMESKKYGPLKTEDDKILVPIDDLVISEIDFNNNSIKLGTCNILAMEGGSG
HTVTGNIDHFFSSPSISSHIPSLSIYSAIGIETENLDFSKKIMMLPNAPSRVFWWETG
AVPGLRSLENDGTRLLDSIRDLYPGKFYWRFYAFFDYAITTLKPVYEDTNIKIKLD
KDTRNFIMPTITTNEIRNKLSYSFDGAGGTYSLLLSSYPISTNINLSKDDLWIFNIDN
EVREISIENGTIKKGKLIKDVLSKIDINKNKLIIGNQTIDFSGDIDNKDRYIFLTCELD
DKISLIIEINLVAKSYSLLLSGDKNYLISNLSNIIEKINTLGLDSKNIAYNYTDESNN
KYFGAISKTSQKSIIHYKKDSKNILEFYNDSTLEFNSKDFIAEDINVFMKDDINTIT
GKYYVDNNTDKSIDFSISLVSKNQVKVNGLYLNESVYSSYLDFVKNSDGHHNTS
NFMNLFLDNISFWKLFGFENINFVIDKYFTLVGKTNLGYVEFICDNNKNIDIYFGE
WKTSSSKSTIFSGNGRNVVVEPIYNPDTGEDISTSLDFSYEPLYGIDRYINKVLIAP
DLYTSLININTNYYSNEYYPEIIVLNPNTFHKKVNINLDSSSFEYKWSTEGSDFILV
RYLEESNKKILQKIRIKGILSNTQSFNKMSIDFKDIKKLSLGYIMSNFKSFNSENEL
DRDHLGFKIIDNKTYYYDEDSKLVKGLININNSLFYFDPIEFNLVTGWQTINGKKY
YFDINTGAALISYKIINGKHFYFNNDGVMQLGVFKGPDGFEYFAPANTQNNNIEG
QAIVYQSKFLTLNGKKYYFDNDSKAVTGWRIINNEKYYFNPNNAIAAVGLQVID
NNKYYFNPDTAIISKGWQTVNGSRYYFDTDTAIAFNGYKTIDGKHFYFDSDCVV
KIGVFSTSNGFEYFAPANTYNNNIEGQAIVYQSKFLTLNGKKYYFDNNSKAVTG -continued

| SEQ ID NOs |
|---|

WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG

SEQ ID NO: 35 - Toxin A-derived recombinant antigen - His-NusA-[helical spacer]-[thrombin site]-TxA3
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALLAEAAAKEAAAKEAAAKEAAAKEAAAKAAAGGS
LVPRGSGSAAAPFTMESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYSI4DGAGGTYSLLLSSYPISTNINLSKD
DLWIFNIDNEVREISIENGTIKKGKLIKDVLSKIDINKNKLIIGNQTIDFSGDIDNKD
RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
KNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLVTGW
QTINGKKYYFDINTGAALISYKIINGKHFYFNNDGVMQLGVFKGPDGFEYFAPAN
TQNNNIEGQAIVYQSKFLTLNGKKYYFDNDSKAVTGWRIINNEKYYFNPNNAIA
AVGLQVIDNNKYYFNPDTAIISKGWQTVNGSRYYFDTDTAIAFNGYKTIDGKHF
YFDSDCVVKIGVFSTSNGFEYFAPANTYNNNIEGQAIVYQSKFLTLNGKKYYFDN
NSKAVTGWQTIDSKKYYFNTNTAEAATGWQTIDGKKYYFNTNTAEAATGWQTI
DGKKYYFNTNTAIASTGYTIINGKHFYFNTDGIMQIGVFKGPNGFEYFAPANTDA
NNIEGQAILYQNEFLTLNGKKYYFGSDSKAVTGWRIINNKKYYFNPNNAIAAIHL
CTINNDKYYFSYDGILQNGYITIERNNFYFDANNESKMVTGVFKGPNGFEYFAPA
NTHNNNIEGQAIVYQNKFLTLNGKKYYFDNDSKAVTGWQTIDGKKYYFNLNTA
EAATGWQTIDGKKYYFNLNTAEAATGWQTIDGKKYYFNTNTFIASTGYTSINGK
HFYFNTDGIMQIGVFKGPNGFEYFAPANTHNNNIEGQAILYQNKFLTLNGKKYYF
GSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNI
YYFGNNSKAATGWVTIDGNRYYFEPNTAMGANGYKTIDNKNFYFRNGLPQIGV
FKGSNGFEYFAPANTDANNIEGQAIRYQNRFLHLLGKIYYFGNNSKAVTGWQTIN
GKVYYFMPDTAMAAAGGLFEIDGVIYFFGVDGVKAPGIYG SEQ ID NO: 36 - Toxin A-derived recombinant antigen - His-[linear spacer]-Thioredoxin-[thrombin site]-TxA4
HHHHHHHHHHGGSGGSGGSGGSGGSGGSGGSGGSGGSGGSHMASDKIIHLTDDSF
DTDVLKADGAILVDFWAEWCGPCKMIAPILDEIADEYQGKLTVAKLNIDQNPGT
APKYGIRGIPTLLLFKNGEVAATKVGALSKGQLKEFLDANLARALVPRGSVTSLY
KKAGSAAAPFTMIMSDLSSKEYIFFDSIDNKLKAKSKNIPGLASISEDIKTLLLDAS
VSPDTKFILNNLKLNIESSIGDYIYYEKLEPVKNIIHNSIDDLIDEFNLLENVSDELY
ELKKLNNLDEKYLISFEDISKNNSTYSVRFINKSNGESVYVETEKEIFSKYSEHITK
EISTIKNSIITDVNGNLLDNIQLDHTSQVNTLNAAFFIQSLIDYSSNKDVLNDLSTSV
KVQLYAQLFSTGLNTIYDSIQLVNLISNAVNDTINVLPTITEGIPIVSTILDGINLGA
AIKELLDEHDPLLKKELEAKVGVLAINMSLSIAATVASIVGIGAEVTIFLLPIAGISA
GIPSLVNNELILHDKATSVVNYFNHLSESKKYGPLKTEDDKILVPIDDLVISEIDFN
NNSIKLGTCNILAMEGGSGHTVTGNIDHFFSSPSISSHIPSLSIYSAIGIETENLDFSK
KIMMLPNAPSRVFWWETGAVPGLRSLENDGTRLLDSIRDLYPGKFYWRFYAFFD
YAITTLKPVYEDTNIKIKLDKDTRNFIMPTITTNEIRNKLSYSFDGAGGTYSLLLSS
YPISTNINLSKDDLWIFNIDNEVREISIENGTIKKGKLIKDVLSKIDINKNKLIIGNQT
IDFSGDIDNKDRYIFLTCELDDKISLIIEINLVAKSYSLLLSGDKNYLISNLSNIIEKIN
TLGLDSKNIAYNYTDESNNKYFGAISKTSQKSIIHYKKDSKNILEFYNDSTLEFNS
KDFIAEDINVFMKDDINTITGKYYVDNNTDKSIDFSISLVSKNQVKVNGLYLNESV
YSSYLDFVKNSDGHHNTSNFMNLFLDNISFWKLFGFENINFVIDKYFTLVGKTNL
GYVEFICDNNKNIDIYFGEWKTSSSKSTIFSGNGRNVVVEPIYNPDTGEDISTSLDF
SYEPLYGIDRYINKVLIAPDLYTSLININTNYYSNEYYPEIIVLNPNTFHKKVNINLD -continued

| SEQ ID NOs |
|---|

SSSFEYKWSTEGSDFILVRYLEESNKKILQKIRIKGILSNTQSFNKMSIDFKDIKKLS
LGYIMSNFKSFNSENELDRDHLGFKIIDNKTYYYDEDSKLVKGLININNSLFYFDPI
EFNLVTGWQTINGKKYYFDINTGAALISYKIINGKHFYFNNDGVMQLGVFKGPD
GFEYFAPANTQNNNIEGQAIVYQSKFLTLNGKKYYFDNDSKAVTGWRIINNEKY
YFNPNNAIAAVGLQVIDNNKYYFNPDTAIISKGWQTVNGSRYYFDTDTAIAFNGY
KTIDGKHFYFDSDCVVKIGVFSTSNGFEYFAPANTYNNNIEGQAIVYQSKFLTLN
GKKYYFDNNSKAVTGWQTIDSKKYYFNTNTAEAATGWQTIDGKKYYFNTNTAE
AATGWQTIDGKKYYFNTNTAIASTGYTIINGKHFYFNTDGIMQIGVFKGPNGFEY
FAPANTDANNIEGQAILYQNEFLTLNGKKYYFGSDSKAVTGWRIINNKKYYFNP
NNAIAAIHLCTINNDKYYFSYDGILQNGYITIERNNFYFDANNESKMVTGVFKGP
NGFEYFAPANTHNNNIEGQAIVYQNKFLTLNGKKYYFDNDSKAVTGWQTIDGK
KYYFNLNTAEAATGWQTIDGKKYYFNLNTAEAATGWQTIDGKKYYFNTNTFIA
STGYTSINGKHFYFNTDGIMQIGVFKGPNGFEYFAPANTHNNNIEGQAILYQNKF
LTLNGKKYYFGSDSKAVTGLRTIDGKKYYFNTNTAVAVTGWQTINGKKYYFNT
NTSIASTGYTIISGKHFYFNTDGIMQIGVFKGPDGFENFAPANTDANNIEGQAIRY
QNRFLYLHDNIYYFGNNSKAATGWVTIDGNRYYFEPNTAMGANGYKTIDNKNF
YFRNGLPQIGVFKGSNGFEYFAPANTDANNIEGQAIRYQNRFLHLLGKIYYFGNN
SKAVTGWQTINGKVYYFMPDTAMAAAGGLFEIDGVIYFFGVDGVKAPGIYG

SEQ ID NO: 37 - Toxin A-derived recombinant antigen - His-[helical spacer]-Thioredoxin-[thrombin site]-TxA4
HHHHHHHHHHGGSLAEAAAKEAAAKEAAAKEAAAKEAAAKAAAGGSHMASD
KIIHLTDDSFDTDVLKADGAILVDFWAEWCGPCKMIAPILDEIADEYQGKLTVAK
LNIDQNPGTAPKYGIRGIPTLLLFKNGEVAATKVGALSKGQLKEFLDANLARALV
PRGSVTSLYKKAGSAAAPFTMIMSDLSSKEYIFFDSIDNKLKAKSKNIPGLASISED
IKTLLLDASVSPDTKFILNNLKLNIESSIGDYIYYEKLEPVKNIIHNSIDDLIDEFNLL
ENVSDELYELKKLNNLDEKYLISFEDISKNNSTYSVRFINKSNGESVYVETEKEIFS
KYSEHITKEISTIKNSIITDVNGNLLDNIQLDHTSQVNTLNAAFFIQSLIDYSSNKDV
LNDLSTSVKVQLYAQLFSTGLNTIYDSIQLVNLISNAVNDTINVLPTITEGIPIVSTI
LDGINLGAAIKELLDEHDPLLKKELEAKVGVLAINMSLSIAATVASIVGIGAEVTIF
LLPIAGISAGIPSLVNNELILHDKATSVVNYFNHLSESKKYGPLKTEDDKILVPIDD
LVISEIDFNNNSIKLGTCNILAMEGGSGHTVTGNIDHFFSSPSISSHIPSLSIYSAIGIE
TENLDFSKKIMMLPNAPSRVFWWETGAVPGLRSLENDGTRLLDSIRDLYPGKFY
WRFYAFFDYAITTLKPVYEDTNIKIKLDKDTRNFIMPTITTNEIRNKLSYSFDGAG
GTYSLLLSSYPISTNINLSKDDLWIFNIDNEVREISIENGTIKKGKLIKDVLSKIDINK
NKLIIGNQTIDFSGDIDNKDRYIFLTCELDDKISLIIEINLVAKSYSLLLSGDKNYLIS
NLSNIIEKINTLGLDSKNIAYNYTDESNNKYFGAISKTSQKSIIHYKKDSKNILEFY
NDSTLEFNSKDFIAEDINVFMKDDINTITGKYYVDNNTDKSIDFSISLVSKNQVKV
NGLYLNESVYSSYLDFVKNSDGHHNTSNFMNLFLDNISFWKLFGFENINFVIDKY
FTLVGKTNLGYVEFICDNNKNIDIYFGEWKTSSSKSTIFSGNGRNVVVEPIYNPDT
GEDISTSLDFSYEPLYGIDRYINKVLIAPDLYTSLININTNYYSNEYYPEIIVLNPNTF
HKKVNINLDSSSFEYKWSTEGSDFILVRYLEESNKKILQKIRIKGILSNTQSFNKMS
IDFKDIKKLSLGYIMSNFKSFNSENELDRDHLGFKIIDNKTYYYDEDSKLVKGLINI
NNSLFYFDPIEFNLVTGWQTINGKKYYFDINTGAALISYKIINGKHFYFNNDGVM
QLGVFKGPDGFEYFAPANTQNNNIEGQAIVYQSKFLTLNGKKYYFDNDSKAVTG
WRIINNEKYYFNPNNAIAAVGLQVIDNNKYYFNPDTAIISKGWQTVNGSRYYFDT
DTAIAFNGYKTIDGKHFYFDSDCVVKIGVFSTSNGFEYFAPANTYNNNIEGQAIV
YQSKFLTLNGKKYYFDNNSKAVTGWQTIDSKKYYFNTNTAEAATGWQTIDGKK
YYFNTNTAEAATGWQTIDGKKYYFNTNTAIASTGYTIINGKHFYFNTDGIMQIGV
FKGPNGFEYFAPANTDANNIEGQAILYQNEFLTLNGKKYYFGSDSKAVTGWRIIN
NKKYYFNPNNAIAAIHLCTINNDKYYFSYDGILQNGYITIERNNFYFDANNESKM
VTGVFKGPNGFEYFAPANTHNNNIEGQAIVYQNKFLTLNGKKYYFDNDSKAVTG
WQTIDGKKYYFNLNTAEAATGWQTIDGKKYYFNLNTAEAATGWQTIDGKKYYF
NTNTFIASTGYTSINGKHFYFNTDGIMQIGVFKGPNGFEYFAPANTHNNNIEGQAI
LYQNKFLTLNGKKYYFGSDSKAVTGLRTIDGKKYYFNTNTAVAVTGWQTINGK
KYYFNTNTSIASTGYTIISGKHFYFNTDGIMQIGVFKGPDGFEYFAPANTDANNIE
GQAIRYQNRFLYLHDNIYYFGNNSKAATGWVTIDGNRYYFEPNTAMGANGYKTI
DNKNFYFRNGLPQIGVFKGSNGFEYFAPANTDANNIEGQAIRYQNRFLHLLGKIY
YFGNNSKAVTGWQTINGKVYYFMPDTAMAAAGGLFEIDGVIYFFGVDGVKAPG
IYG SEQ ID NO: 38 - Toxin A-derived recombinant antigen - His-Thioredoxin-[linear spacer]-[thrombin site]-TxA4
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALGGSGGSGGSGGSGGSGGSGGSGGSGGSGGSLVPRGSGSAAAPFTM
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
LKKELEAKVGVLAINMSLSIAATVASIVGIGAEVTIFLLPIAGISAGIPSLVNNELIL
HDKATSVVNYFNHLSESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYS14DGAGGTYSLLLSSYPISTNINLSKD
DLWIFNIDNEVREISIENGTIKKGKLIKDVLSKIDINKNKLIIGNQTIDFSGDIDNKD -continued

| SEQ ID NOs |
| --- |

RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
KNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFENKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLVTGW
QTINGKKYYFDINTGAALISYKIINGKHFYFNNDGVMQLGVFKGPDGFEYFAPAN
TQNNNIEGQAIVYQSKFLTLNGKKYYFDNDSKAVTGWRIINNEKYYFNPNNAIA
AVGLQVIDNNKYYFNPDTAIISKGWQTVNGSRYYFDTDTAIAFNGYKTIDGKHF
YFDSDCVVKIGVFSTSNGFEYFAPANTYNNNIEGQAIVYQSKFLTLNGKKYYPDN
NSKAVTGWQTIDSKKYYFNTNTAEAATGWQTIDGKKYYFNTNTAEAATGWQTI
DGKKYYFNTNTAIASTGYTIINGKHFYFNTDGIMQIGVFKGPNGFEYFAPANTDA
NNIEGQAILYQNEFLTLNGKKYYFGSDSKAVTGWRIINNKKYYFNPNNAIAAIHL
CTINNDKYYFSYDGILQNGYITIERNNFYFDANNESKMVTGVFKGPNGFEYFAPA
NTHNNNIEGQAIVYQNKFLTLNGKKYYFDNDSKAVTGWQTIDGKKYYFNLNTA
EAATGWQTIDGKKYYFNLNTAEAATGWQTIDGKKYYFNTNTFIASTGYTSINGK
HFYFNTDGIMQIGVFKGPNGFEYFAPANTHNNNIEGQAILYQNKFLTLNGKKYYF
GSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNI
YYFGNNSKAATGWVTIDGNRYYFEPNTAMGANGYKTIDNKNFYFRNGLPQIGV
FKGSNGFEYFAPANTDANNIEGQAIRYQNRFLHLLGKIYYFGNNSKAVTGWQTIN
GKVYYFMPDTAMAAAGGLFEIDGVIYFFGVDGVKAPGIYG

SEQ ID NO: 39 - Toxin A-derived recombinant antigen - His-Thioredoxin-[helical spacer]-[thrombin site]-TxA4
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAAPFTMIMSDLSSKEYIFFDSIDNKLKAKSKNIPGLASISEDIKTLLLDASVSPDT
KFILNNLKLNIESSIGDYIYYEKLEPVKNIIHNSIDDLIDEFNLLENVSDELYELKKL
NNLDEKYLISFEDISKNNSTYSVRFINKSNGESVYVETEKEIFSKYSEHITKEISTIK
NSIITDVNGNLLDNIQLDHTSQVNTLNAAFFIQSLIDYSSNKDVLNDLSTSVKVQL
YAQLFSTGLNTIYDSIQLVNLISNAVNDTINVLPTITEGIPIVSTILDGINLGAAIKEL
LDEHDPLLKKELEAKVGVLAINMSLSIAATVASIVGIGAEVTIFLLPIAGISAGIPSL
VNNELILHDKATSVVNYFNHLSESKKYGPLKTEDDKILVPIDDLVISEIDFNNNSIK
LGTCNILAMEGGSGHTVTGNIDHFFSSPSISSHIPSLSIYSAIGIETENLDFSKKIMM
LPNAPSRVFWWETGAVPGLRSLENDGTRLLDSIRDLYPGKFYWRFYAFFDYAITT
LKPVYEDTNIKIKLDKDTRNFIMPTITTNEIRNKLSYSFDGAGGTYSLLLSSYPIST
NINLSKDDLWIFNIDNEVREISIENGTIKKGKLIKDVLSKIDINKNKLIIGNQTIDFSG
DIDNKDRYIFLTCELDDKISLIIEINLVAKSYSLLLSGDKNYLISNLSNIIEKINTLGL
DSKNIAYNYTDESNNKYFGAISKTSQKSIIHYKKDSKNILEFYNDSTLEFNSKDFIA
EDINVFMKDDINTITGKYYVDNNTDKSIDFSISLVSKNQVKVNGLYLNESVYSSY
LDFVKNSDGHHNTSNFMNLFLDNISFWKLFGFENINFVIDKYFTLVGKTNLGYVE
FICDNNKNIDIYFGEWKTSSSKSTIFSGNGRNVVVEPIYNPDTGEDISTSLDFSYEPL
YGIDRYINKVLIAPDLYTSLININTNYYSNEYYPEIIVLNPNTFHKKVNINLDSSSFE
YKWSTEGSDFILVRYLEESNKKILQKIRIKGILSNTQSFNKMSIDFKDIKKLSLGYI
MSNFKSFNSENELDRDHLGFKIIDNKTYYYDEDSKLVKGLININNSLFYFDPIEFN
LVTGWQTINGKKYYFDINTGAALISYKIINGKHFYFNNDGVMQLGVFKGPDGFE
YFAPANTQNNNIEGQAIVYQSKFLTLNGKKYYFDNDSKAVTGWRIINNEKYYFN
PNNAIAAVGLQVIDNNKYYFNPDTAIISKGWQTVNGSRYYFDTDTAIAFNGYKTI
DGKHFYFDSDCVVKIGVFSTSNGFEYFAPANTYNNNIEGQAIVYQSKFLTLNGKK
YYFDNNSKAVTGWQTIDSKKYYFNTNTAEAATGWQTIDGKKYYFNTNTAEAAT
GWQTIDGKKYYFNTNTAIASTGYTIINGKHFYFNTDGIMQIGVFKGPNGFEYFAP
ANTDANNIEGQAILYQNEFLTLNGKKYYFGSDSKAVTGWRIINNKKYYFNPNNAI
AAIHLCTINNDKYYFSYDGILQNGYITIERNNFYFDANNESKMVTGVFKGPNGFE
YFAPANTHNNNIEGQAIVYQNKFLTLNGKKYYFDNDSKAVTGWQTIDGKKYYF
NLNTAEAATGWQTIDGKKYYFNLNTAEAATGWQTIDGKKYYFNTNTFIASTGYT
SINGKHFYFNTDGIMQIGVFKGPNGFEYFAPANTHNNNIEGQAILYQNKFLTLNG
KKYYFGSDSKAVTGLRTIDGKKYYFNTNTAVAVTGWQTINGKKYYFNTNTSIAS
TGYTIISGKHFYFNTDGIMQIGVFKGPDGFEYFAPANTDANNIEGQAIRYQNRFLY
LHDNIYYFGNNSKAATGWVTIDGNRYYFEPNTAMGANGYKTIDNKNFYFRNGL
PQIGVFKGSNGFEYFAPANTDANNIEGQAIRYQNRFLHLLGKIYYFGNNSKAVTG
WQTINGKVYYFMPDTAMAAAGGLFEIDGVIYFFGVDGVKAPGIYG SEQ ID NO: 40 - Toxin A-derived recombinant antigen - His-[linear spacer]-Thioredoxin-[thrombin site]-TxA3
HHHHHHHHHGGSGGSGGSGGSGGSGGSGGSGGSGGSGGSHMASDKIIHLTDDSF
DTDVLKADGAILVDFWAEWCGPCKMIAPILDEIADEYQGKLTVAKLNIDQNPGT
APKYGIRGIPTLLLFKNGEVAATKVGALSKGQLKEFLDANLARALVPRGSVTSLY
KKAGSAAAPFTMESKKYGPLKTEDDKILVPIDDLVISEIDFNNNSIKLGTCNILAM
EGGSGHTVTGNIDHFFSSPSISSHIPSLSIYSAIGIETENLDFSKKIMMLPNAPSRVF
WWETGAVPGLRSLENDGTRLLDSIRDLYPGKFYWRFYAFFDYAITTLKPVYEDT
NIKIKLDKDTRNFIMPTITTNEIRNKLSYSFDGAGGTYSLLLSSYPISTNINLSKDDL
WIFNIDNEVREISIENGTIKKGKLIKDVLSKIDINKNKLIIGNQTIDFSGDIDNKDRYI
FLTCELDDKISLIIEINLVAKSYSLLLSGDKNYLISNLSNIIEKINTLGLDSKNIAYNY -continued

| SEQ ID NOs |
| --- |

TDESNNKYFGAISKTSQKSIIHYKKDSKNILEFYNDSTLEFNSKDFIAEDINVFMKD
DINTITGKYYVDNNTDKSIDFSISLVSKNQVKVNGLYLNESVYSSYLDFVKNSDG
HHNTSNFMNLFLDNISFWKLFGFENINFVIDKYFTLVGKTNLGYVEFICDNNKNID
IYFGEWKTSSSKSTIFSGNGRNVVVEPIYNPDTGEDISTSLDFSYEPLYGIDRYINK
VLIAPDLYTSLININTNYYSNEYYPEIIVLNPNTFHKKVNINLDSSSFEYKWSTEGS
DFILVRYLEESNKKILQKIRIKGILSNTQSFNKMSIDFKDIKKLSLGYIMSNFKSFNS
ENELDRDHLGFKIIDNKTYYYDEDSKLVKGLININNSLFYFDPIEFNLVTGWQTIN
GKKYYFDINTGAALISYKIINGKHFYFNNDGVMQLGVFKGPDGFEYFAPANTQN
NNIEGQAIVYQSKFLTLNGKKYYFDNDSKAVTGWRIINNEKYYFNPNNAIAAVG
LQVIDNNKYYFNPDTAIISKGWQTVNGSRYYFDTDTAIAFNGYKTIDGKHFYFDS
DCVVKIGVFSTSNGFEYFAPANTYNNNIEGQAIVYQSKFLTLNGKKYYFDNNSKA
VTGWQTIDSKKYYFNTNTAEAATGWQTIDGKKYYFNTNTAEAATGWQTIDGKK
YYFNTNTAIASTGYTIINGKHFYFNTDGIMQIGVFKGPNGFEYFAPANTDANNIEG
QAILYQNEFLTLNGKKYYFGSDSKAVTGWRIINNKKYYFNPNNAIAAIHLCTINN
DKYYFSYDGILQNGYITIERNNFYFDANNESKMVTGVFKGPNGFEYFAPANTHN
NNIEGQAIVYQNKFLTLNGKKYYFDNDSKAVTGWQTIDGKKYYFNLNTAEAAT
GWQTIDGKKYYFNLNTAEAATGWQTIDGKKYYFNTNTFIASTGYTSINGKHFYF
NTDGIMQIGVFKGPNGFEYFAPANTHNNNIEGQAILYQNKFLTLNGKKYYFGSDS
KAVTGLRTIDGKKYYFNTNTAVAVTGWQTINGKKYYFNTNTSIASTGYTIISGKH
FYFNTDGIMQIGVFKGPDGFEYFAPANTDANNIEGQAIRYQNRFLYLHDNIYYFG
NNSKAATGWVTIDGNRYYFEPNTAMGANGYKTIDNKNFYFRNGLPQIGVFKGS
NGFEYFAPANTDANNIEGQAIRYQNRFLHLLGKIYYFGNNSKAVTGWQTINGKV
YYFMPDTAMAAAGGLFEIDGVIYFFGVDGVKAPGIYG

SEQ ID NO: 41 - Toxin A-derived recombinant antigen - His-[helical spacer]-Thioredoxin-[thrombin site]-TxA3
HHHHHHHHHHGGSLAEAAAKEAAAKEAAAKEAAAKEAAAKAAAGGSHMASD
KIIHLTDDSFDTDVLKADGAILVDFWAEWCGPCKMIAPILDEIADEYQGKLTVAK
LNIDQNPGTAPKYGIRGIPTLLLFKNGEVAATKVGALSKGQLKEFLDANLARALV
PRGSVTSLYKKAGSAAAPFTMESKKYGPLKTEDDKILVPIDDLVISEIDFNNNSIK
LGTCNILAMEGGSGHTVTGNIDHFFSSPSISSHIPSLSIYSAIGIETENLDFSKKIMM
LPNAPSRVFWWETGAVPGLRSLENDGTRLLDSIRDLYPGKFYWRFYAFFDYAITT
LKPVYEDTNIKIKLDKDTRNFIMPTITTNEIRNKLSYSFDGAGGTYSLLLSSYPIST
NINLSKDDLWIFNIDNEVREISIENGTIKKGKLIKDVLSKIDINKNKLIIGNQTIDFSG
DIDNKDRYIFLTCELDDKISLIIEINLVAKSYSLLLSGDKNYLISNLSNIIEKINTLGL
DSKNIAYNYTDESNNKYFGAISKTSQKSIIHYKKDSKNILEFYNDSTLEFNSKDFIA
EDINVFMKDDINTITGKYYVDNNTDKSIDFSISLVSKNQVKVNGLYLNESVYSSY
LDFVKNSDGHHNTSNFMNLFLDNISFWKLFGFENINFVIDKYFTLVGKTNLGYVE
FICDNNKNIDIYFGEWKTSSSKSTIFSGNGRNVVVEPIYNPDTGEDISTSLDFSYEPL
YGIDRYINKVLIAPDLYTSLININTNYYSNEYYPEIIVLNPNTFHKKVNINLDSSSFE
YKWSTEGSDFILVRYLEESNKKILQKIRIKGILSNTQSFNKMSIDFKDIKKLSLGYI
MSNFKSFNSENELDRDHLGFKIIDNKTYYYDEDSKLVKGLININNSLFYFDPIEFN
LVTGWQTINGKKYYFDINTGAALISYKIINGKHFYFNNDGVMQLGVFKGPDGFE
YFAPANTQNNNIEGQAIVYQSKFLTLNGKKYYFDNDSKAVTGWRIINNEKYYFN
PNNAIAAVGLQVIDNNKYYFNPDTAIISKGWQTVNGSRYYFDTDTAIAFNGYKTI
DGKHFYFDSDCVVKIGVFSTSNGFEYFAPANTYNNNIEGQAIVYQSKFLTLNGKK
YYFDNNSKAVTGWQTIDSKKYYFNTNTAEAATGWQTIDGKKYYFNTNTAEAAT
GWQTIDGKKYYFNTNTAIASTGYTIINGKHFYFNTDGIMQIGVFKGPNGFEYFAP
ANTDANNIEGQAILYQNEFLTLNGKKYYFGSDSKAVTGWRIINNKKYYFNPNNAI
AAIHLCTINNDKYYFSYDGILQNGYITIERNNFYFDANNESKMVTGVFKGPNGFE
YFAPANTHNNNIEGQAIVYQNKFLTLNGKKYYFDNDSKAVTGWQTIDGKKYYF
NLNTAEAATGWQTIDGKKYYFNLNTAEAATGWQTIDGKKYYFNTNTFIASTGYT
SINGKHFYFNTDGIMQIGVFKGPNGFEYFAPANTHNNNIEGQAILYQNKFLTLNG
KKYYFGSDSKAVTGLRTIDGKKYYFNTNTAVAVTGWQTINGKKYYFNTNTSIAS
TGYTIISGKHFYFNTDGIMQIGVFKGPDGFEYFAPANTDANNIEGQAIRYQNRFLY
LHDNIYYFGNNSKAATGWVTIDGNRYYFEPNTAMGANGYKTIDNKNFYFRNGL
PQIGVFKGSNGFEYFAPANTDANNIEGQAIRYQNRFLHLLGKIYYFGNNSKAVTG
WQTINGKVYYFMPDTAMAAAGGLFEIDGVIYFFGVDGVKAPGIYG SEQ ID NO: 42 - Toxin A-derived recombinant antigen - His-Thioredoxin-[linear spacer]-[thrombin site]-TxA3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALGGSGGSGGSGGSGGSGGSGGSGGSGGSLVPRGSGSAAAPFTM
ESKKYGPLKTEDDKILVPIDDLVISEIDFNNNSIKLGTCNILAMEGGSGHTVTGNID
HFFSSPSISSHIPSLSIYSAIGIETENLDFSKKIMMLPNAPSRVFWWETGAVPGLRSL
ENDGTRLLDSIRDLYPGKFYWRFYAFFDYAITTLKPVYEDTNIKIKLDKDTRNFIM
PTITTNEIRNKLSYSFDGAGGTYSLLLSSYPISTNINLSKDDLWIFNIDNEVREISIEN
GTIKKGKLIKDVLSKIDINKNKLIIGNQTIDFSGDIDNKDRYIFLTCELDDKISLIIEI
NLVAKSYSLLLSGDKNYLISNLSNIIEKINTLGLDSKNIAYNYTDESNNKYFGAISK
TSQKSIIHYKKDSKNILEFYNDSTLEFNSKDFIAEDINVFMKDDINTITGKYYVDN
NTDKSIDFSISLVSKNQVKVNGLYLNESVYSSYLDFVKNSDGHHNTSNFMNLFLD
NISFWKLFGFENINFVIDKYFTLVGKTNLGYVEFICDNNKNIDIYFGEWKTSSSKS
TIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA -continued SEQ ID NOs LISYKIINGKHFYFNNDGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTAIASTG
YTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQN
GYITIERNNFYFDANNESKMVTGVFKGPNGFEYFAPANTHNNNIEGQAIVYQNKF
LTLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTHNNNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG SEQ ID NO: 43 - Toxin A-derived recombinant antigen - His-Thioredoxin-[helical spacer]-[thrombin site]-TxA3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAAPFTMESKKYGPLKTEDDKILVPIDDLVISEIDFNNNSIKLGTCNILAMEGGS
GHTVTGNIDHFFSSPSISSHIPSLSIYSAIGIETENLDFSKKIMMLPNAPSRVFWWET
GAVPGLRSLENDGTRLLDSIRDLYPGKFYWRFYAFFDYAITTLKPVYEDTNIKIKL
DKDTRNFIMPTITTNEIRNKLSYSFDGAGGTYSLLLSSYPISTNINLSKDDLWIFNID
NEVREISIENGTIKKGKLIKDVLSKIDINKNKLIIGNQTIDFSGDIDNKDRYIFLTCEL
DDKISLIIEINLVAKSYSLLLSGDKNYLISNLSNIIEKINTLGLDSKNIAYNYTDESN
NKYFGAISKTSQKSIIHYKKDSKNILEFYNDSTLEFNSKDFIAEDINVFMKDDINTI
TGKYYVDNNTDKSIDFSISLVSKNQVKVNGLYLNESVYSSYLDFVKNSDGHHNT
SNFMNLFLDNISFWKLFGFENINFVIDKYFTLVGKTNLGYVEFICDNNKNIDIYFG
EWKTSSSKSTIFSGNGRNVVVEPIYNPDTGEDISTSLDFSYEPLYGIDRYINKVLIA
PDLYTSLININTNYYSNEYYPEIIVLNPNTFHKKVNINLDSSSFEYKWSTEGSDFIL
VRYLEESNKKILQKIRIKGILSNTQSFNKMSIDFKDIKKLSLGYIMSNFKSFNSENE
LDRDHLGFKIIDNKTYYYDEDSKLVKGLININNSLFYFDPIEFNLVTGWQTINGKK
YYFDINTGAALISYKIINGKHFYFNNDGVMQLGVFKGPDGFEYFAPANTQNNNIE
GQAIVYQSKFLTLNGKKYYFDNDSKAVTGWRIINNEKYYFNPNNAIAAVGLQVI
DNNKYYFNPDTAIISKGWQTVNGSRYYFDTDTAIAFNGYKTIDGKHFYFDSDCV
VKIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG SEQ ID NO: 44 - Toxin B-derived recombinant antigen - His-[linear spacer]-NusA-[thrombin site]-TxB4
HHHHHHHHGGSGGSGGSGGSGGSGGSGGSGGSGGSHMASNKEILAVVEA
VSNEKALPREKIFEALESALATATKKKYEQEIDVRVQIDRKSGDFDTPRRWLVVD
EVTQPTKEITLEAARYEDESLNLGDYVEDQIESVTFDRITTQTAKQVIVQKVREAE
RAMVVDQFREHEGEIITGVVKKVNRDNISLDLGNNAEAVILREDMLPRENFRPG
DRVRGVLYSVRPEARGAQLFVTRSKPEMLIELFRIEVPEIGEEVIEIKAAARDPGSR
AKIAVKTNDKRIDPVGACVGMRGARVQAVSTELGGERIDIVLWDDNPAQFVINA
MAPADVASIVVDEDKHTMDIAVEAGNLAQAIGRNGQNVRLASQLSGWELNVMT
VDDLQAKHQAEAHAAIDTFTKYLDIDEDFATVLVEEGFSTLEELAYVPMKELLEI
EGLDEPTVEALRERAKNALATIAQAQEESLGDNKPADDLLNLEGVDRDLAFKLA
ARGVCTLEDLAEQGIDDLADIEGLTDEKAGALIMAARNICWFGDEASGALVPRG
SVTSLYKKAGSAAAPFTMSIIKDISSKEYISFNPKENKITVKSKNLPELSTLLQEIRN
NSNSSDIELEEKVMLTECEINVISNIDTQIVEERIEEAKNLTSDSINYIKDEFKLIESIS
DALCDLKQQNELEDSHFISFEDISETDEGFSIRFINKETGESIFVETEKTIFSEYANHI
TEEISKIKGTIFDTVNGKLVKKVNLDTTHEVNTLNAAFFIQSLIEYNSSKESLSNLS
VAMKVQVYAQLFSTGLNTITDAAKVVELVSTALDETIDLLPTLSEGLPIIATIIDGV
SLGAAIKELSETSDPLLRQEIEAKIGIMAVNLTTATTAIITSSLGIASGFSILLVPLAG
ISAGIPSLVNNELVLRDKATKVVDYFKHVSLVETEGVFTLLDDKIMMPQDDLVIS
EIDENNNSIVLGKCEIWRMEGGSGHTVTDDIDHFFSAPSITYREPHLSIYDVLEVQ
KEELDLSKDLMVLPNAPNRVFAWETGWTPGLRSLENDGTKLLDRIRDNYEGEFY
WRYFAFIADALITTLKPRYEDTNIRINLDSNTRSFIVPIITTEYIREKLSYSFYGSGGT
YALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLN
SNHIQQKIDYIGFNSELQKNIPYSFVDSEGKENGFINGSTKEGLFVSELPDVVLISK -continued

| SEQ ID NOs |
|---|

VYMDDSKPSFGYYSNNLKDVKVITKDNVNILTGYYLKDDIKISLSLTLQDEKTIK
LNSVHLDESGVAEILKFMNRKGNTNTSDSLMSFLESMNIKSIFVNFLQSNIKFILD
ANFIISGTTSIGQFEFICDENDNIQPYFIKFNTLETNYTLYVGNRQNMIVEPNYDLD
DSGDISSTVINFSQKYLYGIDSCVNKVVISPNIYTDEINITPVYETNNTYPEVIVLDA
NYINEKINVNINDLSIRYVWSNDGNDFILMSTSEENKVSQVKIRFVNVFKDKTLA
NKLSFNFSDKQDVPVSEIILSFTPSYYEDGLIGYDLGLVSLYNEKFYINNFGMMVS
GLIYINDSLYYFKPPVNNLITGFVTVGDDKYYFNPINGGAASIGETIIDDKNYYFN
QSGVLQTGVFSTEDGFKYFAPANTLDENLEGEAIDFTGKLIIDENIYYFDDNYRGA
VEWKELDGEMHYFSPETGKAFKGLNQIGDYKYYFNSDGVMQKGFVSINDNKHY
FDDSGVMKVGYTEIDGKHFYFAENGEMQIGVFNTEDGFKYFAHHNEDLGNEEG
EEISYSGILNFNNKIYYFDDSFTAVVGWKDLEDGSKYYFDEDTAEAYIGLSLINDG
QYYFNDDGIMQVGFVTINDKVFYFSDSGIIESGVQNIDDNYFYIDDNGIVQIGVFD
TSDGYKYFAPANTVNDNIYGQAVEYSGLVRVGEDVYYFGETYTIETGWIYDME
NESDKYYFNPETKKACKGINLIDDIKYYFDEKGIMRTGLISFENNNYYFNENGEM
QFGYINIEDKMFYFGEDGVMQIGVFNTPDGFKYFAHQNTLDENFEGESINYTGW
LDLDEKRYYFTDEYIAATGSVIIDGEEYYFDPDTAQLVISE.

SEQ ID NO: 45 - Toxin B-derived recombinant antigen - His-NusA-[linear spacer]-[thrombin site]-TxB4
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALGGSGGSGGSGGSGGSGGSGGSGGSGGSLVPRGSGS
AAAPFTMSIIKDISSKEYISFNPKENKITVKSKNLPELSTLLQEIRNNSNSSDIELEEK
VMLTECEINVISNIDTQIVEERIEEAKNLTSDSINYIKDEFKLIESISDALCDLKQQN
ELEDSHFISFEDISETDEGFSIRFINKETGESIFVETEKTIFSEYANHITEEISKIKGTIF
DTVNGKLVKKVNLDTTHEVNTLNAAFFIQSLIEYNSSKESLSNLSVAMKVQVYA
QLFSTGLNTITDAAKVVELVSTALDETIDLLPTLSEGLPIIATIIDGVSLGAAIKELS
ETSDPLLRQEIEAKIGIMAVNLTTATTAIITSSLGIASGFSILLVPLAGISAGIPSLVN
NELVLRDKATKVVDYFKHVSLVETEGVFTLLDDKIMMPQDDLVISEIDFNNNSIV
LGKCEIWRMEGGSGHTVTDDIDHFFSAPSITYREPHLSIYDVLEVQKEELDLSKDL
MVLPNAPNRVFAWETGWTPGLRSLENDGTKLLDRIRDNYEGEFYWRYFAFIAD
ALITTLKPRYEDTNIRINLDSNTRSFIVPIITTEYIREKLSYSFYGSGGTYALSLSQYN
MGINIELSESDVWIIDVDNVVRDVTIESDKIKKGDLIEGILSTLSIEENKIILNSHEIN
FSGEVNGSNGFVSLTFSILEGINAIIEVDLLSKSYKLLISGELKILMLNSNHIQQKID
YIGFNSELQKNIPYSFVDSEGKENGFINGSTKEGLFVSELPDVVLISKVYMDDSKP
SFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSI
GQFEFICDENDNIQPYFIKFNTLETNYTLYVGNRQNMIVEPNYDLDDSGDISSTVI
NFSQKYLYGIDSCVNKVVISPNIYTDEINITPVYETNNTYPEVIVLDANYINEKINV
NINDLSIRYVWSNDGNDFILMSTSEENKVSQVKIRFVNVFKDKTLANKLSFNFSD
KQDVPVSEIILSFTPSYYEDGLIGYDLGLVSLYNEKFYINNFGMMVSGLIYINDSL
YYFKPPVNNLITGFVTVGDDKYYFNPINGGAASIGETIIDDKNYYFNQSGVLQTG
VFSTEDGFKYFAPANTLDENLEGEAIDFTGKLIIDENIYYFDDNYRGAVEWKELD
GEMHYFSPETGKAFKGLNQIGDYKYYFNSDGVMQKGFVSINDNKHYFDDSGVM
KVGYTEIDGKHFYFAENGEMQIGVFNTEDGFKYFAHHNEDLGNEEGEEISYSGIL
NFNNKIYYFDDSFTAVVGWKDLEDGSKYYFDEDTAEAYIGLSLINDGQYYFNDD
GIMQVGFVTINDKVFYFSDSGIIESGVQNIDDNYFYIDDNGIVQIGVFDTSDGYKY
FAPANTVNDNIYGQAVEYSGLVRVGEDVYYFGETYTIETGWIYDMENESDKYYF
NPETKKACKGINLIDDIKYYFDEKGIMRTGLISFENNNYYFNENGEMQFGYINIED
KMFYFGEDGVMQIGVFNTPDGFKYFAHQNTLDENFEGESINYTGWLDLDEKRY
YFTDEYIAATGSVIIDGEEYYFDPDTAQLVISE.

SEQ ID NO: 46 - Toxin B-derived recombinant antigen - His-[helical spacer]-[thrombin site]-NusA-B4
HHHHHHHHHHGGSLAEAAAKEAAAKEAAAKEAAAKEAAAKAAAGGSHMASN
KEILAVVEAVSNEKALPREKIFEALESALATATKKKYEQEIDVRVQIDRKSGDFDT
FRRWLVVDEVTQPTKEITLEAARYEDESLNLGDYVEDQIESVTFDRITTQTAKQVI
VQKVREAERAMVVDQFREHEGEIITGVVKKVNRDNISLDLGNNAEAVILREDML
PRENFRPGDRVRGVLYSVRPEARGAQLFVTRSKPEMLIELFRIEVPEIGEEVIEIKA
AARDPGSRAKIAVKTNDKRIDPVGACVGMRGARVQAVSTELGGERIDIVLWDD
NPAQFVINAMAPADVASIVVDEDKHTMDIAVEAGNLAQAIGRNGQNVRLASQLS
GWELNVMTVDDLQAKHQAEAHAAIDTFTKYLDIDEDFATVLVEEGFSTLEELAY
VPMKELLEIEGLDEPTVEALRERAKNALATIAQAQEESLGDNKPADDLLNLEGV
DRDLAFKLAARGVCTLEDLAEQGIDDLADIEGLTDEKAGALIMAARNICWFGDE
ASGALVPRGSVTSLYKKAGSAAAPFTMSIIKDISSKEYISFNPKENKITVKSKNLPE
LSTLLQEIRNNSNSSDIELEEKVMLTECEINVISNIDTQIVEERIEEAKNLTSDSINYI
KDEFKLIESISDALCDLKQQNELEDSHFISFEDISETDEGFSIRFINKETGESIFVETE
KTIFSEYANHITEEISKIKGTIFDTVNGKLVKKVNLDTTHEVNTLNAAFFIQSLIEY
NSSKESLSNLSVAMKVQVYAQLFSTGLNTITDAAKVVELVSTALDETIDLLPTLSE
GLPIIATIIDGVSLGAAIKELSETSDPLLRQEIEAKIGIMAVNLTTATTAIITSSLGIAS -continued

| SEQ ID NOs |
|---|
| GFSILLVPLAGISAGIPSLVNNELVLRDKATKVVDYFKHVSLVETEGVFTLLDDKI<br>MMPQDDLVISEIDFNNNSIVLGKCEIWRMEGGSGHTVTDDIDHFFSAPSITYREPH<br>LSIYDVLEVQKEELDLSKDLMVLPNAPNRVFAWETGWTPGLRSLENDGTKLLDR<br>IRDNYEGEFYWRYFAFIADALITTLKPRYEDTNIRINLDSNTRSFIVPIITTEYIREKL<br>SYSFYGSGGTYALSLSQYNMGINIELSESDVWIIDVDNVVRDVTIESDKIKKGDLI<br>EGILSTLSIEENKIILNSHEINFSGEVNGSNGFVSLTFSILEGINAIIEVDLLSKSYKLL<br>ISGELKILMLNSNHIQQKIDYIGFNSELQKNIPYSFVDSEGKENGFINGSTKEGLFV<br>SELPDVVLISKVYMDDSKPSFGYYSNNLKDVKVITKDNVNILTGYYLKDDIKISLS<br>LTLQDEKTIKLNSVHLDESGVAEILKFMNRKGNTNTSDSLMSFLESMNIKSIFVNF<br>LQSNIKFILDANFIISGTTSIGQFEFICDENDNIQPYFIKFNTLETNYTLYVGNRQNM<br>IVEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYYEDGLIGYDLGLVSLYNEKFYI<br>NNFGMMVSGLIYINDSLYYFKPPVNNLITGFVTVGDDKYYFNPINGGAASIGETII<br>DDKNYYFNQSGVLQTGVFSTEDGFKYFAPANTLDENLEGEAIDFTGKLIIDENIY<br>YFDDNYRGAVEWKELDGEMHYFSPETGKAFKGLNQIGDYKYYFNSDGVMQKG<br>FVSINDNKHYFDDSGVMKVGYTEIDGKHFYFAENGEMQIGVFNTEDGFKYFAHH<br>NEDLGNEEGEEISYSGILNFNNKIYYFDDSFTAVVGWKDLEDGSKYYFDEDTAEA<br>YIGLSLINDGQYYFNDDGIMQVGFVTINDKVFYFSDSGIIESGVQNIDDNYFYIDD<br>NGIVQIGVPDTSDGYKYFAPANTVNDNIYGQAVEYSGLVRVGEDVYYFGETYTI<br>ETGWIYDMENESDKYYFNPETKKACKGINLIDDIKYYFDEKGIMRTGLISFENNN<br>YYFNENGEMQFGYINIEDKMFYFGEDGVMQIGVFNTPDGFKYFAHQNTLDENFE<br>GESINYTGWLDLDEKRYYFTDEYIAATGSVIIDGEEYYPDPDTAQLVISE |
| SEQ ID NO: 47 - Toxin B-derived recombinant antigen - His-NusA-[helical spacer]-[thrombin site]-TxB4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALLAEAAAKEAAAKEAAAKEAAAKEAAAKAAAGGS<br>LVPRGSGSAAAPFTMSIIKDISSKEYISFNPKENKITVKSKNLPELSTLLQEIRNNSN<br>SSDIELEEKVMLTECEINVISNIDTQIVEERIEEAKNLTSDSINYIKDEFKLIESISDAL<br>CDLKQQNELEDSHFISFEDISETDEGFSIRFINKETGESIFVETEKTIFSEYANHITEEI<br>SKIKGTIFDTVNGKLVKKVNLDTTHEVNTLNAAFFIQSLIEYNSSKESLSNLSYAM<br>KVQVYAQLFSTGLNTITDAAKVVELVSTALDETIDLLPTLSEGLPIIATIIDGVSLG<br>AAIKELSETSDPLLRQEIEAKIGIMAVNLTTATTAIITSSLGIASGFSILLVPLAGISA<br>GIPSLVNNELVLRDKATKVVDYFKHVSLVETEGVFTLLDDKIMMPQDDLVISEID<br>FNNNSIVLGKCEIWRMEGGSGHTVTDDIDHFFSAPSITYREPHLSIYDVLEVQKEE<br>LDLSKDLMVLPNAPNRVFAWETGWTPGLRSLENDGTKLLDRIRDNYEGEFYWR<br>YFAFIADALITTLKPRYEDTNIRINLDSNTRSFIVPIITTEYIREKLSYSFYGSGGTYA<br>LSLSQYNMGINIELSESDVWIIDVDNVVRDVTIESDKIKKGDLIEGILSTLSIEENKII<br>LNSHEINFSGEVNGSNGFVSLTFSILEGINAIIEVDLLSKSYKLLISGELKILMLNSN<br>HIQQKIDYIGFNSELQKNIPYSFVDSEGKENGFINGSTKEGLFVSELPDVVLISKVY<br>MDDSKPSFGYYSNNLKDVKVITKDNVNILTGYYLKDDIKISLSLTLQDEKTIKLNS<br>VHLDESGVAEILKFMNRKGNTNTSDSLMSFLESMNIKSIFVNFLQSNIKFILDANFI<br>ISGTTSIGQFEFICDENDNIQPYFIKFNTLETNYTLYVGNRQNMIVEPNYDLDDSGD<br>ISSTVINFSQKYLYGIDSCVNKVVISPNIYTDEINITPVYETNNTYPEVIVLDANYIN<br>EKINVNINDLSIRYVWSNDGNDFILMSTSEENKVSQVKIRFVNVFKDKTLANKLS<br>FNFSDKQDVPVSEIILSFTPSYYEDGLIGYDLGLVSLYNEKFYINNFGMMVSGLIYI<br>NDSLYYFKPPVNNLITGFVTVGDDKYYFNPINGGAASIGETIIDDKNYYFNQSGVL<br>QTGVFSTEDGFKYFAPANTLDENLEGEAIDFTGKLIIDENIYYFDDNYRGAVEWK<br>ELDGEMHYFSPETGKAFKGLNQIGDYKYYFNSDGVMQKGFVSINDNKHYFDDS<br>GVMKVGYTEIDGKHFYFAENGEMQIGVFNTEDGFKYFAHHNEDLGNEEGEEISY<br>SGILNFNNKIYYFDDSFTAVVGWKDLEDGSKYYFDEDTAEAYIGLSLINDGQYYF<br>NDDGIMQVGFVTINDKVFYFSDSGIIESGVQNIDDNYFYIDDNGIVQIGVFDTSDG<br>YKYFAPANTVNDNIYGQAVEYSGLVRVGEDVYYFGETYTIETGWIYDMENESD<br>KYYFNPETKKACKGINLIDDIKYYFDEKGIMRTGLISFENNNYYFNENGEMQFGY<br>INIEDKMFYFGEDGVMQIGVFNTPDGFKYFAHQNTLDENFEGESINYTGWLDLDE<br>KRYYFTDEYIAATGSVIIDGEEYYFDPDTAQLVISE |
| SEQ ID NO: 48 - Toxin B-derived recombinant antigen - His-[linear spacer]-Thioredoxin-[thrombin site]-TxB4<br>HHHHHHHHHHGGSGGSGGSGGSGGSGGSGGSGGSGGSGGSHMASDKIIHLTDD<br>SFDTDVLKADGAILVDFWAEWCGPCKMIAPILDEIADEYQGKLTVAKLNIDQNP<br>GTAPKYGIRGIPTLLLFKNGEVAATKVGALSKGQLKEFLDANLARALVPRGSVTS<br>LYKKAGSAAAPFTMSIIKDISSKEYISFNPKENKITVKSKNLPELSTLLQEIRNNSNS<br>SDIELEEKVMLTECEINVISNIDTQIVEERIEEAKNLTSDSINYIKDEFKLIESISDAL<br>CDLKQQNELEDSHFISFEDISETDEGFSIRFINKETGESIFVETEKTIFSEYANHITEEI<br>SKIKGTIFDTVNGKLVKKVNLDTTHEVNTLNAAFFIQSLIEYNSSKESLSNLSYAM<br>KVQVYAQLFSTGLNTITDAAKVVELVSTALDETIDLLPTLSEGLPIIATIIDGVSLG<br>AAIKELSETSDPLLRQEIEAKIGIMAVNLTTATTAIITSSLGIASGFSILLVPLAGISA |

-continued

| SEQ ID NOs |
|---|
| GIPSLVNNELVLRDKATKVVDYFKHVSLVETEGVFTLLDDKIMMPQDDLVISEID<br>FNNNSIVLGKCEIWRMEGGSGHTVTDDIDHFFSAPSITYREPHLSIYDVLEVQKEE<br>LDLSKDLMVLPNAPNRVFAWETGWTPGLRSLENDGTKLLDRIRDNYEGEFYWR<br>YFAFIADALITTLKPRYEDTNIRINLDSNTRSFIVPIITTEYIREKLSYSFYGSGGTYA<br>LSLSQYNMGINIELSESDVWIIDVDNVVRDVTIESDKIKKGDLIEGILSTLSIEENKII<br>LNSHEINFSGEVNGSNGFVSLTFSILEGINAIIEVDLLSKSYKLLISGELKILMLNSN<br>HIQQKIDYIGFNSELQKNIPYSFVDSEGKENGFINGSTKEGLFVSELPDVVLISKVY<br>MDDSKPSFGYYSNNLKDVKVITKDNVNILTGYYLKDDIKISLSLTLQDEKTIKLNS<br>VHLDESGVAEILKFMNRKGNTNTSDSLMSFLESMNIKSIFVNFLQSNIKFILDANFI<br>ISGTTSIGQFEFICDENDNIQPYFIKFNTLETNYTLYVGNRQNMIVEPNYDLDDSGD<br>ISSTVINFSQKYLYGIDSCVNKVVISPNIYTDEINITPVYETNNTYPEVIVLDANYIN<br>EKINVNINDLSIRYVWSNDGNDFILMSTSEENKVSQVKIRFVNVFKDKTLANKLS<br>FNFSDKQDVPVSEIILSFTPSYYEDGLIGYDLGLVSLYNEKFYINNFGMMVSGLIYI<br>NDSLYYFKPPVNNLITGFVTVGDDKYYFNPINGGAASIGETIIDDKNYYFNQSGVL<br>QTGVFSTEDGFKYFAPANTLDENLEGEAIDFTGKLIIDENIYYFDDNYRGAVEWK<br>ELDGEMHYFSPETGKAFKGLNQIGDYKYYFNSDGVMQKGFVSINDNKHYFDDS<br>GVMKVGYTEIDGKHFYFAENGEMQIGVFNTEDGFKYFAHHNEDLGNEEGEEISY<br>SGILNFNNKIYYFDDSFTAVVGWKDLEDGSKYYFDEDTAEAYIGLSLINDGQYYF<br>NDDGIMQVGFVTINDKVFYFSDSGRESGVQNIDDNYFYIDDNGIVQIGVFDTSDG<br>YKYFAPANTVNDNIYGQAVEYSGLVRVGEDVYYFGETYTIETGWIYDMENESD<br>KYYFNPETKKACKGINLIDDIKYYFDEKGIMRTGLISFENNNYYFNENGEMQFGY<br>INIEDKMFYFGEDGVMQIGVFNTPDGFKYFAHQNTLDENFEGESINYTGWLDLDE<br>KRYYFTDEYIAATGSVIIDGEEYYFDPDTAQLVISE |
| SEQ ID NO: 49 - Toxin B-derived recombinant antigen - His-Thioredoxin-[linear spacer]-[thrombin site]-TxB4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALGGSGGSGGSGGSGGSGGSGGSGGSGGSLVPRGSGSAAAPFTM<br>SIIKDISSKEYISFNPKENKITVKSKNLPELSTLLQEIRNNSNSSDIELEEKVMLTECE<br>INVISNIDTQIVEERIEEAKNLTSDSINYIKDEFKLIESISDALCDLKQQNELEDSHFI<br>SFEDISETDEGFSIRFINKETGESIFVETEKTIFSEYANHITEEISKIKGTIIDTVNGKL<br>VKKVNLDTTHEVNTLNAAFFIQSLIEYNSSKESLSNLSVAMKVQVYAQLFSTGLN<br>TITDAAKVVELVSTALDETIDLLPTLSEGLPIIATIIDGVSLGAAIKELSETSDPLLRQ<br>EIEAKIGIMAVNLTTATTAIITSSLGIASGFSILLVPLAGISAGIPSLVNNELVLRDKA<br>TKVVDYFKHVSLVETEGVFTLLDDKIMMPQDDLVISEIDFNNNSIVLGKCEIWRM<br>EGGSGHTVTDDIDHFFSAPSITYREPHLSIYDVLEVQKEELDLSKDLMVLPNAPNR<br>VFAWETGWTPGLRSLENDGTKLLDRIRDNYEGEFYWRYFAFIADALITTLKPRYE<br>DTNIRINLDSNTRSFIVPIITTEYIREKLSYSFYGSGGTYALSLSQYNMGINIELSESD<br>VWIIDVDNVVRDVTIESDKIKKGDLIEGILSTLSIEENKIILNSHEINFSGEVNGSNG<br>FVSLTFSILEGINAIIEVDLLSKSYKLLISGELKILMLNSNHIQQKIDYIGFNSELQKN<br>IPYSFVDSEGKENGFINGSTKEGLFVSELPDVVLISKVYMDDSKPSFGYYSNNLKD<br>VKVITKDNVNILTGYYLKDDIKISLSLTLQDEKTIKLNSVHLDESGVAEILKFMNR<br>KGNTNTSDSLMSFLESMNIKSIFVNFLQSNIKFILDANFIISGTTSIGQFEFICDENDN<br>IQPYFIKFNTLETNYTLYVGNRQNMIVEPNYDLDDSGDISSTVINFSQKYLYGIDS<br>CVNKVVISPNIYTDEINITPVYETNNTYPEVIVLDANYINEKINVNINDLSIRYVWS<br>NDGNDFILMSTSEENKVSQVKIRFVNVFKDKTLANKLSFNFSDKQDVPVSEIILSF<br>TPSYYEDGLIGYDLGLVSLYNEKFYINNFGMMVSGLIYINDSLYYFKPPVNNLITG<br>FVTVGDDKYYFNPINGGAASIGETIIDDKNYYFNQSGVLQTGVFSTEDGFKYFAP<br>ANTLDENLEGEAIDFTGKLIIDENIYYFDDNYRGAVEWKELDGEMHYFSPETGKA<br>FKGLNQIGDYKYYFNSDGVMQKGFVSINDNKHYFDDSGVMKVGYTEIDGKHFY<br>FAENGEMQIGVFNTEDGFKYFAHHNEDLGNEEGEEISYSGILNFNNKIYYFDDSFT<br>AVVGWKDLEDGSKYYFDEDTAEAYIGLSLINDGQYYFNDDGIMQVGFVTINDK<br>VFYFSDSGIIESGVQNIDDNYFYIDDNGIVQIGVFDTSDGYKYFAPANTVNDNIYG<br>QAVEYSGLVRVGEDVYYFGETYTIETGWIYDMENESDKYYFNPETKKACKGINL<br>IDDIKYYFDEKGIMRTGLISFENNNYYFNENGEMQFGYINIEDKMFYFGEDGVMQ<br>IGVFNTPDGFKYFAHQNTLDENFEGESINYTGWLDLDEKRYYFTDEYIAATGSVII<br>DGEEYYFDPDTAQLVISE |
| SEQ ID NO: 50 - Toxin B-derived recombinant antigen - His-[helical spacer]-Thioredoxin-[thrombin site]-TxB4<br>HHHHHHHHHHGGSLAEAAAKEAAAKEAAAKEAAAKEAAAKAAAGGSHMASD<br>KIIHLTDDSFDTDVLKADGAILVDFWAEWCGPCKMIAPILDEIADEYQGKLTVAK<br>LNIDQNPGTAPKYGIRGIPTLLLFKNGEVAATKVGALSKGQLKEFLDANLARALV<br>PRGSVTSLYKKAGSAAAPFTMSIIKDISSKEYISFNPKENKITVKSKNLPELSTLLQ<br>EIRNNSNSSDIELEEKVMLTECEINVISNIDTQIVEERIEEAKNLTSDSINYIKDEFKL<br>IESISDALCDLKQQNELEDSHFISFEDISETDEGFSIRFINKETGESIFVETEKTIFSEY<br>ANHITEEISKIKGTIFDTVNGKLVKKVNLDTTHEVNTLNAAFFIQSLIEYNSSKESL<br>SNLSVAMKVQVYAQLFSTGLNTITDAAKVVELVSTALDETIDLLPTLSEGLPIIATI<br>IDGVSLGAAIKELSETSDPLLRQEIEAKIGIMAVNLTTATTAIITSSLGIASGFSILLV<br>PLAGISAGIPSLVNNELVLRDKATKVVDYFKHVSLVETEGVFTLLDDKIMMPQDD<br>LVISEIDFNNNSIVLGKCEIWRMEGGSGHTVTDDIDHFFSAPSITYREPHLSIYDVL<br>EVQKEELDLSKDLMVLPNAPNRVFAWETGWTPGLRSLENDGTKLLDRIRDNYE<br>GEFYWRYFAFIADALITTLKPRYEDTNIRINLDSNTRSFIVPIITTEYIREKLSYSFYG<br>SGGTYALSLSQYNMGINIELSESDVWIIDVDNVVRDVTIESDKIKKGDLIEGILSTL<br>SIEENKIILNSHEINFSGEVNGSNGFVSLTFSILEGINAIIEVDLLSKSYKLLISGELKI<br>LMLNSNHIQQKIDYIGFNSELQKNIPYSFVDSEGKENGFINGSTKEGLFVSELPDV |

-continued

| SEQ ID NOs |
| --- |

VLISKVYMDDSKPSFGYYSNNLKDVKVITKDNVNILTGYYLKDDIKISLSLTLQD
EKTIKLNSVHLDESGVAEILKFMNRKGNTNTSDSLMSFLESMNIKSIFVNFLQSNI
KFILDANFIISGTTSIGQFEFICDENDNIQPYFIKFNTLETNYTLYVGNRQNMIVEPN
YDLDDSGDISSTVINFSQKYLYGIDSCVNKVVISPNIYTDEINITPVYETNNTYPEVI
VLDANYINEKINVNINDLSIRYVWSNDGNDFILMSTSEENKVSQVKIRFVNVFKD
KTLANKLSFNFSDKQDVPVSEIILSFTPSYYEDGLIGYDLGLVSLYNEKFYINNFG
MMVSGLIYINDSLYYFKPPVNNLITGFVTVGDDKYYFNPINGGAASIGETIIDDKN
YYFNQSGVLQTGVFSTEDGFKYFAPANTLDENLEGEAIDFTGKLIIDENIYYFDDN
YRGAVEWKELDGEMHYFSPETGKAFKGLNQIGDYKYYFNSDGVMQKGFVSIND
NKHYFDDSGVMKVGYTEIDGKHFYFAENGEMQIGVFNTEDGFKYFAHHNEDLG
NEEGEEISYSGILNFNNKIYYFDDSFTAVVGWKDLEDGSKYYFDEDTAEAYIGLS
LINDGQYYFNDDGIMQVGFVTINDKVFYFSDSGIIESGVQNIDDNYFYIDDNGIVQ
IGVFDTSDGYKYFAPANTVNDNIYGQAVEYSGLVRVGEDVYYFGETYTIETGWI
YDMENESDKYYFNPETKKACKGINLIDDIKYYFDEKGIMRTGLISFENNNYYFNE
NGEMQFGYINIEDKMFYFGEDGVMQIGVFNTPDGFKYFAHQNTLDENFEGESIN
YTGWLDLDEKRYYFTDEYIAATGSVIIDGEEYYFDPDTAQLVISE

SEQ ID NO: 51 - Toxin B-derived recombinant antigen - His-Thioredoxin-[Helical spacer]-[thrombin site]-TxB4
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAAPFTMSIIKDISSKEYISFNPKENKITVKSKNLPELSTLLQEIRNNSNSSDIELEE
KVMLTECEINVISNIDTQIVEERIEEAKNLTSDSINYIKDEFKLIESISDALCDLKQQ
NELEDSHFISFEDISETDEGFSIRFINKETGESIFVETEKTIFSEYANHITEEISKIKGTI
FDTVNGKLVKKVNLDTTHEVNTLNAAFFIQSLIEYNSSKESLSNLSVAMKVQVY
AQLFSTGLNTITDAAKVVELVSTALDETIDLLPTLSEGLPIIATIIDGVSLGAAIKEL
SETSDPLLRQEIEAKIGIMAVNLTTATTAIITSSLGIASGFSILLVPLAGISAGIPSLVN
NELVLRDKATKVVDYFKHVSLVETEGVFTLLDDKIMMPQDDLVISEIDFNNNSIV
LGKCEIWRMEGGSGHTVTDDIDHFFSAPSITYREPHLSIYDVLEVQKEELDLSKDL
MVLPNAPNRVFAWETGWTPGLRSLENDGTKLLDRIRDNYEGEFYWRYFAFIAD
ALITTLKPRYEDTNIRINLDSNTRSFIVPIITTEYIREKLSYSFYGSGGTYALSLSQYN
MGINIELSESDVWIIDVDNVVRDVTIESDKIKKGDLIEGILSTLSIEENKIILNSHEIN
FSGEVNGSNGFVSLTFSILEGINAIIEVDLLSKSYKLLISGELKILMLNSNHIQQKID
YIGFNSELQKNIPYSFVDSEGKENGFINGSTKEGLFVSELPDVVLISKVYMDDSKP
SFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSI
GQFEFICDENDNIQPYFIKFNTLETNYTLYVGNRQNMIVEPNYDLDDSGDISSTVI
NFSQKYLYGIDSCVNKVVISPNIYTDEINITPVYETNNTYPEVIVLDANYINEKINV
NINDLSIRYVWSNDGNDFILMSTSEENKVSQVKIRFVNVFKDKTLANKLSFNFSD
KQDVPVSEIILSFTPSYYEDGLIGYDLGLVSLYNEKFYINNFGMMVSGLIYINDSL
YYFKPPVNNLITGFVTVGDDKYYFNPINGGAASIGETIIDDKNYYFNQSGVLQTG
VFSTEDGFKYFAPANTLDENLEGEAIDFTGKLIIDENIYYFDDNYRGAVEWKELD
GEMHYFSPETGKAFKGLNQIGDYKYYFNSDGVMQKGFVSINDNKHYFDDSGVM
KVGYTEIDGKHFYFAENGEMQIGVFNTEDGFKYFAHHNEDLGNEEGEEISYSGIL
NFNNKIYYFDDSFTAVVGWKDLEDGSKYYFDEDTAEAYIGLSLINDGQYYFNDD
GIMQVGFVTINDKVFYFSDSGIIESGVQNIDDNYFYIDDNGIVQIGVFDTSDGYKY
FAPANTVNDNIYGQAVEYSGLVRVGEDVYYFGETYTIETGWIYDMENESDKYYF
NPETKKACKGINLIDDIKYYFDEKGIMRTGLISFENNNYYFNENGEMQFGYINIED
KMFYFGEDGVMQIGVFNTPDGFKYFAHQNTLDENFEGESINYTGWLDLDEKRY
YFTDEYIAATGSVIIDGEEYYFDPDTAQLVISE SEQ ID NO: 52 - Toxin B-derived recombinant antigen - His-[helical spacer]-Thioredoxin-[thrombin site]-TxB3
HHHHHHHHHHGGSLAEAAAKEAAAKEAAAKEAAAKEAAAKAAAGGSHMASD
KIIHLTDDSFDTDVLKADGAILVDFWAEWCGPCKMIAPILDEIADEYQGKLTVAK
LNIDQNPGTAPKYGIRGIPTLLLFKNGEVAATKVGALSKGQLKEFLDANLARALV
PRGSVTSLYKKAGSAAGGSMPQDDLVISEIDFNNNSIVLGKCEIWRMEGGSGHTV
TDDIDHFFSAPSITYREPHLSIYDVLEVQKEELDLSKDLMVLPNAPNRVFAWETG
WTPGLRSLENDGTKLLDRIRDNYEGEFYWRYFAFIADALITTLKPRYEDTNIRINL
DSNTRSFIVPIITTEYIREKLSYSFYGSGGTYALSLSQYNMGINIELSESDVWIIDVD
NVVRDVTIESDKIKKGDLIEGILSTLSIEENKIILNSHEINFSGEVNGSNGFVSLTFSI
LEGINAIIEVDLLSKSYKLLISGELKILMLNSNHIQQKIDYIGFNSELQKNIPYSFVD
SEGKENGFINGSTKEGLFVSELPDVVLISKVYMDDSKPSFGYYSNNLKDVKVITK
DNVNILTGYYLKDDIKISLSLTLQDEKTIKLNSVHLDESGVAEILKFMNRKGNTNT
SDSLMSFLESMNIKSIFVNFLQSNIKFILDANFIISGTTSIGQFEFICDENDNIQPYFIK
FNTLETNYTLYVGNRQNMIVEPNYDLDDSGDISSTVINFSQKYLYGIDSCVNKVV
ISPNIYTDEINITPVYETNNTYPEVIVLDANYINEKINVNINDLSIRYVWSNDGNDFI
LMSTSEENKVSQVKIRFVNVFKDKTLANKLSFNFSDKQDVPVSEIILSFTPSYYED
GLIGYDLGLVSLYNEKFYINNFGMMVSGLIYINDSLYYFKPPVNNLITGFVTVGD
DKYYFNPINGGAASIGETIIDDKNYYFNQSGVLQTGVFSTEDGFKYFAPANTLDE
NLEGEAIDFTGKLIIDENIYYFDDNYRGAVEWKELDGEMHYFSPETGKAFKGLNQ
IGDYKYYFNSDGVMQKGFVSINDNKHYFDDSGVMKVGYTEIDGKHFYFAENGE
MQIGVFNTEDGFKYFAHHNEDLGNEEGEEISYSGILNFNNKIYYFDDSFTAVVGW
KDLEDGSKYYFDEDTAEAYIGLSLINDGQYYFNDDGIMQVGFVTINDKVFYFSDS
GIIESGVQNIDDNYFYIDDNGIVQIGVFDTSDGYKYFAPANTVNDNIYGQAVEYS
GLVRVGEDVYYFGETYTIETGWIYDMENESDKYYFNPETKKACKGINLIDDIKYY -continued

| SEQ ID NOs |
|---|

FDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYY
FDPDTAQLVISE

SEQ ID NO: 53 - Toxin B-derived recombinant antigen - His-Thioredoxin-[helical spacer]-[thrombin site]-TxB3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAGGSMPQDDLVISEIDFNNNSIVLGKCEIWRMEGGSGHTVTDDIDHFFSAPSIT
YREPHLSIYDVLEVQKEELDLSKDLMVLPNAPNRVFAWETGWTPGLRSLENDGT
KLLDRIRDNYEGEFYWRYFAFIADALITTLKPRYEDTNIRINLDSNTRSFIVPIITTE
YIREKLSYSFYGSGGTYALSLSQYNMGINIELSESDVWIIDVDNVVRDVTIESDKI
KKGDLIEGILSTLSIEENKIILNSHEINFSGEVNGSNGFVSLTFSILEGINAIIEVDLLS
KSYKLLISGELKILMLNSNHIQQKIDYIGFNSELQKNIPYSFVDSEGKENGFINGST
KEGLFVSELPDVVLISKVYMDDSKPSFGYYSNNLKDVKVITKDNVNILTGYYLK
DDIKISLSLTLQDEKTIKLNSVHLDESGVAEILKFMNRKGNTNTSDSLMSFLESMN
IKSIFVNFLQSNIKFILDANFIISGTTSIGQFEFICDENDNIQPYFIKFNTLETNYTLYV
GNRQNMIVEPNYDLDDSGDISSTVINFSQKYLYGIDSCVNKVVISPNIYTDEINITP
VYETNNTYPEVIVLDANYINEKINVNINDLSIRYVWSNDGNDFILMSTSEENKVSQ
VKIRFVNVFKDKTLANKLSFNFSDKQDVPVSEIILSFTPSYYEDGLIGYDLGLVSL
YNEKFYINNFGMMVSGLIYINDSLYYFKPPVNNLITGFVTVGDDKYYFNPINGGA
ASIGETIIDDKNYYFNQSGVLQTGVFSTEDGFKYFAPANTLDENLEGEAIDFTGKL
IIDENIYYFDDNYRGAVEWKELDGEMHYFSPETGKAFKGLNQIGDYKYYFNSDG
VMQKGFVSINDNKHYFDDSGVMKVGYTEIDGKHFYFAENGEMQIGVFNTEDGF
KYFAHHNEDLGNEEGEEISYSGILNFNNKIYYFDDSFTAVVGWKDLEDGSKYYF
DEDTAEAYIGLSLINDGQYYFNDDGIMQVGFVTINDKVFYFSDSGIIESGVQNIDD
NYFYIDDNGIVQIGVFDTSDGYKYFAPANTVNDNIYGQAVEYSGLVRVGEDVYY
FGETYTIETGWIYDMENESDKYYFNPETKKACKGINLIDDIKYYFDEKGIMRTGLI
SFENNNYYFNENGEMQFGYINIEDKMFYFGEDGVMQIGVFNTPDGFKYFAHQNT
LDENFEGESINYTGWLDLDEKRYYFTDEYIAATGSVIIDGEEYYFDPDTAQLVISE SEQ ID NO: 54 - Toxin B-derived recombinant antigen - His-[linear spacer]-Thioredoxin-[thrombin site]-TxB3
HHHHHHHHHGGSGGSGGSGGSGGSGGSGGSGGSGGSGGSGGSHMASDKIIHLTDDSF
DTDVLKADGAILVDFWAEWCGPCKMIAPILDEIADEYQGKLTVAKLNIDQNPGT
APKYGIRGIPTLLLFKNGEVAATKVGALSKGQLKEFLDANLARALVPRGSVTSLY
KKAGSAAGGSMPQDDLVISEIDFNNNSIVLGKCEIWRMEGGSGHTVTDDIDHFFS
APSITYREPHLSIYDVLEVQKEELDLSKDLMVLPNAPNRVFAWETGWTPGLRSLE
NDGTKLLDRIRDNYEGEFYWRYFAFIADALITTLKPRYEDTNIRINLDSNTRSFIVP
IITTEYIREKLSYSFYGSGGTYALSLSQYNMGINIELSESDVWIIDVDNVVRDVTIE
SDKIKKGDLIEGILSTLSIEENKIILNSHEINFSGEVNGSNGFVSLTFSILEGINAIIEV
DLLSKSYKLLISGELKILMLNSNHIQQKIDYIGFNSELQKNIPYSFVDSEGKENGFI
NGSTKEGLFVSELPDVVLISKVYMDDSKPSFGYYSNNLKDVKVITKDNVNILTGY
YLKDDIKISLSLTLQDEKTIKLNSVHLDESGVAEILKFMNRKGNTNTSDSLMSFLE
SMNIKSIFVNFLQSNIKFILDANFIISGTTSIGQFEFICDENDNIQPYFIKFNTLETNYT
LYVGNRQNMIVEPNYDLDDSGDISSTVINFSQKYLYGIDSCVNKVVISPNIYTDEI
NITPVYETNNTYPEVIVLDANYINEKINVNINDLSIRYVWSNDGNDFILMSTSEEN
KVSQVKIRFVNVFKDKTLANKLSFNFSDKQDVPVSEIILSFTPSYYEDGLIGYDLG
LVSLYNEKFYINNFGMMVSGLIYINDSLYYFKPPVNNLITGFVTVGDDKYYFNPI
NGGAASIGETIIDDKNYYFNQSGVLQTGVFSTEDGFKYFAPANTLDENLEGEAIDF
TGKLIIDENIYYFDDNYRGAVEWKELDGEMHYFSPETGKAFKGLNQIGDYKYYF
NSDGVMQKGFVSINDNKHYFDDSGVMKVGYTEIDGKHFYFAENGEMQIGVFNT
EDGFKYFAHHNEDLGNEEGEEISYSGILNFNNKIYYFDDSFTAVVGWKDLEDGSK
YYFDEDTAEAYIGLSLINDGQYYFNDDGIMQVGFVTINDKVFYFSDSGIIESGVQN
IDDNYFYIDDNGIVQIGVFDTSDGYKYFAPANTVNDNIYGQAVEYSGLVRVGED
VYYFGETYTIETGWIYDMENESDKYYFNPETKKACKGINLIDDIKYYFDEKGIMR
TGLISFENNNYYFNENGEMQFGYINIEDKMFYFGEDGVMQIGVFNTPDGFKYFA
HQNTLDENFEGESINYTGWLDLDEKRYYFTDEYIAATGSVIIDGEEYYFDPDTAQ
LVISE SEQ ID NO: 55 - Toxin B-derived recombinant antigen - His-Thioredoxin-[linear spacer]-[thrombin site]-TxB3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALGGSGGSGGSGGSGGSGGSGGSGGSGGSGGSLVPRGSGSAAGGSMP
QDDLVISEIDFNNNSIVLGKCEIWRMEGGSGHTVTDDIDHFFSAPSITYREPHLSIY
DVLEVQKEELDLSKDLMVLPNAPNRVFAWETGWTPGLRSLENDGTKLLDRIRD
NYEGEFYWRYFAFIADALITTLKPRYEDTNIRINLDSNTRSFIVPIITTEYIREKLSY
SFYGSGGTYALSLSQYNMGINIELSESDVWIIDVDNVVRDVTIESDKIKKGDLIEGI
LSTLSIEENKIILNSHEINFSGEVNGSNGFVSLTFSILEGINAIIEVDLLSKSYKLLISG
ELKILMLNSNHIQQKIDYIGFNSELQKNIPYSFVDSEGKENGFINGSTKEGLFVSEL
PDVVLISKVYMDDSKPSFGYYSNNLKDVKVITKDNVNILTGYYLKDDIKISLSLTL
QDEKTIKLNSVHLDESGVAEILKFMNRKGNTNTSDSLMSFLESMNIKSIFVNFLQS
NIKFILDANFIISGTTSIGQFEFICDENDNIQPYFIKFNTLETNYTLYVGNRQNMIVE
PNYDLDDSGDISSTVINFSQKYLYGIDSCVNKVVISPNIYTDEINITPVYETNNTYP
EVIVLDANYINEKINVNINDLSIRYVWSNDGNDFILMSTSEENKVSQVKIRFVNVF -continued

| SEQ ID NOs |
|---|

KDKTLANKLSFNFSDKQDVPVSEIILSFTPSYYEDGLIGYDLGLVSLYNEKFYINN
FGMMVSGLIYINDSLYYFKPPVNNLITGFVTVGDDKYYFNPINGGAASIGETIIDD
KNYYFNQSGVLQTGVFSTEDGFKYFAPANTLDENLEGEAIDFTGKLIIDENIYYFD
DNYRGAVEWKELDGEMHYFSPETGKAFKGLNQIGDYKYYFNSDGVMQKGFVSI
NDNKHYFDDSGVMKVGYTEIDGKHFYFAENGEMQIGVFNTEDGFKYFAHHNED
LGNEEGEEISYSGILNFNNKIYYFDDSFTAVVGWKDLEDGSKYYFDEDTAEAYIG
LSLINDGQYYFNDDGIMQVGFVTINDKVFYFSDSGIIESGVQNIDDNYFYIDDNGI
VQIGVFDTSDGYKYFAPANTVNDNIYGQAVEYSGLVRVGEDVYYFGETYTIETG
WIYDMENESDKYYFNPETKKACKGINLIDDIKYYFDEKGIMRTGLISFENNNYYF
NENGEMQFGYINIEDKMFYFGEDGVMQIGVFNTPDGFKYFAHQNTLDENFEGESI
NYTGWLDLDEKRYYFTDEYIAATGSVIIDGEEYYFDPDTAQLVISE

SEQ ID NO: 56 - Toxin B-derived recombinant antigen - His-NusA-[Intein A sequence]-TxB4-His
MGSSHHHHHHSHMASNKEILAVVEAVSNEKALPREKIFEALESALATATKKKYE
QEIDVRVQIDRKSGDFDTFRRWLVVDEVTQPTKEITLEAARYEDESLNLGDYVED
QIESVTFDRITTQTAKQVIVQKVREAERAMVVDQFREHEGEIITGVVKKVNRDNI
SLDLGNNAEAVILREDMLPRENFRPGDRVRGVLYSVRPEARGAQLFVTRSKPEM
LIELFRIEVPEIGEEVIEIKAAARDPGSRAKIAVKTNDKRIDPVGACVGMRGARVQ
AVSTELGGERIDIVLWDDNPAQFVINAMAPADVASIVVDEDKHTMDIAVEAGNL
AQAIGRNGQNVRLASQLSGWELNVMTVDDLQAKHQAEAHAAIDTFTKYLDIDE
DFATVLVEEGFSTLEELAYVPMKELLEIEGLDEPTVEALRERAKNALATIAQAQE
ESLGDNKPADDLLNLEGVDRDLAFKLAARGVCTLEDLAEQGIDDLADIEGLTDE
KAGALIMAARNICWFGDEASGALRTRVKVVKNKALAEGTRIFDPVTGTTHRIED
VVDGRKPIHVVAAAKDGTLHARPVVSWFDQGTRDVIGLRIAGGAILWATPDHK
VLTEYGWRAAGELRKGDRVAQPRRFDGFGDSAPIPARVQALADALDDKFLHDM
LAEELRYSVIREVLPTRRARTFGLEVEELHTLVAEGVVVHNSSPPFKQAEFGSAA
APFTMSIIKDISSKEYISFNPKENKITVKSKNLPELSTLLQEIRNNSNSSDIELEEKV
MLTECEINVISNIDTQIVEERIEEAKNLTSDSINYIKDEFKLIESISDALCDLKQQNE
LEDSHFISFEDISETDEGFSIRFINKETGESIFVETEKTIFSEYANHITEEISKIKGTIFD
TVNGKLVKKVNLDTTHEVNTLNAAFFIQSLIEYNSSKESLSNLSVAMKVQVYAQ
LFSTGLNTITDAAKVVELVSTALDETIDLLPTLSEGLPIIATIIDGVSLGAAIKELSET
SDPLLRQEIEAKIGIMAVNLTTATTAIITSSLGIASGFSILLVPLAGISAGIPSLVNNE
LVLRDKATKVVDYFKHVSLVETEGVFTLLDDKIMMPQDDLVISEIDFNNNSIVLG
KCEIWRMEGGSGHTVTDDIDHFFSAPSITYREPHLSIYDVLEVQKEELDLSKDLM
VLPNAPNRVFAWETGWTPGLRSLENDGTKLLDRIRDNYEGEFYWRYFAFIADAL
ITTLKPRYEDTNIRINLDSNTRSFIVPIITTEYIREKLSYSFYGSGGTYALSLSQYNM
GINIELSESDVWIIDVDNVVRDVTIESDKIKKGDLIEGILSTLSIEENKIILNSHEINFS
GEVNGSNGFVSLTFSILEGINAIIEVDLLSKSYKLLISGELKILMLNSNHIQQKIDYI
GFNSELQKNIPYSFVDSEGKENGFINGSTKEGLFVSELPDVVLISKVYMDDSKPSF
GYYSNNLKDVKVITKDNVNILTGYYLKDDIKISLSLTLQDEKTIKLNSVHLDESG
VAEILKFMNRKGNTNTSDSLMSFLESMNIKSIFVNFLQSNIKFILDANFIISGTTSIG
QFEFICDENDNIQPYFIKFNTLETNYTLYVGNRQNMIVEPNYDLDDSGDISSTVINF
SQKYLYGIDSCVNKVVISPNIYTDEINITPVYETNNTYPEVIVLDANYINEKINVNI
NDLSIRYVWSNDGNDFILMSTSEENKVSQVKIRFVNVFKDKTLANKLSFNFSDKQ
DVPVSEIILSFTPSYYEDGLIGYDLGLVSLYNEKFYINNFGMMVSGLIYINDSLYYF
KPPVNNLITGFVTVGDDKYYFNPINGGAASIGETIIDDKNYYFNQSGVLQTGVFST
EDGFKYFAPANTLDENLEGEAIDFTGKLIIDENIYYFDDNYRGAVEWKELDGEM
HYFSPETGKAFKGLNQIGDYKYYFNSDGVMQKGFVSINDNKHYFDDSGVMKVG
YTEIDGKHFYFAENGEMQIGVFNTEDGFKYFAHHNEDLGNEEGEEISYSGILNFN
NKIYYFDDSFTAVVGWKDLEDGSKYYFDEDTAEAYIGLSLINDGQYYFNDDGIM
QVGFVTINDKVFYFSDSGIIESGVQNIDDNYFYIDDNGIVQIGVFDTSDGYKYFAP
ANTVNDNIYGQAVEYSGLVRVGEDVYYFGETYTIETGWIYDMENESDKYYFNPE
TKKACKGINLIDDIKYYFDEKGIMRTGLISFENNNYYFNENGEMQFGYINIEDKM
FYFGEDGVMQIGVFNTPDGFKYFAHQNTLDENFEGESINYTGWLDLDEKRYYFT
DEYIAATGSVIIDGEEYYFDPDTAQLVISEGHHHHHH SEQ ID NO: 57 - Toxin B-derived recombinant antigen - His-NusA-[Intein BT sequence]-TxB4-His
MGSSHHHHHHSHMASNKEILAVVEAVSNEKALPREKIFEALESALATATKKKYE
QEIDVRVQIDRKSGDFDTFRRWLVVDEVTQPTKEITLEAARYEDESLNLGDYVED
QIESVTFDRITTQTAKQVIVQKVREAERAMVVDQFREHEGEIITGVVKKVNRDNI
SLDLGNNAEAVILREDMLPRENFRPGDRVRGVLYSVRPEARGAQLFVTRSKPEM
LIELFRIEVPEIGEEVIEIKAAARDPGSRAKIAVKTNDKRIDPVGACVGMRGARVQ
AVSTELGGERIDIVLWDDNPAQFVINAMAPADVASIVVDEDKHTMDIAVEAGNL
AQAIGRNGQNVRLASQLSGWELNVMTVDDLQAKHQAEAHAAIDTFTKYLDIDE
DFATVLVEEGFSTLEELAYVPMKELLEIEGLDEPTVEALRERAKNALATIAQAQE
ESLGDNKPADDLLNLEGVDRDLAFKLAARGVCTLEDLAEQGIDDLADIEGLTDE
KAGALIMAARNICWFGDEASGALEVFGEFGSGKAFARDTEVYYENDTVPHMESI
EEMYSKYASMNGELPFDNGYAVPLDNVFVYTLDIASGEIKKTRASYIYREKVEK
LIEIKLSSGYSLKVTPSHPVLLFRDGLQWVPAAEVKPGDVVVGVREEVLRRRIISK
GELEFHEVSSVRIIDYNNWVYDLVIPETHNFIAPNGLVLHNTQLAHTLAVMGSAA
APFTMSIIKDISSKEYISFNPKENKITVKSKNLPELSTLLQEIRNNSNSSDIELEEKV
MLTECEINVISNIDTQIVEERIEEAKNLTSDSINYIKDEFKLIESISDALCDLKQQNE
LEDSHFISFEDISETDEGFSIRFINKETGESIFVETEKTIFSEYANHITEEISKIKGTIFD
TVNGKLVKKVNLDTTHEVNTLNAAFFIQSLIEYNSSKESLSNLSVAMKVQVYAQ
LFSTGLNTITDAAKVVELVSTALDETIDLLPTLSEGLPIIATIIDGVSLGAAIKELSET -continued SEQ ID NOs SDPLLRQEIEAKIGIMAVNLTTATTAIITSSLGIASGFSILLVPLAGISAGIPSLVNNE
LVLRDKATKVVDYFKHVSLVETEGVFTLLDDKIMMPQDDLVISEIDFNNNSIVLG
KCEIWRMEGGSGHTVTDDIDHFFSAPSITYREPHLSIYDVLEVQKEELDLSKDLM
VLPNAPNRVFAWETGWTPGLRSLENDGTKLLDRIRDNYEGEFYWRYFAFIADAL
ITTLKPRYEDTNIRINLDSNTRSFIVPIITTEYIREKLSYSFYGSGGTYALSLSQYNM
GINIELSESDVWIIDVDNVVRDVTIESDKIKKGDLIEGILSTLSIEENKIILNSHEINFS
GEVNGSNGFVSLTFSILEGINAIIEVDLLSKSYKLLISGELKILMLNSNHIQQKIDYI
GFNSELQKNIPYSFVDSEGKENGFINGSTKEGLFVSELPDVVLISKVYMDDSKPSF
GYYSNNLKDVKVITKDNVNILTGYYLKDDIKISLSLTLQDEKTIKLNSVHLDESG
VAEILKFMNRKGNTNTSDSLMSFLESMNIKSIFVNFLQSNIKFILDANFIISGTTSIG
QFEFICDENDNIQPYFIKFNTLETNYTLYVGNRQNMIVEPNYDLDDSGDISSTVINF
SQKYLYGIDSCVNKVVISPNIYTDEINITPVYETNNTYPEVIVLDANYINEKINVNI
NDLSIRYVWSNDGNDFILMSTSEENKVSQVKIRFVNVFKDKTLANKLSFNFSDKQ
DVPVSEIILSFTPSYYEDGLIGYDLGLVSLYNEKFYINNFGMMVSGLIYINDSLYYF
KPPVNNLITGFVTVGDDKYYFNPINGGAASIGETIIDDKNYYFNQSGVLQTGVFST
EDGFKYFAPANTLDENLEGEAIDFTGKLIIDENIYYFDDNYRGAVEWKELDGEM
HYFSPETGKAFKGLNQIGDYKYYFNSDGVMQKGFVSINDNKHYFDDSGVMKVG
YTEIDGKHFYFAENGEMQIGVFNTEDGFKYFAHHNEDLGNEEGEEISYSGILNFN
NKIYYFDDSFTAVVGWKDLEDGSKYYFDEDTAEAYIGLSLINDGQYYFNDDGIM
QVGFVTINDKVFYFSDSGIIESGVQNIDDNYFYIDDNGIVQIGVFDTSDGYKYFAP
ANTVNDNIYGQAVEYSGLVRVGEDVYYFGETYTIETGWIYDMENESDKYYFNPE
TKKACKGINLIDDIKYYFDEKGIMRTGLISFENNNYYFNENGEMQFGYINIEDKM
FYFGEDGVMQIGVFNTPDGFKYFAHQNTLDENFEGESINYTGWLDLDEKRYYFT
DEYIAATGSVIIDGEEYYFDPDTAQLVISEGHHHHHH SEQ ID NO: 58 - Toxin A-derived recombinant antigen (TxA4; residues 770-2710) expression construct
MGSSHHHHHHSHMASDKIIHLTDDSIDTDVLKADGAILVDFWAEWCGPCKMIA
PILDEIADEYQGKLTVAKLNIDQNPGTAPKYGIRGIPTLLLFKNGEVAATKVGALS
KGQLKEFLDANLARALEVLFQGPGGSADARAKAQFEEYKRNYFEGAGGSIMSDL
SSKEYIFFDSIDNKLKAKSKNIPGLASISEDIKTLLLDASVSPDTKFILNNLKLNIESS
IGDYIYYEKLEPVKNIIHNSIDDLIDEFNLLENVSDELYELKKLNNLDEKYLISFEDI
SKNNSTYSVRFINKSNGESVYVETEKEIFSKYSEHITKEISTIKNSIITDVNGNLLDN
IQLDHTSQVNTLNAAFFIQSLIDYSSNKDVLNDLSTSVKVQLYAQLFSTGLNTIYD
SIQLVNLISNAVNDTINVLPTITEGIPIVSTILDGINLGAAIKELLDEHDPLLKKELEA
KVGVLAINMSLSIAATVASIVGIGAEVTIFLLPIAGISAGIPSLVNNELILHDKATSV
VNYFNHLSESKKYGPLKTEDDKILVPIDDLVISEIDFNNNSIKLGTCNILAMEGGS
GHTVTGNIDHFISSPSISSHIPSLSIYSAIGIETENLDFSKKIMMLPNAPSRVFWWET
GAVPGLRSLENDGTRLLDSIRDLYPGKFYWRFYAFFDYAITTLKPVYEDTNIKIKL
DKDTRNFIMPTITTNEIRNKLSYSFDGAGGTYSLLLSSYPISTNINLSKDDLWIFNID
NEVREISIENGTIKKGKLIKDVLSKIDINKNKLIIGNQTIDFSGDIDNKDRYIFLTCEL
DDKISLIIEINLVAKSYSLLLSGDKNYLISNLSNIIEKINTLGLDSKNIAYNYTDESN
NKYFGAISKTSQKSIIHYKKDSKNILEFYNDSTLEFNSKDFIAEDINVFMKDDINTI
TGKYYVDNNTDKSIDFSISLVSKNQVKVNGLYLNESVYSSYLDFVKNSDGHHNT
SNFMNLFLDNISFWKLFGFENINFVIDKYFTLVGKTNLGYVEFICDNNKNIDIYFG
EWKTSSSKSTIFSGNGRNVVVEPIYNPDTGEDISTSLDFSYEPLYGIDRYINKVLIA
PDLYTSLININTNYYSNEYYPEIIVLNPNTFHKKVNINLDSSSFEYKWSTEGSDFIL
VRYLEESNKKILQKIRIKGILSNTQSFNKMSIDFKDIKKLSLGYIMSNFKSFNSENE
LDRDHLGFKIIDNKTYYYDEDSKLVKGLININNSLFYFDPIEFNLVTGWQTINGKK
YYFDINTGAALISYKIINGKHFYFNNDGVMQLGVFKGPDGFEYFAPANTQNNNIE
GQAIVYQSKFLTLNGKKYYFDNDSKAVTGWRIINNEKYYFNPNNAIAAVGLQVI
DNNKYYFNPDTAIISKGWQTVNGSRYYFDTDTAIAFNGYKTIDGKHFYFDSDCV
VKIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG SEQ ID NO: 59 - Toxin A-derived recombinant antigen (TxA4 truncate; residues 770-2389) expression construct
MGSSHHHHHHSHMASDKIIHLTDDSFDTDVLKADGAILVDFWAEWCGPCKMIA
PILDEIADEYQGKLTVAKLNIDQNPGTAPKYGIRGIPTLLLFKNGEVAATKVGALS
KGQLKEFLDANLARALVPRGSGGSADARAKAQFBEYKRNYFEGAGGSAAAPFT
MIMSDLSSKEYIFFDSIDNKLKAKSKNIPGLASISEDIKTLLLDASVSPDTKFILNNL
KLNIESSIGDYIYYEKLEPVKNIIHNSIDDLIDEFNLLENVSDELYELKKLNNLDEK
YLISFEDISKNNSTYSVRFINKSNGESVYVETEKEIFSKYSEHITKEISTIKNSIITDV
NGNLLDNIQLDHTSQVNTLNAAFFIQSLIDYSSNKDVLNDLSTSVKVQLYAQLFS
TGLNTIYDSIQLVNLISNAVNDTINVLPTITEGIPIVSTILDGINLGAAIKELLDEHDP
LLKKELEAKVGVLAINMSLSIAATVASIVGIGAEVTIFLLPIAGISAGIPSLVNNELI -continued

| SEQ ID NOs |
|---|
| LHDKATSVVNYFNHLSESKKYGPLKTEDDKILVPIDDLVISEIDFNNNSIKLGTCNI<br>LAMEGGSGHTVTGNIDHFFSSPSISSHIPSLSIYSAIGIETENLDFSKKIMMLPNAPS<br>RVFWWETGAVPGLRSLENDGTRLLDSIRDLYPGKFYWRFYAFFDYAITTLKPVY<br>EDTNIKIKLDKDTRNFIMPTITTNEIRNKLSYSFDGAGGTYSLLLSSYPISTNINLSK<br>DDLWIFNIDNEVREISIENGTIKKGKLIKDVLSKIDINKNKLIIGNQTIDFSGDIDNK<br>DRYIFLTCELDDKISLIIEINLVAKSYSLLLSGDKNYLISNLSNIIEKINTLGLDSKNI<br>AYNYTDESNNKYFGAISKTSQKSIIHYKKDSKNILEFYNDSTLEFNSKDFIAEDINV<br>FMKDDINTITGKYYVDNNTDKSIDFSISLVSKNQVKVNGLYLNESVYSSYLDFVK<br>NSDGHHNTSNFMNLFLDNISFWKLFGFENINFVIDKYFTLVGKTNLGYVEFICDN<br>NKNIDIYFGEWKTSSSKSTIFSGNGRNVVVEPIYNPDTGEDISTSLDFSYEPLYGID<br>RYINKVLIAPDLYTSLININTNYYSNEYYPEIIVLNPNTFHKKVNINLDSSSFENKW<br>STEGSDFILVRYLEESNKKILQKIRIKGILSNTQSFNKMSIDFKDIKKLSLGYIMSNF<br>KSFNSENELDRDHLGFKIIDNKTYYYDEDSKLVKGLININNSLFYFDPIEFNLVTG<br>WQTINGKKYYFDINTGAALISYKIINGKHFYFNNDGVMQLGVFKGPDGFEYFAP<br>ANTQNNNIEGQAIVYQSKFLTLNGKKYYFDNDSKAVTGWRIINNEKYYFNPNNA<br>IAAVGLQVIDNNKYYFNPDTAIISKGWQTVNGSRYYPDTDTAIAFNGYKTIDGKH<br>FYFDSDCVVKIGVFSTSNGFEYFAPANTYNNNIEGQAIVYQSKFLTLNGKKYYFD<br>NNSKAVTGWQTIDSKKYYFNTNTAEAATGWQTIDGKKYYFNTNTAEAATGWQ<br>TIDGKKYYFNTNTAIASTGYTIINGKHFYFNTDGIMQIGVFKGPNGFEYFAPANTD<br>ANNIEGQAILYQNEFLTLNGKKYYFGSDSKAVTGWRIINNKKYYFNPNNAIAAIH<br>LCTINNDKYYFSYDGILQNGYITIERNNFYFDANNESKMVTGVFKGPNGFEYFAP<br>ANTHNNNIEGQAIVYQNKFLTLNGKKYYFDNDSKAVTGWQTIDGKKYYFNLNT<br>AEAATGWQTIDGKKYYFNLNTAEAATGWQTIDGKKYYFNTNTFIAST |

SEQUENCE LISTING

The patent contains a lengthy sequence listing. A copy of the sequence listing is available in electronic form from the USPTO web site (https://seqdata.uspto.gov/docdetail?docId=US12714742B2). An electronic copy of the sequence listing will also be available from the USPTO upon request and payment of the fee set forth in 37 CFR 1.19(b)(3).

The invention claimed is:

1. A method for treating or suppressing *Clostridium difficile* (*C. difficile*) infection in a human, said method comprising administering to said human a therapeutically effective amount of polyclonal antibodies, wherein said polyclonal antibodies bind to a *C. difficile* Toxin B, do not bind to the effector domain and/or to the cysteine protease domain of *C. difficile* Toxin B, and can elicit a *C difficile* Toxin B-neutralizing immune response,
   - wherein said polyclonal antibodies are obtained by immunizing a sheep with a protein comprising:
     - a) an amino acid sequence comprising amino acid residues 767-2366 of a *C. difficile* Toxin B sequence; or
     - b) an amino acid sequence having comprising amino acid residues 1145-2366 of a *C. difficile* Toxin B sequence;
   - to induce production of polyclonal antibodies specific for *C. difficile* Toxin B, with the proviso that the protein does not comprise amino acid residues 543-2366 of the *C. difficile* Toxin B; and
   - wherein said *C. difficile* Toxin B sequence is the amino acid sequence of SEQ ID NO: 2 or the amino acid sequence of SEQ ID NO: 4.

2. The method according to claim 1, wherein the polyclonal antibodies are isolated.

3. The method according to claim 2, wherein the polyclonal antibodies are isolated by affinity purification.

4. The method according to claim 1, wherein said polyclonal antibodies are administered in combination with one or more additional antibodies, wherein the one or more additional antibody is an antibody that binds to a *C. difficile* non-Toxin antigen, and/or is an antibody that binds to a whole cell *C. difficile* bacterium.

5. The method according to claim 4, wherein the one or more antibody is selected from:
   - a) an antibody that binds to antigen from a bacterium that causes nosocomial infection, and/or
   - b) an antibody that binds to a whole cell bacterium that causes nosocomial infection.

6. The method according to claim 4, wherein the one or more antibody is combined with one or more antibiotic.

7. The method according to claim 6, wherein the antibiotic is an antibiotic effective against a bacterium that causes nosocomial infection.

8. The method according to claim 1, wherein the polyclonal antibodies are combined with one or more antibiotic.

9. The method according to claim 8, wherein the antibiotic is an antibiotic effective against a bacterium that causes a nosocomial infection.

10. A method for treating a *C. difficile* infection in a patient comprising:
   - using an in vitro immunoassay method to confirm the presence or absence of a *C. difficile* infection in a patient sample, wherein said immunoassay comprises the steps of:
     - combining the patient sample with polyclonal antibodies for a time sufficient for antibody binding with *C. difficile* Toxin B present in the patient sample;
     - detecting the presence of antibody binding with *C. difficile* Toxin B in the patient sample;

wherein the presence of a *C. difficile* infection is confirmed by detecting the binding of said polyclonal antibodies to a *C. difficile* Toxin B present in said patient sample, wherein failure to detect the binding of said polyclonal antibodies to a *C. difficile* Toxin B present in said patient sample confirms the absence of a *C. difficile* infection, and wherein the said patient confirmed as having *C. difficile* in said patient sample is administered a therapeutically effective amount of the polyclonal antibodies;

wherein said polyclonal antibodies bind to a *C. difficile* Toxin B, do not bind to the effector domain and/or to the cysteine protease domain of *C. difficile* Toxin B, and can elicit a *C. difficile* Toxin B-neutralizing immune response, wherein said polyclonal antibodies are obtained by immunizing a sheep with a protein comprising:

a) an amino acid sequence comprising amino acid residues 767-2366 of a *C. difficile* Toxin B sequence; or b) an amino acid sequence comprising amino acid residues 1145-2366 of a *C. difficile* Toxin B sequence;

to induce production of polyclonal antibodies specific for *C. difficile* Toxin B; with the proviso that the protein does not comprise amino acid residues 543-2366 of the *C. difficile* Toxin B; and wherein said *C. difficile* Toxin B sequence is the amino acid sequence of SEQ ID NO: 2 or the amino acid sequence of SEQ ID NO: 4.

11. The method according to claim 10, wherein the polyclonal antibodies are isolated.

12. The method according to claim 11, wherein the polyclonal antibodies are isolated by affinity purification.

13. The method according to claim 10, wherein said polyclonal antibodies are administered in combination with one or more additional antibodies, wherein the one or more additional antibodies is an antibody that binds to a *C. difficile* non-Toxin, and/or is an antibody that binds to a whole cell *C. difficile* bacterium.

14. The method according to claim 10, wherein said polyclonal antibodies are combined with one or more antibiotic.

* * * * *